(12) United States Patent
Moll et al.

(10) Patent No.: US 8,021,326 B2
(45) Date of Patent: Sep. 20, 2011

(54) INSTRUMENT DRIVER FOR ROBOTIC CATHETER SYSTEM

(75) Inventors: Frederic H. Moll, Woodside, CA (US); Daniel T. Wallace, Burlingame, CA (US); Robert G. Younge, Portola Valley, CA (US); Kenneth M. Martin, Los Gatos, CA (US); Gregory J. Stahler, San Jose, CA (US); David F. Moore, San Carlos, CA (US); Daniel T. Adams, Palo Alto, CA (US); Michael R. Zinn, Pleasanton, CA (US); Gunter D. Niemeyer, Mountain View, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1755 days.

(21) Appl. No.: 11/176,954

(22) Filed: Jul. 6, 2005

(65) Prior Publication Data

US 2006/0084945 A1 Apr. 20, 2006

Related U.S. Application Data

(60) Provisional application No. 60/600,869, filed on Aug. 12, 2004, provisional application No. 60/644,505, filed on Jan. 13, 2005, provisional application No. 60/677,580, filed on May 3, 2005, provisional application No. 60/678,097, filed on May 4, 2005.

(51) Int. Cl.
*A61M 31/00* (2006.01)
(52) U.S. Cl. ........... 604/95.04; 600/114; 600/146
(58) Field of Classification Search .......... 600/407–411, 600/424, 473, 476, 427, 101, 109, 114, 117, 600/118, 139, 146; 606/130; 604/95.04, 604/164.12, 164.09
See application file for complete search history.

(56) References Cited

U.S. PATENT DOCUMENTS 5,710,870 A 1/1998 Ohm et al.
(Continued)

FOREIGN PATENT DOCUMENTS

WO WO 97/44089 11/1997
(Continued)

OTHER PUBLICATIONS

PCT International Search Report for PCT/US2005/007108, Applicant: Hansen Medical, Inc., Forms PCT/ISA/210 and 220, dated Jun. 26, 2005 (9 pages).

(Continued)

*Primary Examiner* — Sanjay Cattungal
(74) *Attorney, Agent, or Firm* — Vista IP Law Group LLP

(57) ABSTRACT

A robotic medical system comprises an operator control station having a master input device, a catheter instrument, and an instrument driver in communication with the operator control station. The catheter instrument includes an elongate flexible catheter member, a flexible control element extending within the catheter member, and a proximal drivable assembly configured to axially move the control element relative to the catheter member to perform a kinematic function at a distal end of the catheter member. The instrument driver is configured to operate the drivable assembly to axially move the control element in response to control signals generated, at least in part, by the master input device. The drivable assembly is mounted to the instrument driver, thereby providing mechanically close relationship between the drivable assembly and the instrument driver.

19 Claims, 49 Drawing Sheets

U.S. PATENT DOCUMENTS

| | | | | |
|---|---|---|---|---|
| 5,722,959 A * | 3/1998 | Bierman | | 604/174 |
| 5,845,646 A * | 12/1998 | Lemelson | | 128/899 |
| 6,004,271 A * | 12/1999 | Moore | | 600/445 |
| 6,061,587 A * | 5/2000 | Kucharczyk et al. | | 600/411 |
| 6,381,483 B1 * | 4/2002 | Hareyama et al. | | 600/407 |
| 6,491,701 B2 | 12/2002 | Tierney et al. | | |
| 6,530,913 B1 * | 3/2003 | Giba et al. | | 604/528 |
| 6,544,230 B1 * | 4/2003 | Flaherty et al. | | 604/164.12 |
| 6,551,273 B1 * | 4/2003 | Olson et al. | | 604/103.03 |
| 6,610,007 B2 * | 8/2003 | Belson et al. | | 600/146 |
| 6,669,709 B1 * | 12/2003 | Cohn et al. | | 606/167 |
| 6,905,460 B2 * | 6/2005 | Wang et al. | | 600/102 |
| 7,371,210 B2 * | 5/2008 | Brock et al. | | 600/114 |
| 7,404,824 B1 * | 7/2008 | Webler et al. | | 623/2.36 |
| 7,524,320 B2 | 4/2009 | Tierney et al. | | |
| 2001/0009976 A1 * | 7/2001 | Panescu et al. | | 600/424 |
| 2001/0029366 A1 * | 10/2001 | Swanson et al. | | 606/29 |
| 2002/0087169 A1 * | 7/2002 | Brock et al. | | 606/139 |
| 2002/0138009 A1 * | 9/2002 | Brockway et al. | | 600/485 |
| 2002/0177789 A1 * | 11/2002 | Ferry et al. | | 600/585 |
| 2003/0073908 A1 * | 4/2003 | Desai | | 600/464 |
| 2003/0074011 A1 * | 4/2003 | Gilboa et al. | | 606/130 |
| 2003/0135204 A1 * | 7/2003 | Lee et al. | | 606/1 |
| 2004/0176751 A1 * | 9/2004 | Weitzner et al. | | 606/1 |
| 2004/0193146 A1 * | 9/2004 | Lee et al. | | 606/1 |
| 2004/0220588 A1 * | 11/2004 | Kermode et al. | | 606/129 |
| 2005/0159789 A1 * | 7/2005 | Brockway et al. | | 607/32 |
| 2005/0182295 A1 * | 8/2005 | Soper et al. | | 600/117 |
| 2005/0182330 A1 * | 8/2005 | Brockway et al. | | 600/486 |
| 2005/0222554 A1 | 10/2005 | Wallace et al. | | |
| 2006/0271036 A1 * | 11/2006 | Garabedian et al. | | 606/41 |
| 2007/0038181 A1 * | 2/2007 | Melamud et al. | | 604/158 |
| 2007/0060879 A1 * | 3/2007 | Weitzner et al. | | 604/95.04 |
| 2008/0300592 A1 * | 12/2008 | Weitzner et al. | | 606/41 |
| 2009/0054884 A1 * | 2/2009 | Farley et al. | | 606/15 |

FOREIGN PATENT DOCUMENTS

WO    WO 03/077769    9/2003

OTHER PUBLICATIONS

PCT Written Opinion of the International Search Authority for PCT/US2005/007108, Applicant: Hansen Medical, Inc., Form PCT/ISA/237, dated Jun. 26, 2005 (6 pages).

* cited by examiner

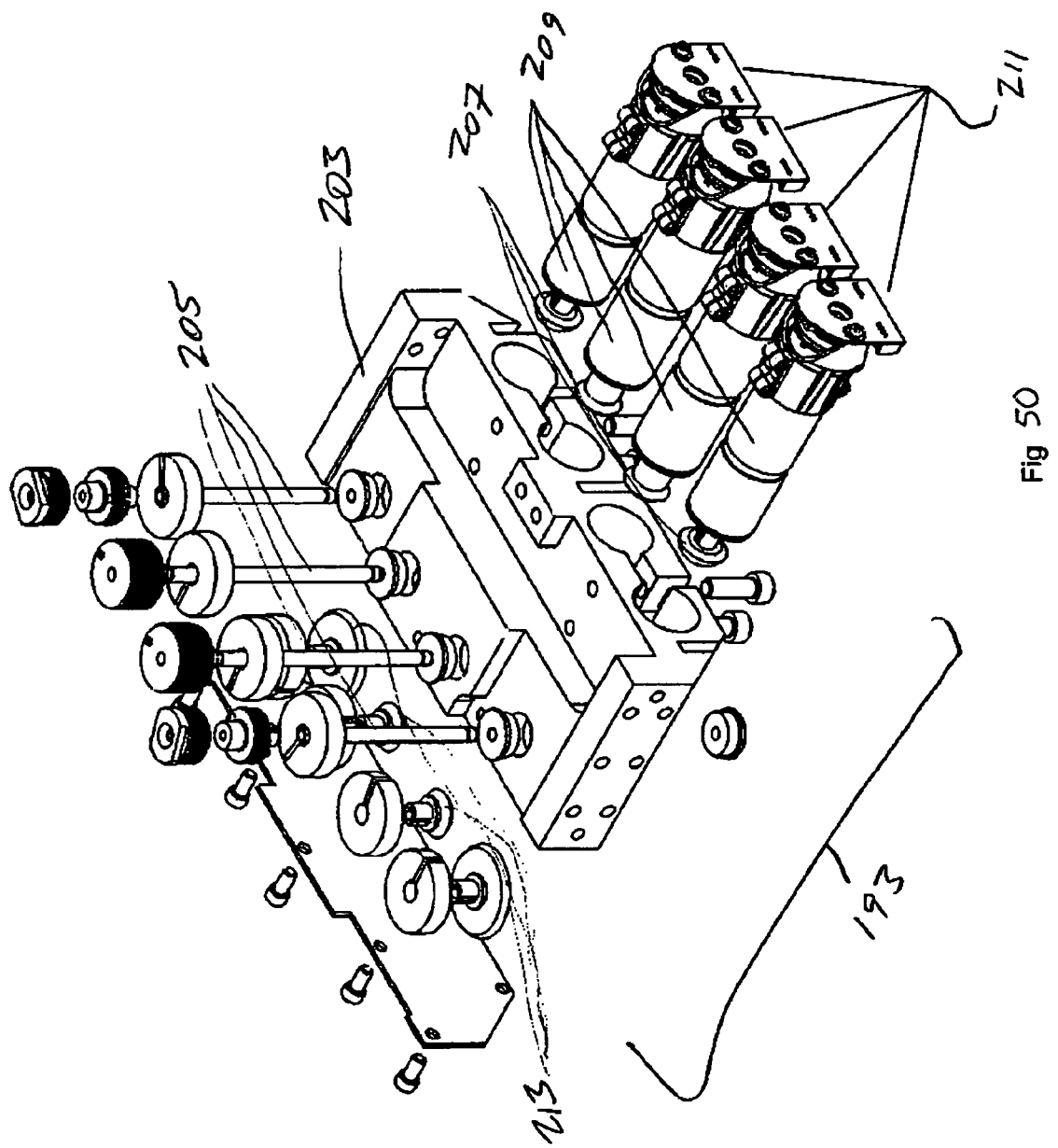

INSTRUMENT DRIVER FOR ROBOTIC CATHETER SYSTEM

RELATED APPLICATION DATA

The present application claims the benefit under 35 U.S.C. §119 to U.S. provisional patent application Ser. Nos. 60/600,869, filed Aug. 12, 2004, 60/644,505, filed Jan. 13, 2005, 60/677,580, filed May 3, 2005, and 60/678,097, filed May 4, 2005. The foregoing applications are hereby incorporated by reference into the present application in their entirety.

FIELD OF INVENTION

The invention relates generally to robotically controlled surgical systems, and more particularly to catheter instruments and instrument drivers and responsive to signals generated at a master controller for manipulating an instrument used in an invasive surgical procedure.

BACKGROUND

Robotic surgical systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be preferably accessed only via naturally-occurring pathways such as blood vessels or the gastrointestinal tract.

SUMMARY OF THE INVENTION

In accordance with a first aspect of the present inventions, a robotic medical system is provided. The system comprises an operator control station having a master input device, a catheter instrument, and an instrument driver in communication with the operator control station. An optional external cable can be used to provide communication between the instrument driver and operator control station. The catheter instrument includes an elongate flexible catheter member, a flexible control element, such as, e.g., a cable, extending within the catheter member, and a proximal drivable assembly configured to axially move the control element relative to the catheter member to perform a kinematic function at a distal end of the catheter member. In one embodiment, the kinematic function comprise a deflection of the distal end of the catheter member. However, it should be appreciated that the kinematic function can include other types of functions, such as, e.g., mechanical manipulation of an end effector at the distal end of the catheter member. In an optional embodiment, the catheter instrument includes a plurality of control elements, in which case, the proximal drivable assembly may be configured to axially and independently move the plurality of control elements within the catheter member to perform a plurality of kinematic functions.

The instrument driver is configured to operate the drivable assembly to axially move the control element in response to control signals generated, at least in part, by the master input device. In an optional embodiment, the instrument driver is also configured to axially displace the catheter member in response to such control signals. The drivable assembly is mounted to the instrument driver. Although the present inventions should not be so limited, the mechanically close relationship between the drivable assembly and the instrument driver minimizes the errors between the actual and predicted kinematic functions otherwise introduced into the system via intervening structure between the drivable assembly and instrument driver. In one embodiment, the drivable assembly is removably mounted to the instrument driver, e.g., to facilitate the exchange of catheter instruments in the case where they are for single use and/or disposable.

In an optional embodiment, the catheter member is a guide member, and the system further comprises a sheath instrument including an elongate flexible sheath catheter member coaxially arranged with the guide catheter member, another flexible control element extending within the sheath catheter member, and another proximal drivable assembly configured to operate by axially moving the other control element relative to the sheath catheter member to perform another kinematic function, e.g., by deflecting the distal end of the sheath catheter member. Like the drivable assembly of the guide instrument, the drivable assembly of the sheath instrument is mounted to the instrument driver, and the instrument driver is configured to operate the drivable assembly of the sheath instrument in response to control signals generated, at least in part, by the master input device. The medical system may conveniently comprise a patient table, and a setup mount mounting the instrument driver to the patient table. In this case, the instrument driver may be rotatably coupled to the setup mount, whereby the catheter member can be rotated about a longitudinal axis.

In accordance with a second aspect of the present inventions, a catheter instrument is provided. The catheter instrument comprises an elongate flexible catheter member, a flexible control element extending within the catheter member, and a drivable assembly mounted on a proximal end of the catheter member. The drivable assembly comprises a base having a mounting surface configured to be mounted on a mounting surface of an instrument driver, and a control element interface assembly mounted within the base and being accessible to a drive element on the instrument driver. For example, the control element interface assembly may be accessible by the drive element at an interface between the respective mounting surfaces of the drivable assembly and instrument driver. As previously discussed, such an arrangement eliminates intervening structure between the driver and drivable assembly, which may minimize errors between the actual and predicted kinematic functions. The drivable assembly may be configured to be removably mounted to the instrument driver, e.g., to facilitate exchanging of catheter instruments. The control element interface assembly is configured to axially move the control element relative to the catheter member to perform a kinematic function. As previously stated, the control element may be, e.g., a cable, and the kinematic function can be, e.g., a deflection of the distal end of the catheter member.

In one embodiment, the control element interface assembly comprises a pulley configured for selectively spooling and unspooling the control element, and an axel on which the pulley is mounted, the axel being configured to be mated with the drive element of the instrument driver. In another embodiment, the catheter instrument comprises a plurality of control elements extending within the catheter member. In this case, the drivable assembly may comprise a plurality of control element interface assemblies mounted within the base and being accessible to a plurality of drive elements on the instrument driver. The control element interface assemblies are configured to axially move the control elements relative to the catheter member to perform a plurality of kinematic functions. Alternatively, a single control element interface assembly can be configured to axially move at least two control elements relative to the catheter member to perform at least two kinematic functions. For example, the single control element interface can be configured to rotate and translate relative to the base to axially move the at least two control elements. In this case, the base may comprise a slot (e.g., a rectilinear slot or an arcuate slot) in which the control element interface assembly translates, and the control element interface assembly may comprise at least two pulleys for spooling and spooling the at least two control elements.

In one embodiment, the base comprises a top portion and a bottom portion having opposing catheter recesses. In this case, the catheter member is received within the opposing catheter recesses when the top and bottom portions are sandwiched together. In another embodiment, the catheter instrument comprises a control element tensioning device operably coupled to the control element, thereby maintaining tension in the control element at all times in order to maximize the responsiveness of the drivable assembly to the instrument driver. In an optional embodiment, the catheter member is a guide member, and the catheter instrument further comprises an elongate flexible sheath catheter member coaxially arranged with the guide catheter member, another flexible control element extending within the sheath catheter member, and another proximal drivable assembly mounted on a proximal end of the sheath catheter member. Like the previously described drivable assembly, the other drivable assembly comprises another base having a mounting surface configured to be mounted on a mounting surface of the instrument driver, and a control element interface assembly mounted within the other base and being accessible to another drive element on the instrument driver. The other control element interface assembly is configured to axially move the other control element relative to the sheath catheter member to perform another kinematic function.

In accordance with a third aspect of the present inventions, another medical system is provided. The medical system comprises the previously described catheter instrument and an instrument driver configured for receiving control signals transmitted from a remote location. The instrument driver comprises a mounting surface on which the base is mounted, a drive element mated with the control element interface assembly, and a motor operably coupled to the drive element. The instrument driver may optionally comprise a movable carriage on which the mounting surface is disposed, such that the instrument base moves with the carriage. The features of the instrument driver will be dictated by the features of the instrument driver.

For example, in the case where the control element interface assembly comprises a pulley and axel configuration, the drive element of the instrument driver can take the form of a socket in which the axel is mounted. In the case where the catheter instrument comprises a plurality of control element interface assemblies, the instrument driver may comprises a plurality of drive elements mated with the plurality of control element interface assemblies, and a plurality of motors operably coupled to the plurality of drive elements. If the control element interface assembly is designed to translate within the slot of an associated base, the instrument driver may comprise a movable element associated with the drive element and movable relative to the mounting surface, and another motor operably coupled to the movable element to move the one control element interface assembly relative to the base. The shape of the slot will dictate the path in which the moving element follows. For example, if the slot is rectilinear, the movable element will be configured to move in a rectilinear path, and if the slot is arcuate, the movable element will be configured to move in an arcuate path. In the case wherein the instrument comprises a coaxial guide/sheath catheter configuration, the instrument driver may further comprise another mounting surface on which the sheath base is mounted, another drive element mated with the sheath control element interface assembly, and another motor operably coupled to the other drive element.

Other and further embodiments and aspects of the invention will become apparent upon review of the following detailed description in view of the illustrated embodiments.

BRIEF DESCRIPTION OF THE DRAWINGS

The drawings illustrate the design and utility of illustrated embodiments of the invention, in which similar elements are referred to by common reference numerals, and in which:

FIG. 46 is a partially exploded view of the instrument driver assembly of FIG. 40;

FIGS. 49 and 50 are exploded views of an alternate instrument driver assembly similar to that depicted in FIG. 40, according to yet another embodiment.

DETAILED DESCRIPTION OF THE ILLUSTRATED EMBODIMENTS

Figure 1:
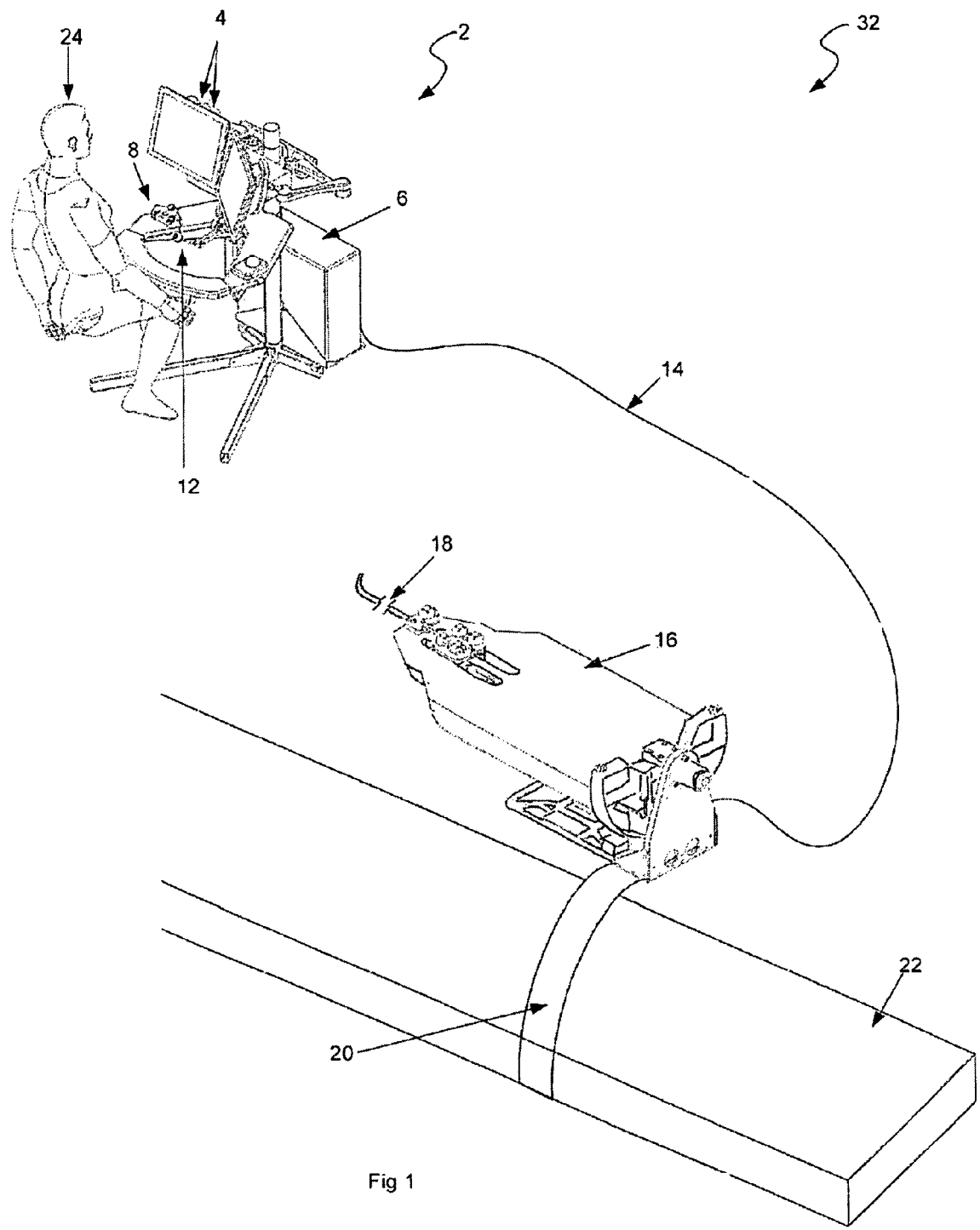
FIG. 1 is a perspective view of a robotic surgical system constructed in accordance with one embodiment of the present inventions.
Figure 2:
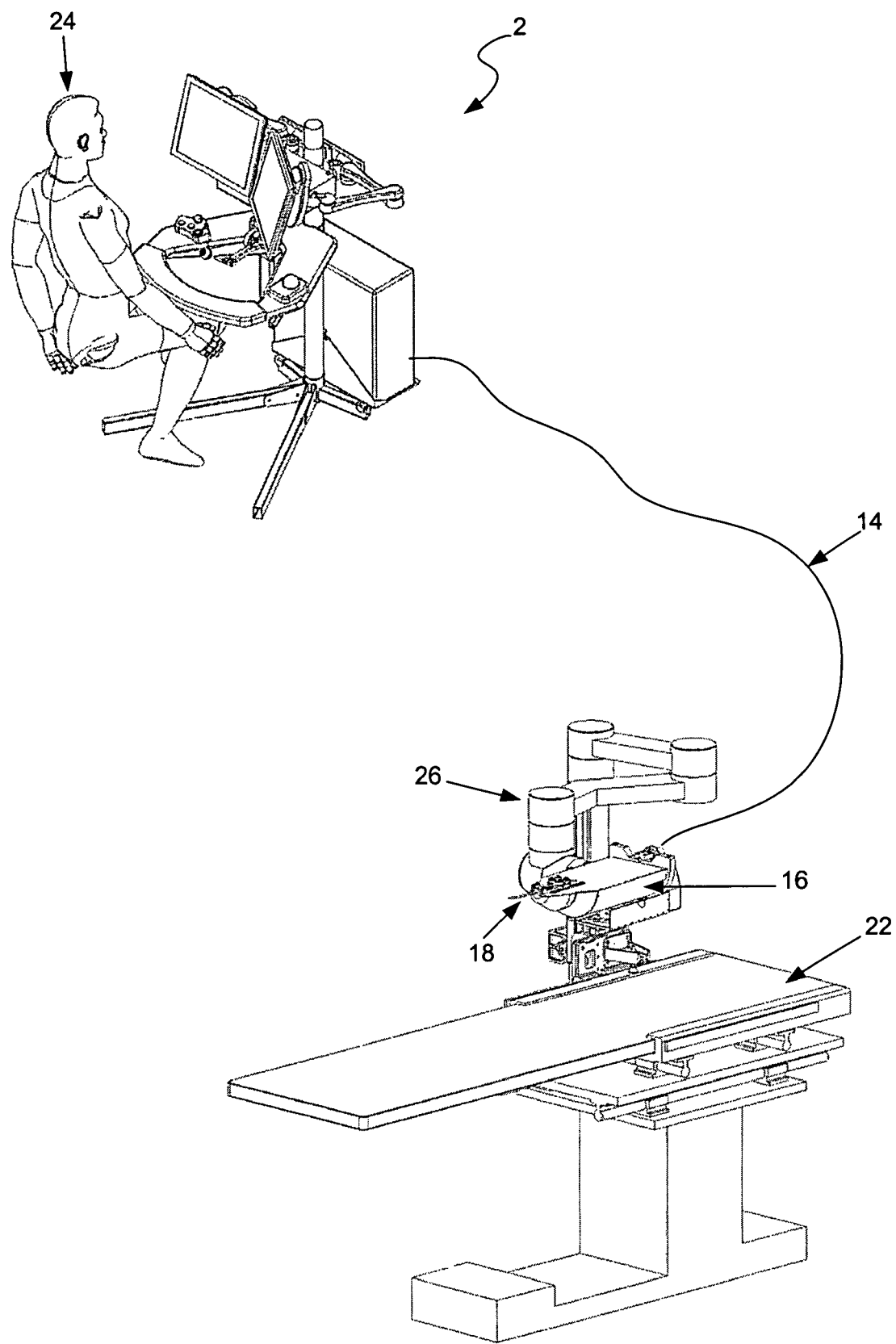
FIG. 2 is a perspective view of a robotic surgical system constructed in accordance with another embodiment of the present inventions.

Referring to FIG. 1, one embodiment of a robotic surgical system (32) includes an operator control station (2) located remotely from an operating table (22), an instrument driver (16) and instrument (18) coupled to the operating table (22) by a mounting brace (20), and a communication link (14), such as an external cable, that transfers signals between the operator control station (2) and instrument driver (16). The operator control station (2) has a control button console (8), a master input device (12), and a display system (4). The master input device (12) is a multi-degree-of-freedom device having multiple joints and associated encoders, thereby allowing an operator (24) to remotely control mechanical movements of the instrument (18). Further, the master input device (12) may have integrated haptics capability for providing tactile feedback to the user. The instrument driver mounting brace (20) of the embodiment illustrated in FIG. 1 is a relatively simple, arcuate-shaped structural member configured to position the instrument driver (16) above a patient (not shown) lying on the table (22). Alternatively, as illustrated in FIG. 2, a movable setup mount (26) can be used to movably support the instrument driver (16) above the table (22) to provide convenient access to the desired portions of the patient (not shown) and provide a means to lock the instrument driver (16) into position subsequent to preferred placement. Further details of various embodiments of operator control stations and movable setup mounts are disclosed in U.S. provisional patent application Ser. Nos. 60/677,580 and 60/678,097, which have previously been incorporated herein by reference.

Figure 3:
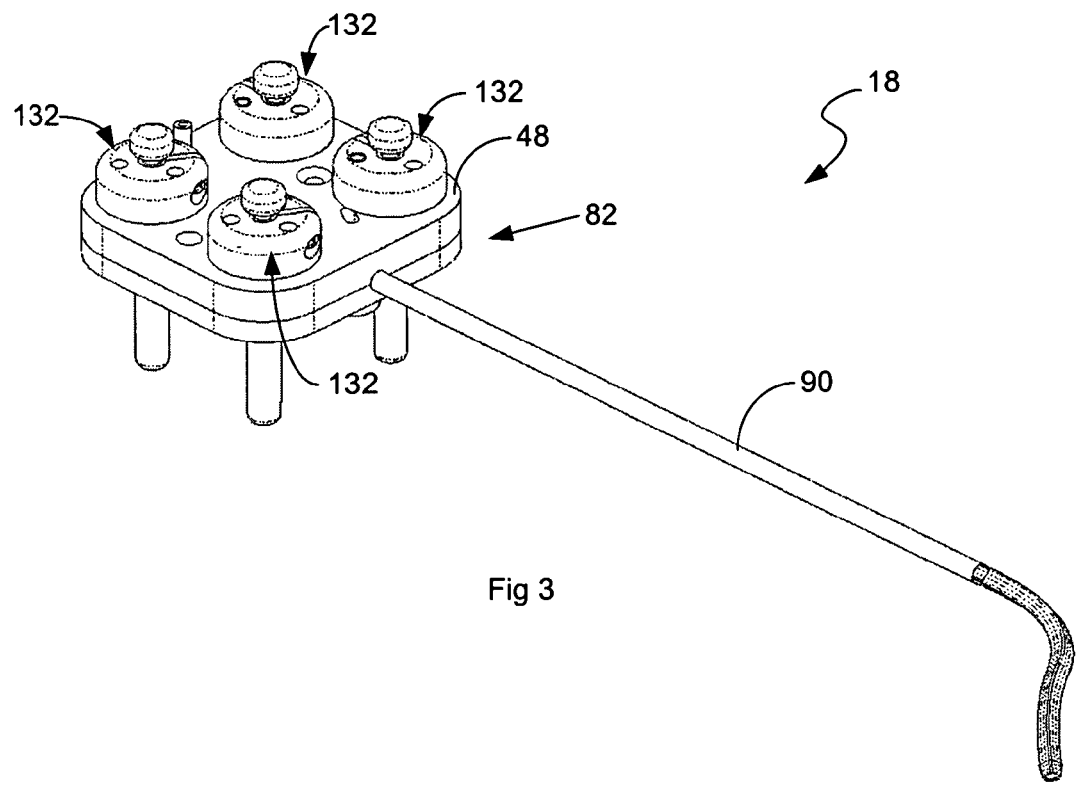
FIG. 3 is a perspective view of a catheter instrument used in either of the robotic surgical systems of FIGS. 1 and 2.

Referring now to FIG. 3, the instrument (18) generally comprises a proximal drivable assembly (82), which includes an instrument base (48) and four control element interface assemblies (132), a catheter member (90), the proximal end of which is mounted within the instrument base (48), and four control or tension elements, such as cables (not shown), extending within the catheter member (90) and operably coupled to the four control element interface assemblies (132), such that operation of the interface assemblies (132) bends the distal end of the catheter member (90) in four separate directions, e.g., by displacing one of the control elements in the proximal direction to deflect the distal end of the catheter member (90) in the predetermined direction dictated by the one control element, while allowing the other three control elements to be displaced in the distal direction as a natural consequence of the catheter member deflect. Alternatively, the interface assemblies (132) can be operated to displace two circumferentially adjacent control elements to provide an infinite amount of deflections depending on the relative displacement of the adjacent control elements.

Figure 4:
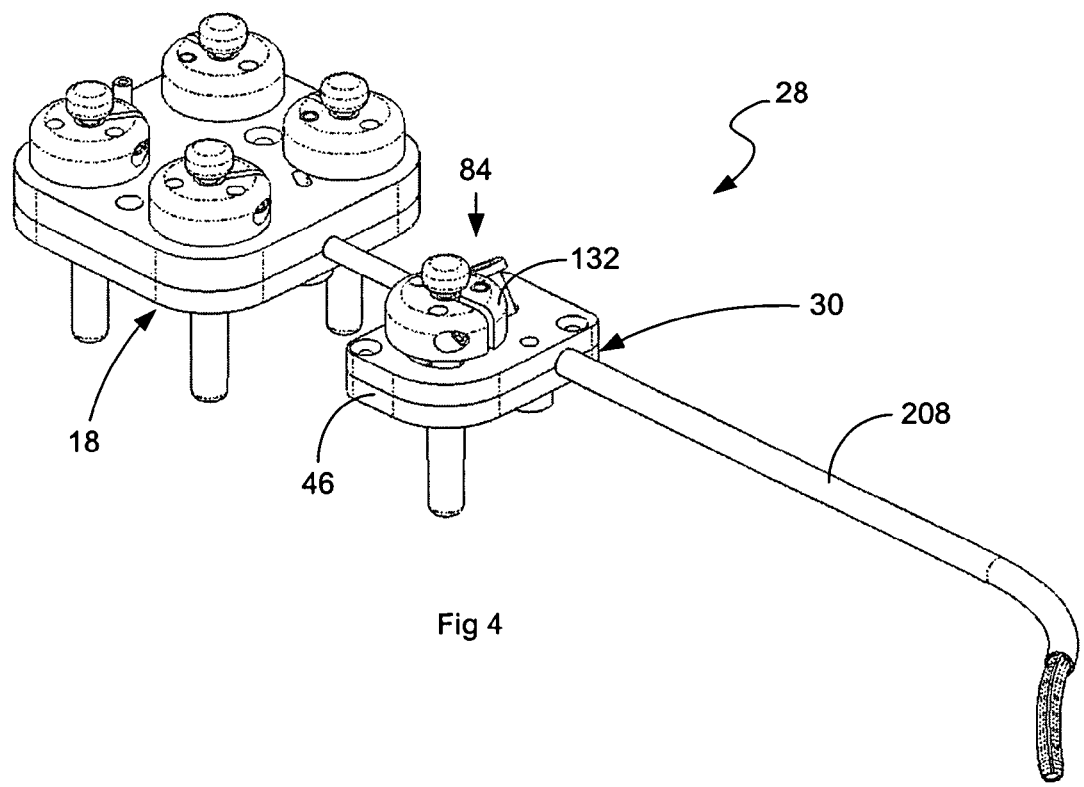
FIG. 4 is a perspective view of a coaxial guide/sheath catheter instrument used in either of the robotic surgical systems of FIGS. 1 and 2.

Referring now to FIG. 4, a set of two instruments (28) comprises the afore-described instrument (18), which can be referred to as a guide instrument (18) in this configuration, and a coaxially coupled and independently controllable sheath instrument (30). The sheath instrument (30) generally comprises a drivable assembly (84), which includes an instrument base (46) and a single control element interface assembly (132), a sheath catheter member (208), the proximal end of which is mounted within the instrument base (46), and a single control or tension element, such as a cable (not shown) extending within the sheath catheter member (208) and coupled to the interface assembly (132), such that operation of the interface assembly (132) bends the distal end of the sheath catheter member (208) in one direction.

Further details discussing the structure of the guide catheter member (90) and sheath catheter member (208) and the routing of control elements therein are disclosed in U.S. provisional patent application Ser. Nos. 60/677,580 and 60/678,097, which have previously been incorporated herein by reference.

From a functional perspective, in most embodiments the sheath instrument (30) need not be as driveable or controllable as the associated guide instrument (18), because the sheath instrument (30) is generally used to contribute to the remote tissue access schema by providing a conduit for the guide instrument (18), and to generally point the guide catheter member (90) in the correct direction. Such movement is controlled by rolling the sheath catheter member (208) relative to the patient and bending the sheath catheter member (208) in one or more directions with the control element.

Figure 5:
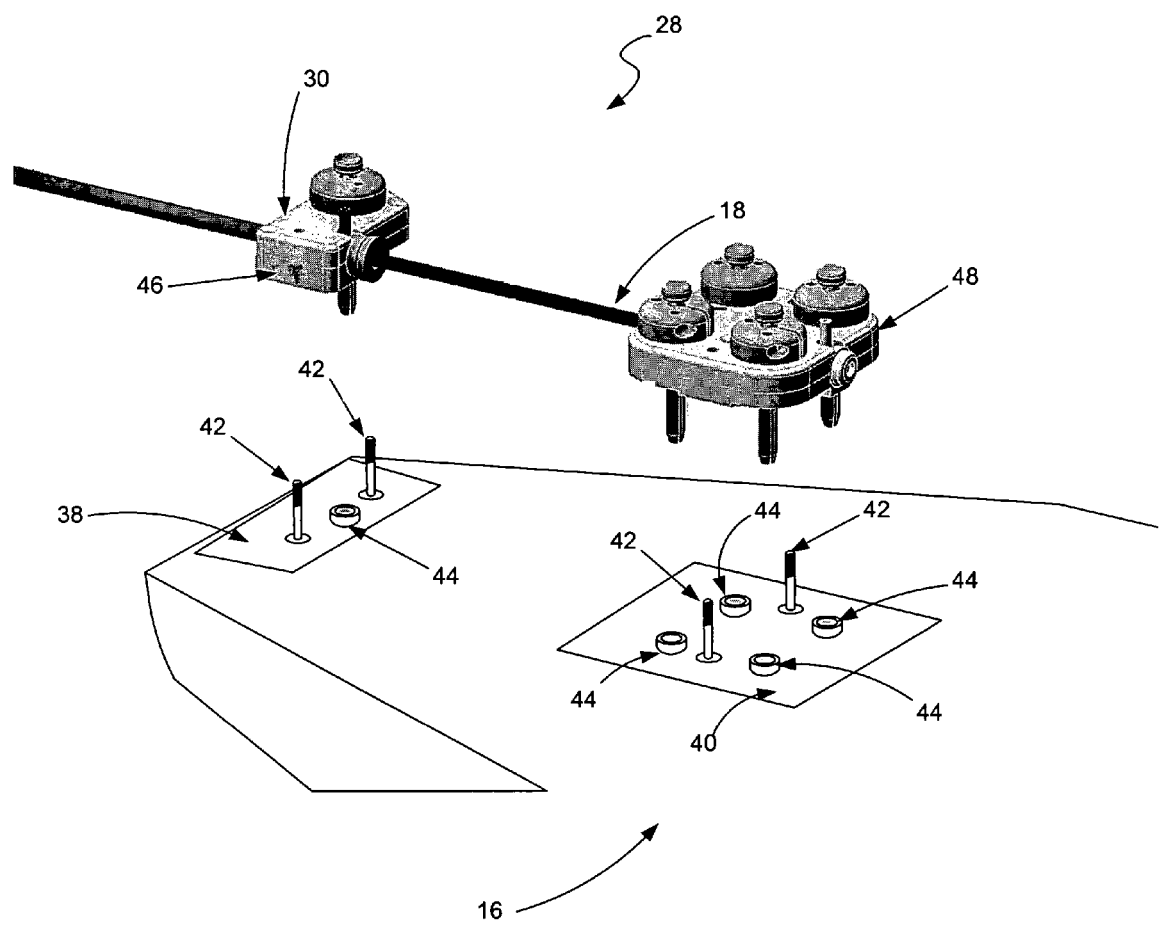
FIG. 5 is a perspective view of the coaxial guide/sheath catheter instrument of FIG. 4 and a portion of an instrument driver on which the catheter instrument is to be mounted.

Referring to FIG. 5, the set of instruments (28) is depicted adjacent an instrument driver (16) to illustrate an exemplary mounting scheme. The sheath instrument (30) may be coupled to the depicted instrument driver (16) at a sheath instrument interface surface (38) by aligning and sliding holes (not shown) of the sheath instrument base (46) over pins (42) extending upward from the interface surface (38). The drivable assembly (84) of the sheath instrument (30) conveniently mates with an interface socket (44) of the driver (16) once the sheath instrument base (46) is mounted to the instrument driver (16). Similarly, and preferably simultaneously, the guide instrument (18) may be coupled to the instrument driver (16) at a guide instrument interface surface (40) by aligning and sliding holes (not shown) of the guide instrument base (48) over mounting pins (42) extending upward from the interface surface (40). The drivable assemblies (82) of the guide instrument (18) conveniently mate with corresponding interface sockets (44) of the driver (16) once the guide instrument (18) is mounted to the instrument driver (16). As will be described in further detail, the interface surface (40) takes the form of a movable carriage on which the guide instrument base (48) will ride.

As will be appreciated, further steps may be required to lock the instruments (18, 30) into place upon the instrument driver (16). In one embodiment, the instruments (18, 30) are provided for a medical procedure in sterile packaging, while the instrument driver (16) is not necessarily sterile. In accordance with conventional sterile medical procedure, the non-sterile instrument driver (16) must be isolated from the patient by a sterile barrier of some type. Further details on the mounting of the instruments (28) to the instrument driver (16) and the use of sterile drapes are disclosed in U.S. provisional patent application Ser. Nos. 60/677,580 and 60/678,097, which have previously been incorporated herein by reference.

It can be appreciated from the above-described mounting scheme that the driving mechanisms of the instrument driver (16) mate directly with the drivable assemblies of the respective instruments (18), (30), thereby obviating the need to utilize intervening coupling devices that may otherwise adversely affect the desired accuracy in the predicted movement of the catheter deflections, e.g., due to unpredictable flexing and bending in the intervening coupling devices. It can also be appreciated that the above-described mounting scheme allows a user to rapidly exchange the instruments (18), (30), which are typically used only one time and thus disposable.

Figure 6:
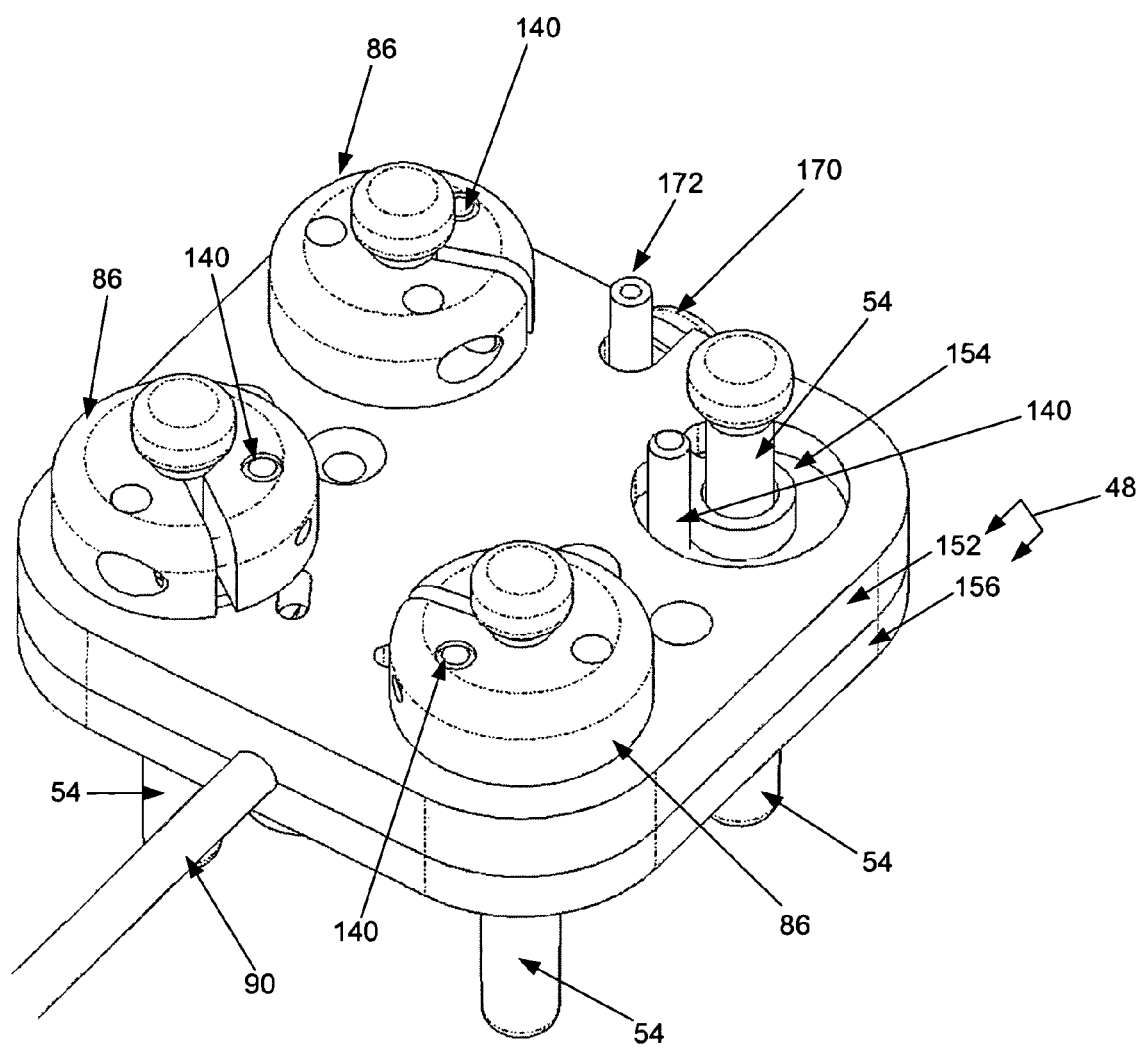
FIG. 6 is a partially disassembled perspective view of a proximal drivable assembly of the catheter instrument of FIG. 3.
Figure 7:
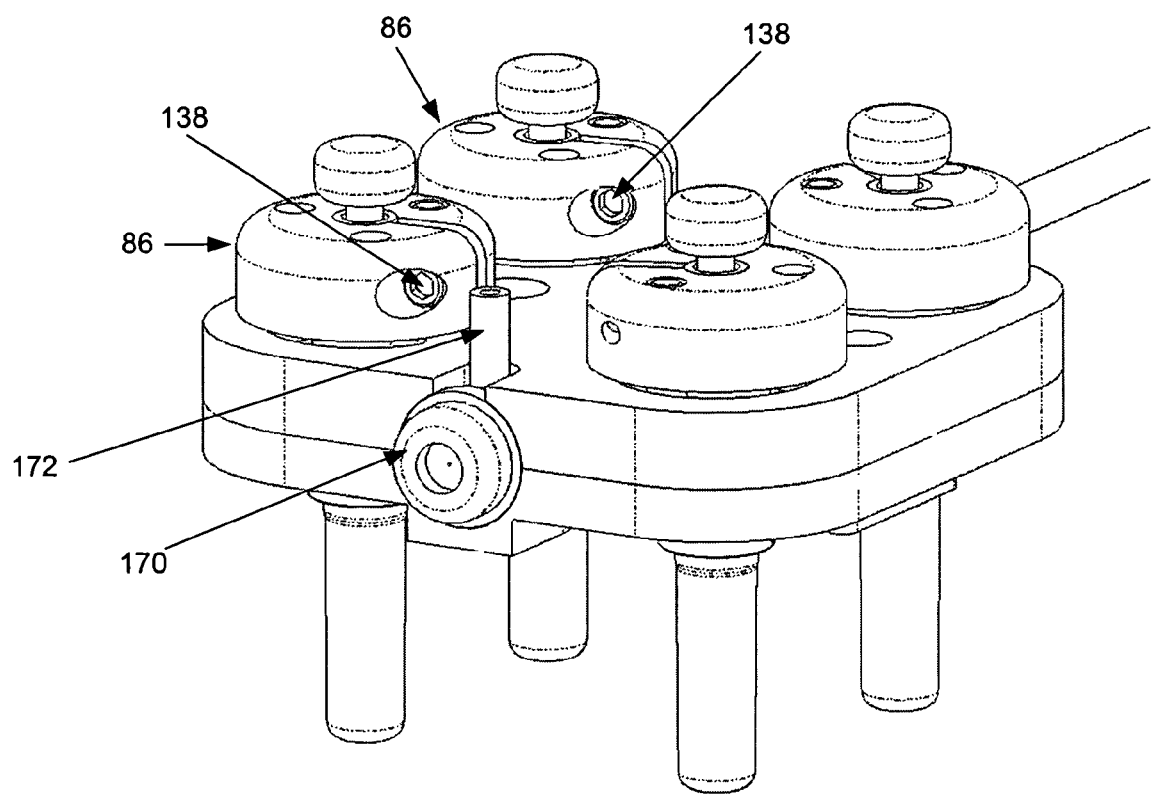
FIG. 7 is another perspective view of the proximal drivable assembly of FIG. 6.
Figure 8:
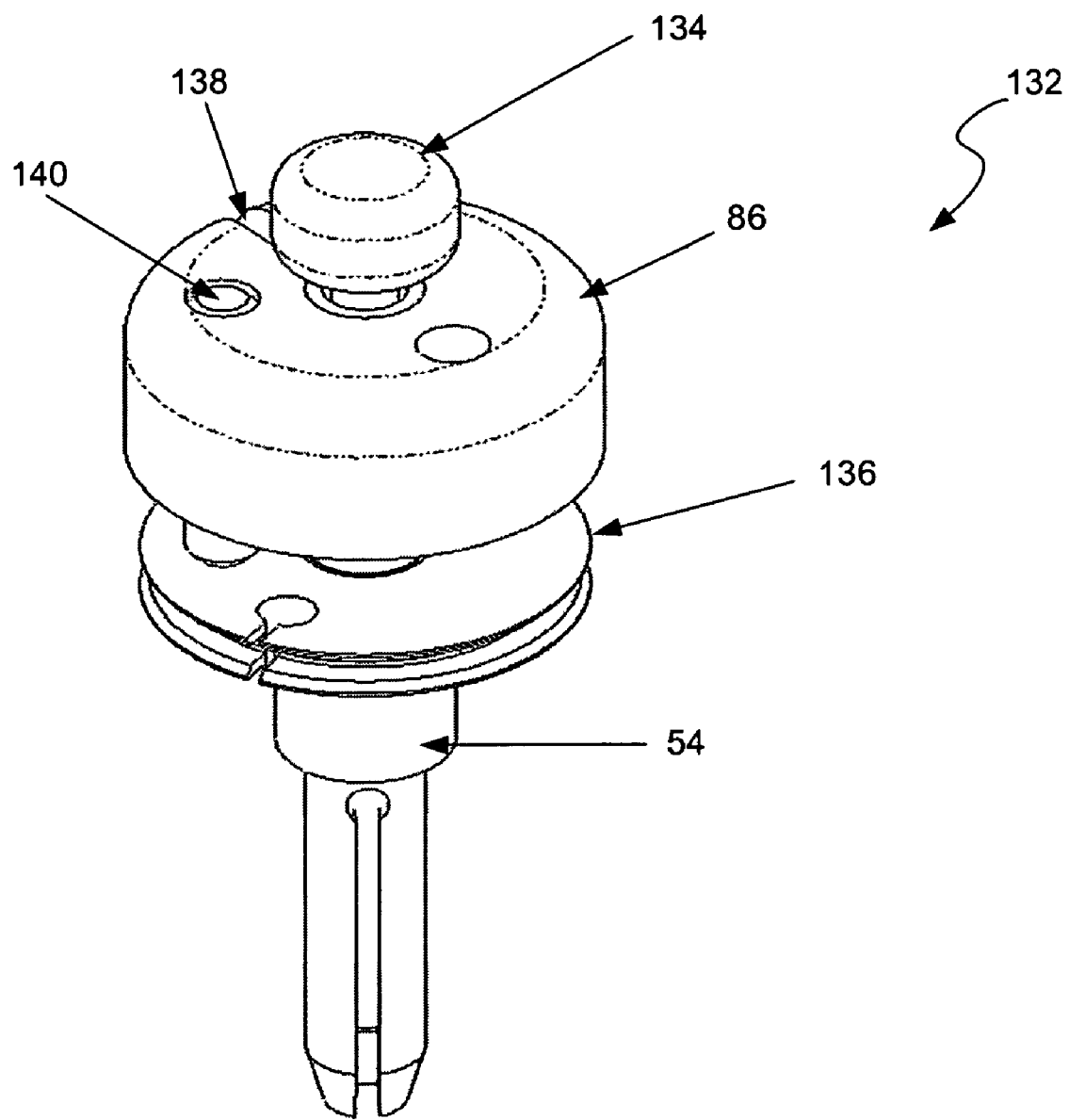
FIG. 8 is a perspective view of one control element interface assembly used in the proximal drivable assembly of FIG. 6.
Figure 9:
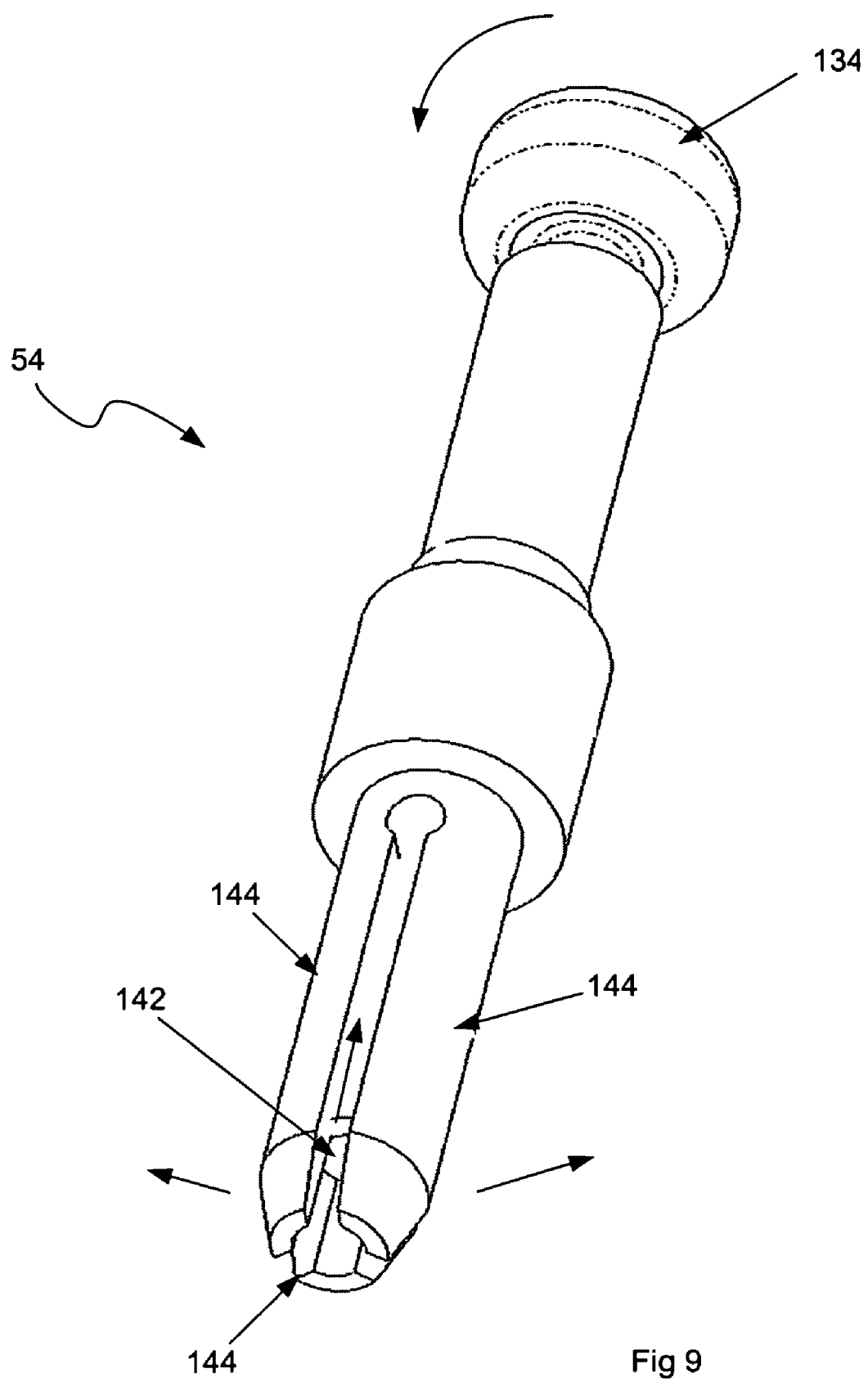
FIG. 9 is a partially disassembled perspective view of the control element interface assembly of FIG. 8.

FIGS. 6-15 depict certain aspects of the drivable assembly (82) of the guide instrument (18). Referring specifically to FIGS. 6 and 7, the guide instrument base (48) of the drivable assembly (82) generally comprises a top portion (152) and bottom portion (156), which are interfaced together to house the four control element interface assemblies (132), catheter member (90), a seal (170), and a purging port (172). The seal (170) preferably comprises a silicon rubber seal configured to accommodate insertion of working members or instruments, such as, e.g., relatively small profile guidewires (e.g., in the range of 0.035" diameter), or relatively larger profile catheters (e.g., of up to 7 French or even larger). The purging port (172) may be utilized to purge the guide catheter member (90), or circulate fluids therein As best shown in FIGS. 8 and 9, each control element interface assembly (132) comprises an axel (54), a control element pulley (136), a manual adjustment knob (86), and a drive engagement knob (134). The pulley (136) is configured to be rotated one way to spool, and thus proximal displace, a respective control element, thereby deflecting the distal end of the catheter member (90) in the predetermined direction dictated by the proximally displaced control element, and to be rotated the opposite way to unspool, and thus distally displace, the control element, thereby allowing the distal end of the catheter member (90) to deflect in another direction dictated by another control element interface assembly (132).

The manual adjustment knob (86) is configured to facilitate manual adjustment of control element tensions during setup of the instrument (18) upon the instrument driver (16). It is held in place against the axel (54) with a clamp screw (138), and houses a range of motion limitation pin (140), which limits the range of motion of the axel (54) subsequent to setup and tightening of the clamp screw (138). The drive engagement knob (134) may take a shape similar to a screw with a long threaded portion configured to extend through the axel (54) to engage a tapered nut (142), as shown. Twisting of the drive engagement knob (134) causes the tapered nut (142) to urge the teeth (144) of the axel outward, thereby engaging whatever structures surround the lower portion of the axel (54), including but not limited to an instrument driver interface socket (44).

Figure 10:
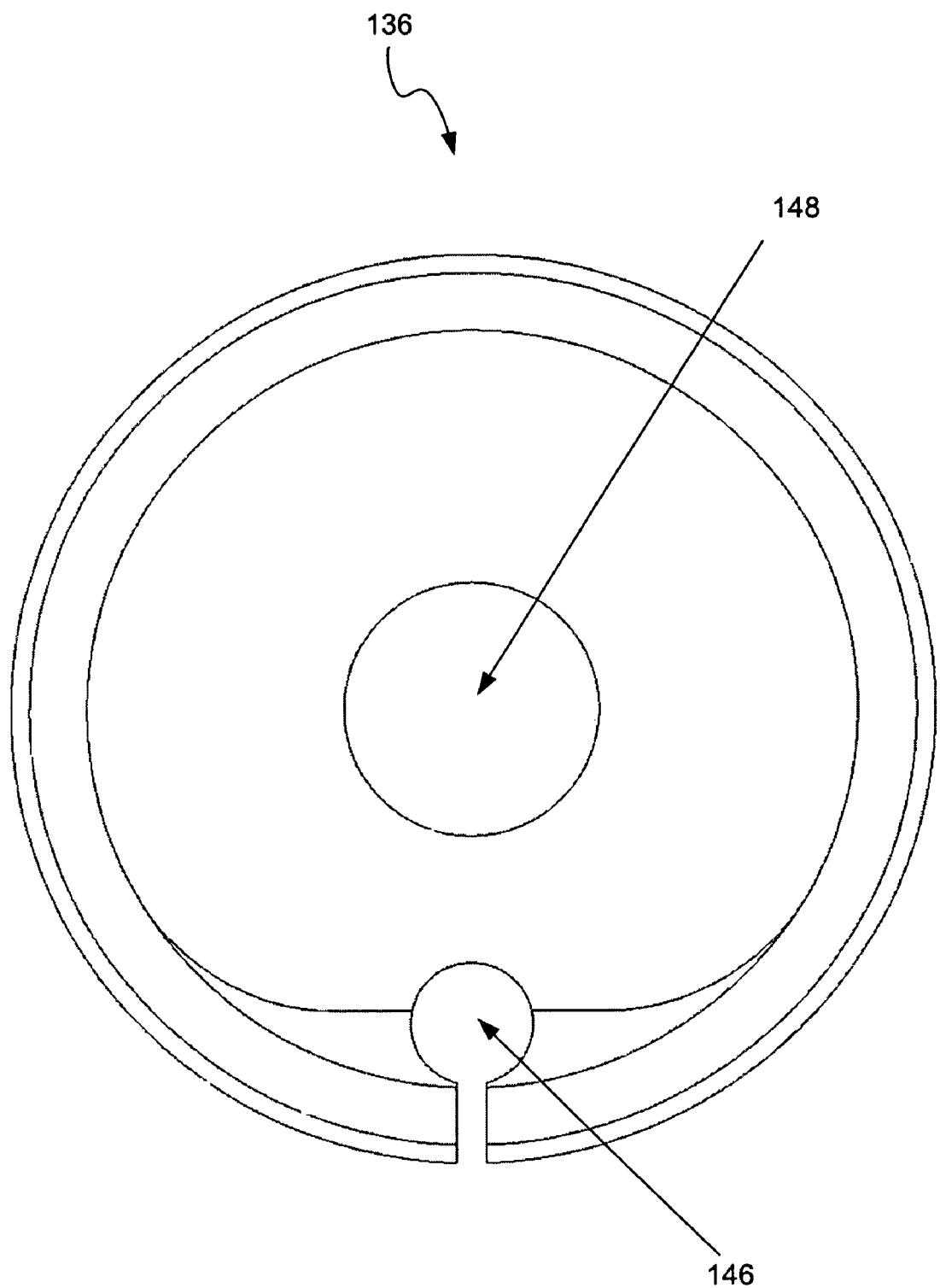
FIG. 10 is a top view of a pulley used in the control element interface assembly of FIG. 8.
Figure 11:
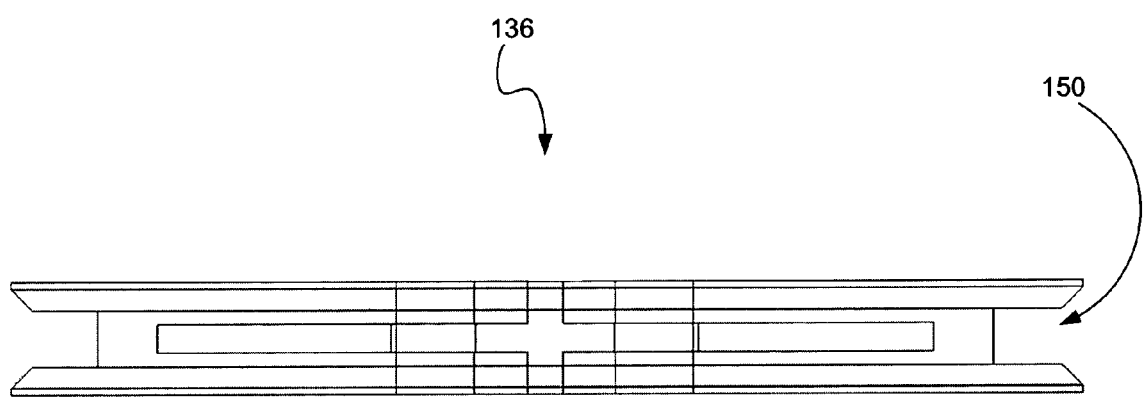
FIG. 11 is a profile view of the pulley of FIG. 10.
Figure 12:
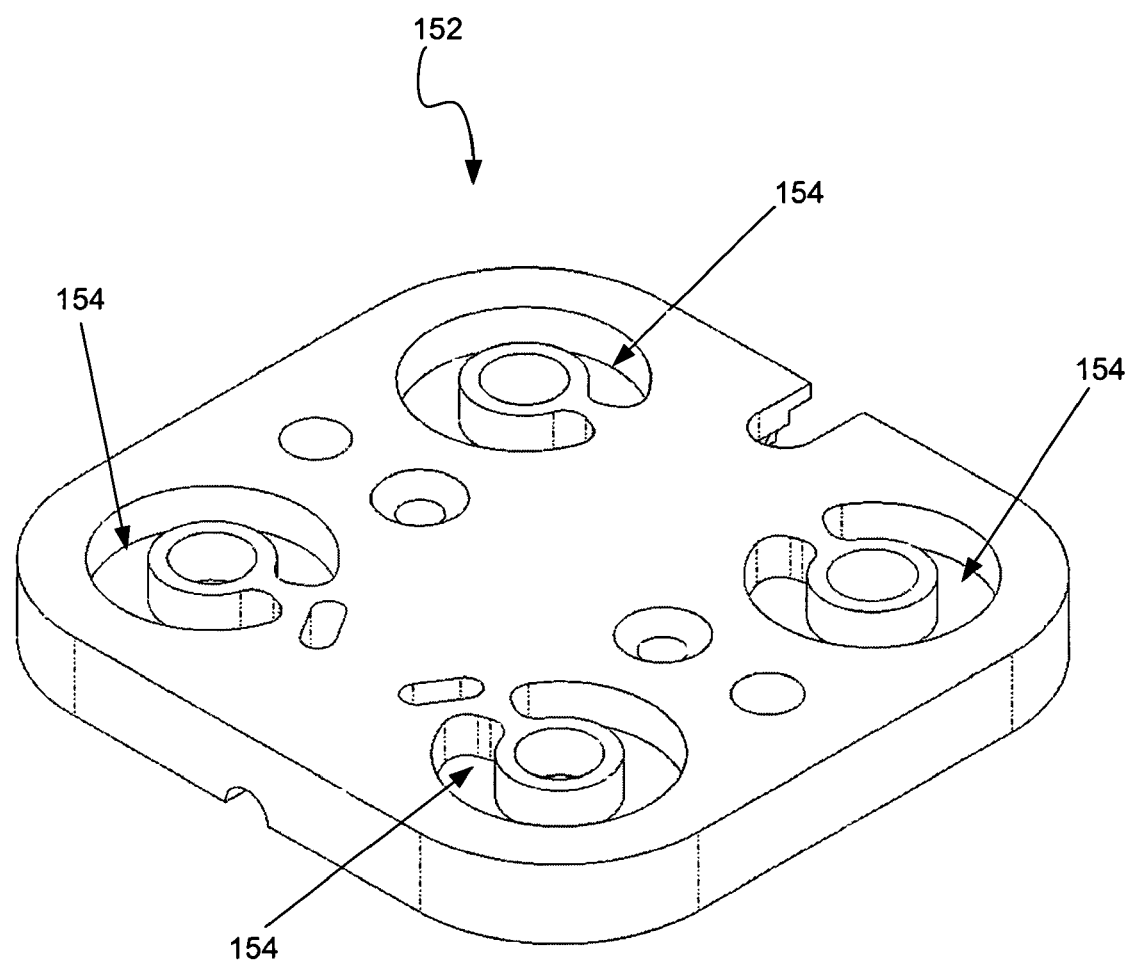
FIG. 12 is a top perspective view of a top base portion used in the proximal drivable assembly of FIG. 6.

Referring to FIGS. 9 and 10, the control element pulley (136) comprises a central hole (148) sized for a press fit upon the axel (54), and a control element termination engagement slot (146) configured to capture a control element terminator, such as a lead or steel cable terminator, that is pushed into the slot before a control element is wound around the pulley (136) during manufacture or rebuilding. As illustrated in FIG. 10, the pulley (136) preferably has a flanged shape (150) to facilitate winding and positional maintenance of a control element. The rotation of the pulleys (136) are limited to a predetermined range. In particular, the previously described motion limitation pins (140) interface with slots (154) formed in the top portion (152) of the guide instrument base (48) (best shown in FIG. 12).

Figure 13:
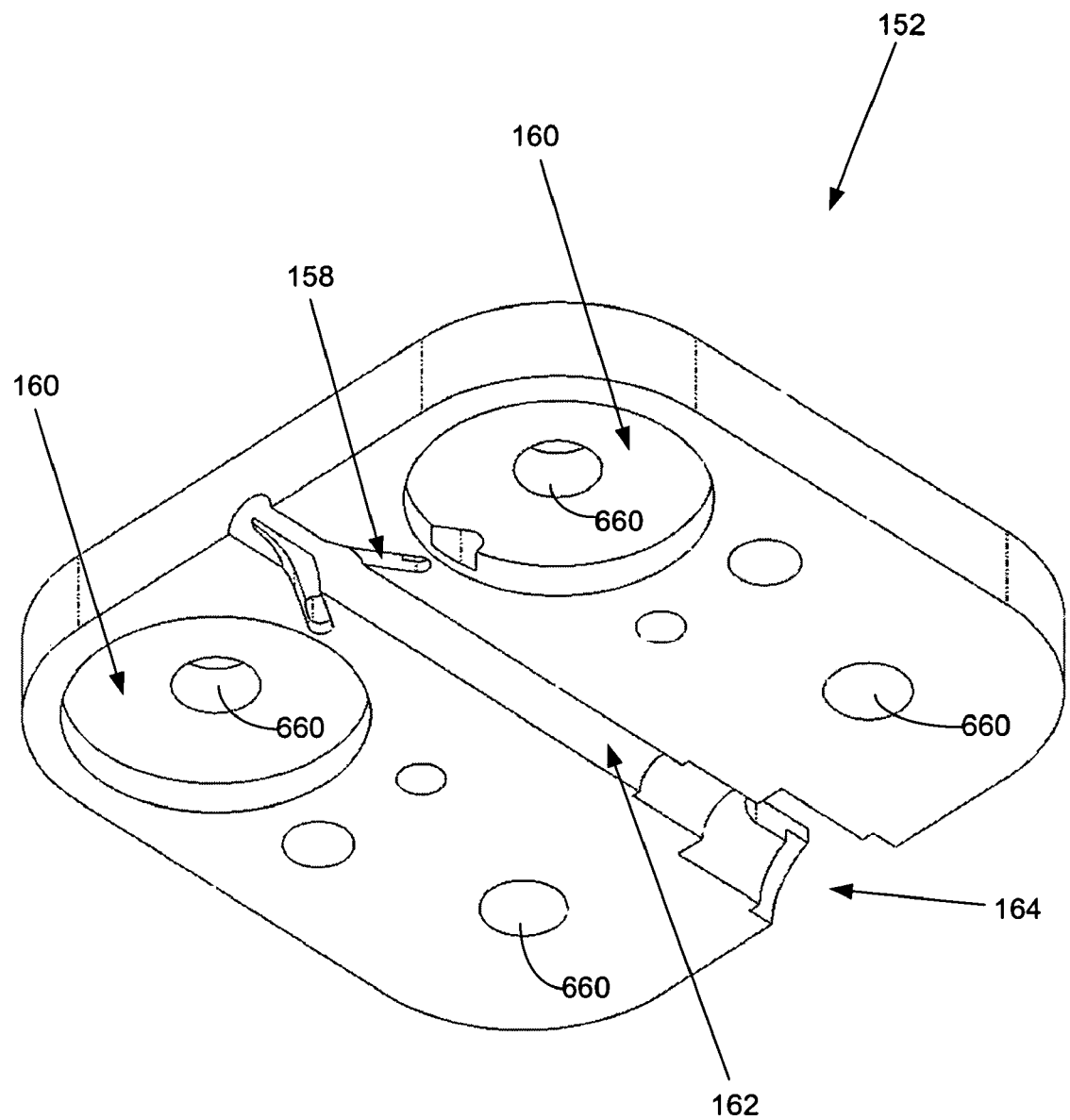
FIG. 13 is a bottom perspective view of the top base portion of FIG. 12.
Figure 14:
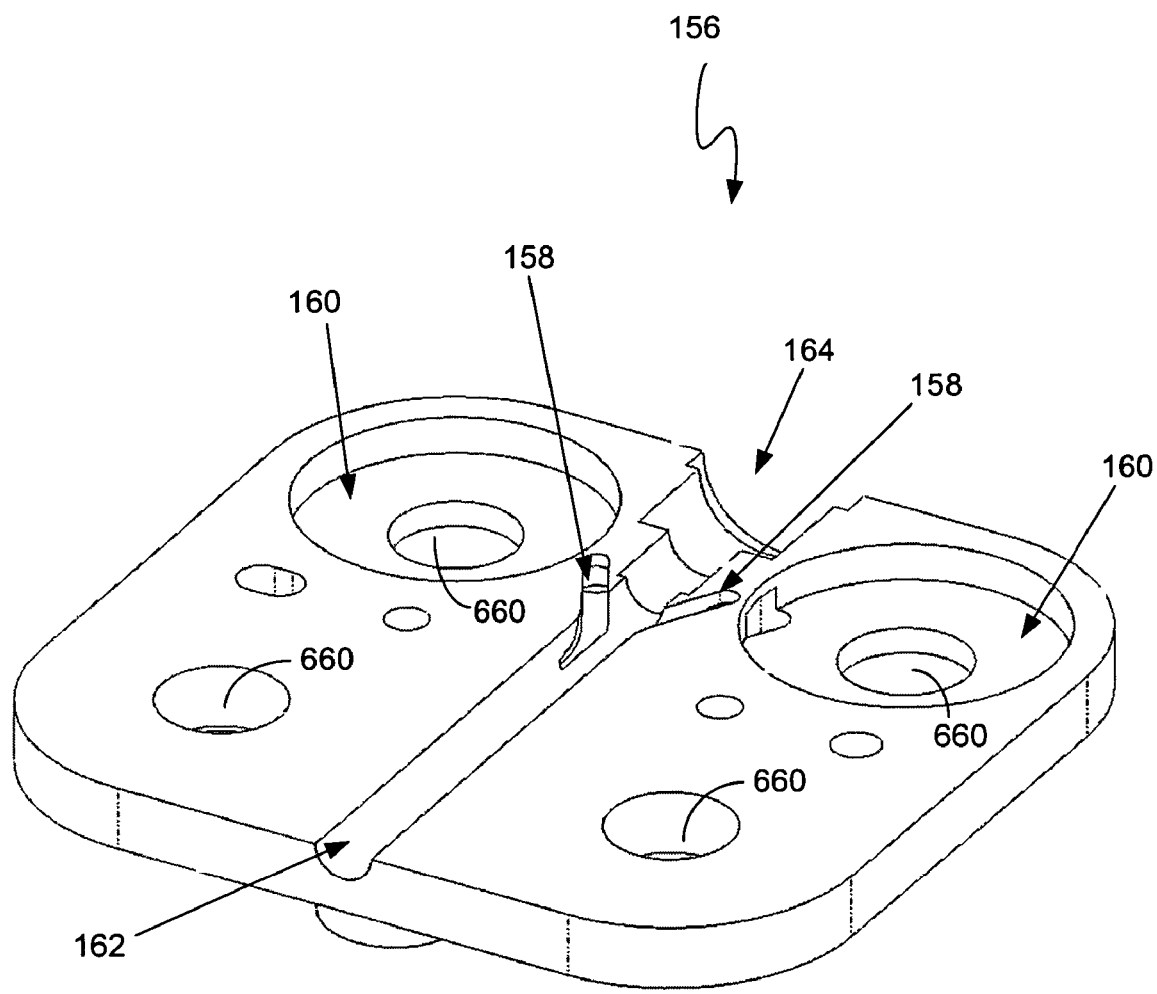
FIG. 14 is a top perspective view of a bottom base portion used in the proximal drivable assembly of FIG. 6.

As illustrated in FIG. 13, the top portion (152) also comprises two pulley recesses (160) for accommodating two of the four pulleys (not shown), and associated control element splay tracks (158) for guiding control elements (not shown) from apertures in the guide catheter member (90) into the two pulleys. Referring to FIG. 14, the bottom portion (156) includes two additional pulley recesses (160) for accommodating the remaining two of the four pulleys (not shown), and associated control element splay tracks (158) for guiding control elements (not shown) from apertures in the guide catheter member (90) into the remaining two pulleys. Each of the top portion (152) and bottom portion (156) also comprises four axel interface holes (660) for accommodating the axels (54) of the corresponding control element interface assemblies (132).

Figure 15:
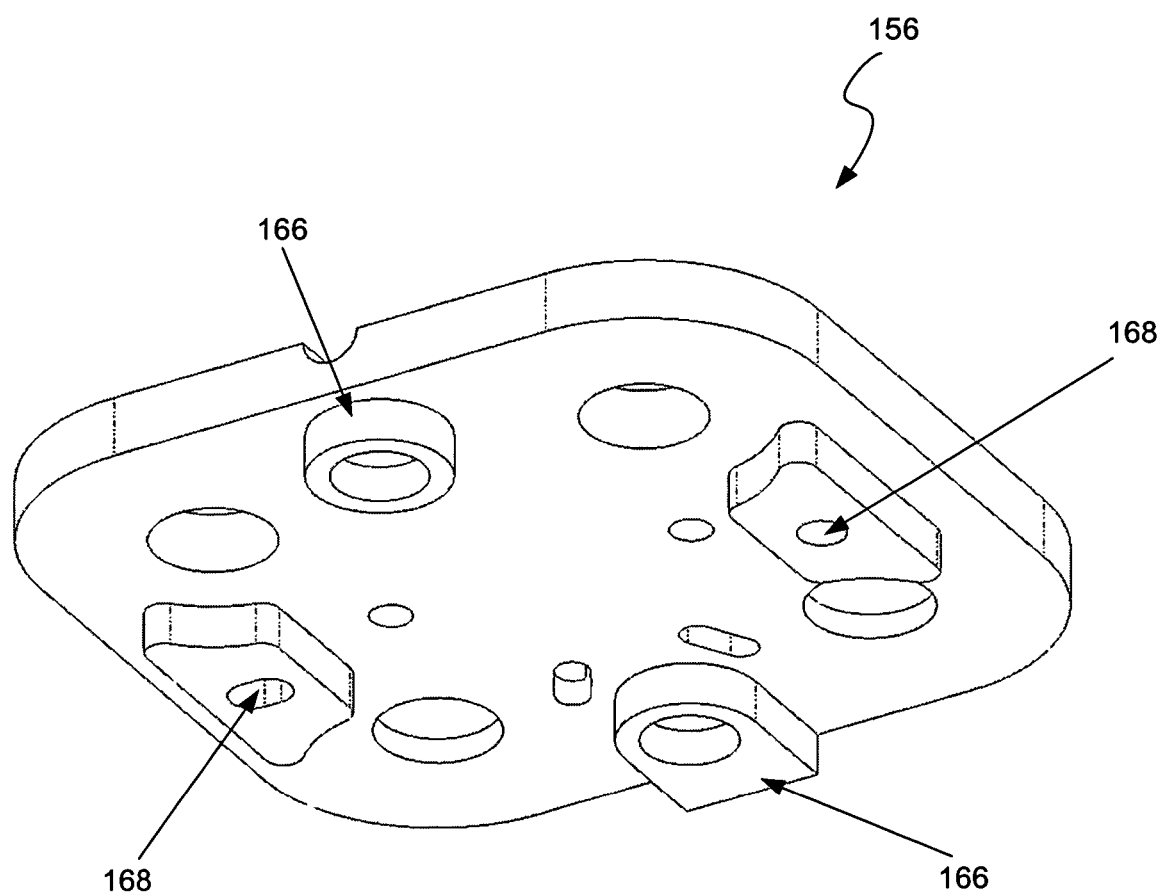
FIG. 15 is a bottom perspective view of the bottom base portion of FIG. 14.
Figure 16:
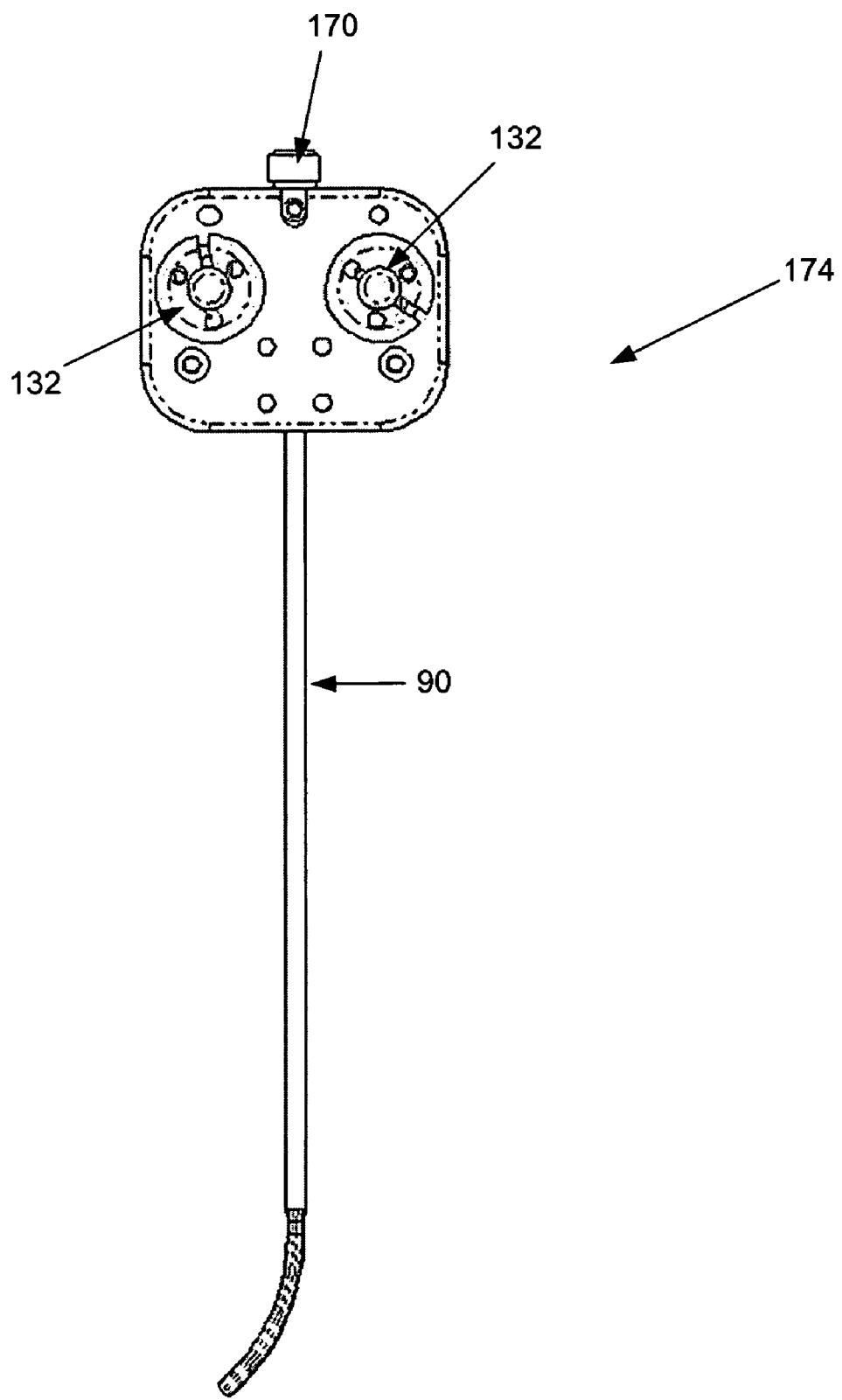
FIG. 16 is a top view of another catheter instrument that can be used in either of the robotic surgical systems of FIGS. 1 and 2.
Figure 17:
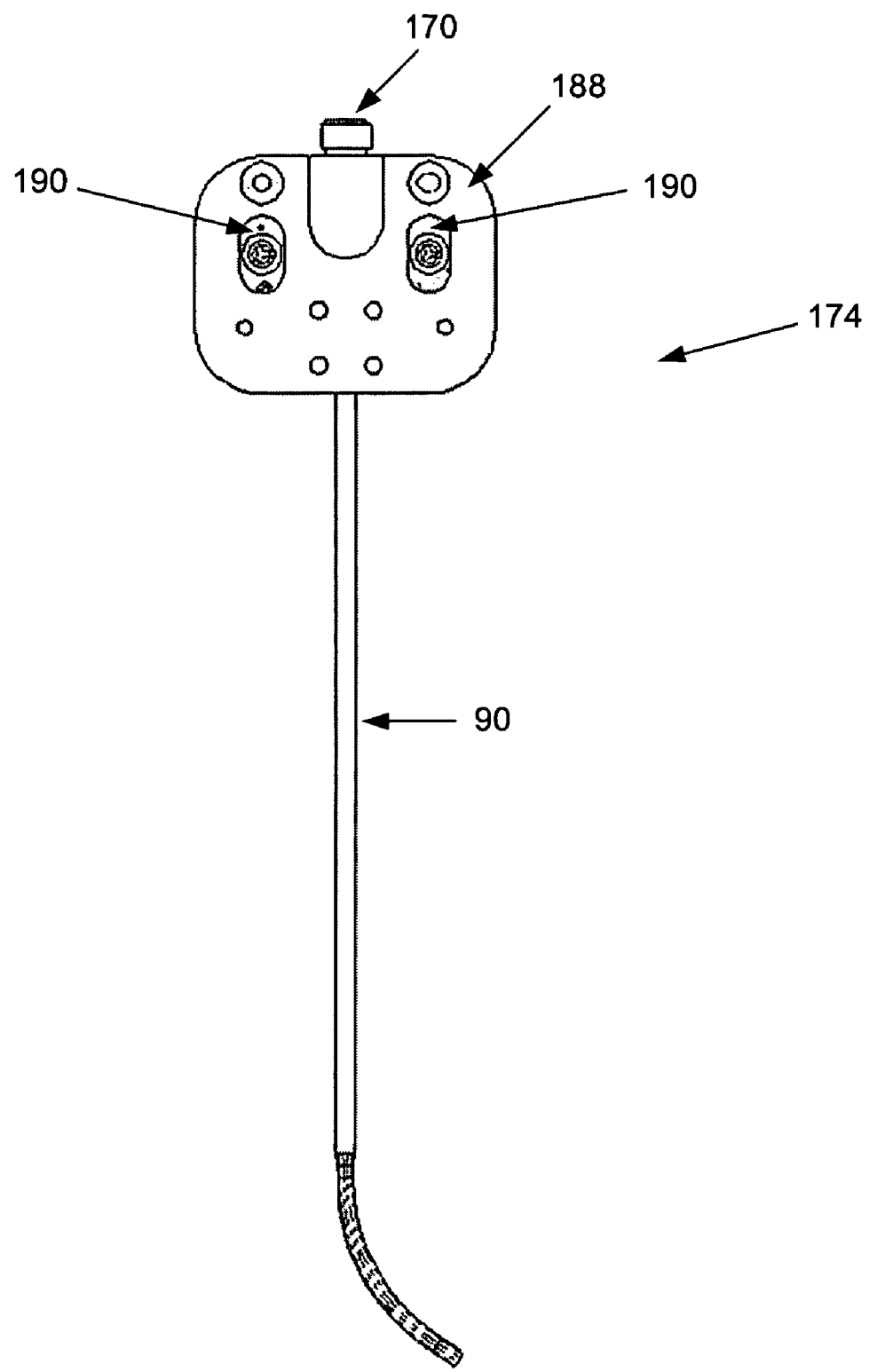
FIG. 17 is a partially dissembled top view of the catheter instrument of FIG. 16.

The top portion (152) and bottom portion (156) also have spatially corresponding catheter recesses (162) and seal recesses (164) for accommodating the proximal end of the guide catheter member (90). Thus, the top (152) and bottom (156) portions of the guide instrument base (48) can be "sandwiched" together to capture the proximal end of the guide catheter member (90) within these recesses. As illustrated in FIG. 15, the bottom surface of the bottom portion (156)

comprises magnets (166) to facilitate mounting of the guide instrument (18) on the instrument driver (16). The bottom portion (156) also has mounting pin interface holes (168) formed through it to accommodate mounting pins (42) (shown in FIG. 5) from the instrument driver (16). Further, the bottom portion (156) preferably has a generally asymmetric geometry to ensure that it will only fit the underlying instrument driver (16) snugly in one way.

Although the drivable assembly (82) of the guide instrument (18) comprises four control element interface assemblies (132) that control four corresponding control elements, drivable assemblies may include any number of control element interface assemblies (132) for controlling the same number of control elements depending on the application. For example, a drivable assembly (82) may include one, two, three, or more than four control element interface assemblies (132), depending on the desired number of control elements to be tensioned.

Referring to FIGS. 16-22, other embodiments of guide instruments are depicted having the respective capabilities to drive four control elements with only two control element interface assemblies. For ease in illustration, many of the same components are utilized in these embodiments. As will be appreciated by those skilled in the art, such component matching is by no means required to accomplish the described functions, and many alternative arrangements are possible within the scope of the inventions disclosed herein.

Figure 18:
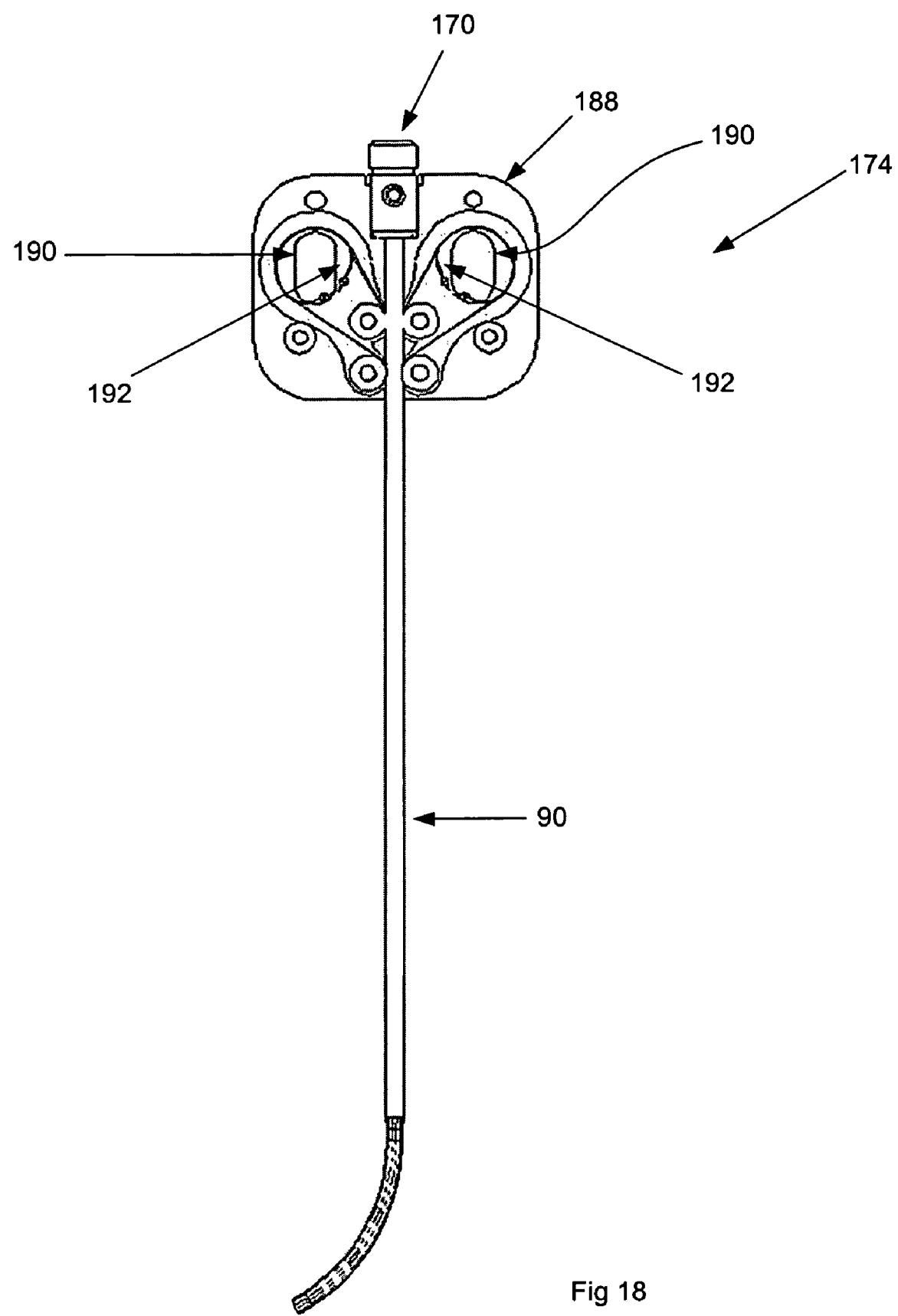
FIG. 18 is another partially disassembled top view of the catheter instrument of FIG. 16.
Figure 19:
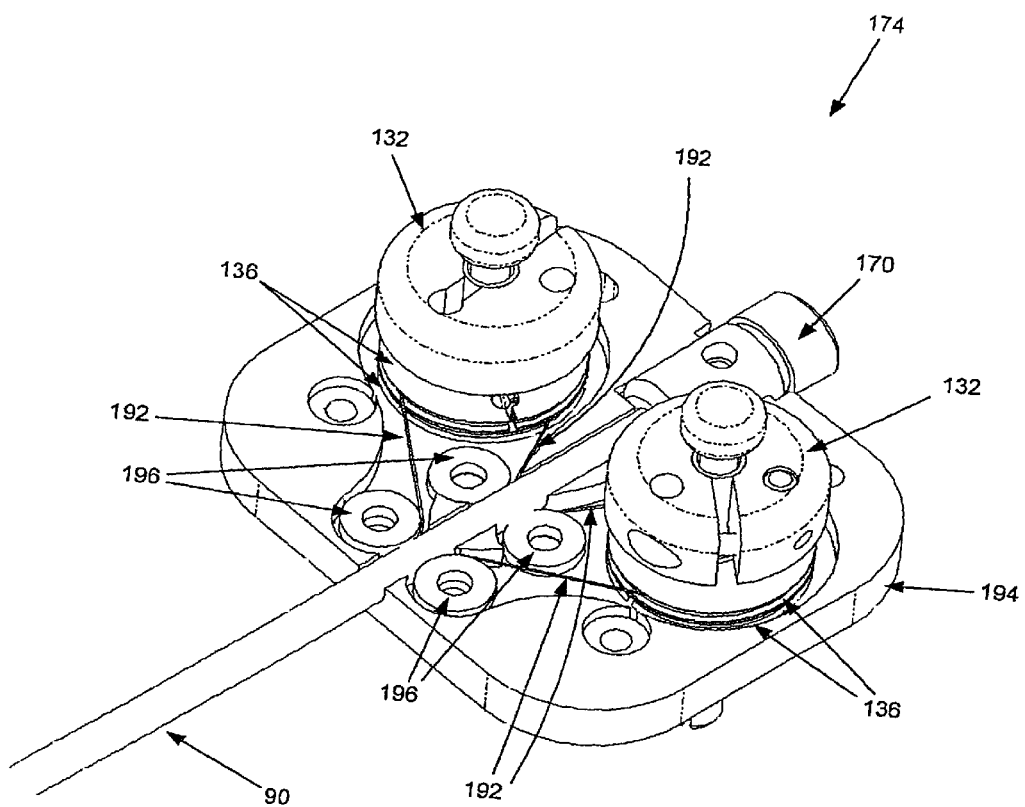
FIG. 19 is a partially disassembled perspective view of a proximal drivable assembly used in the catheter instrument of FIG. 16.
Figure 20:
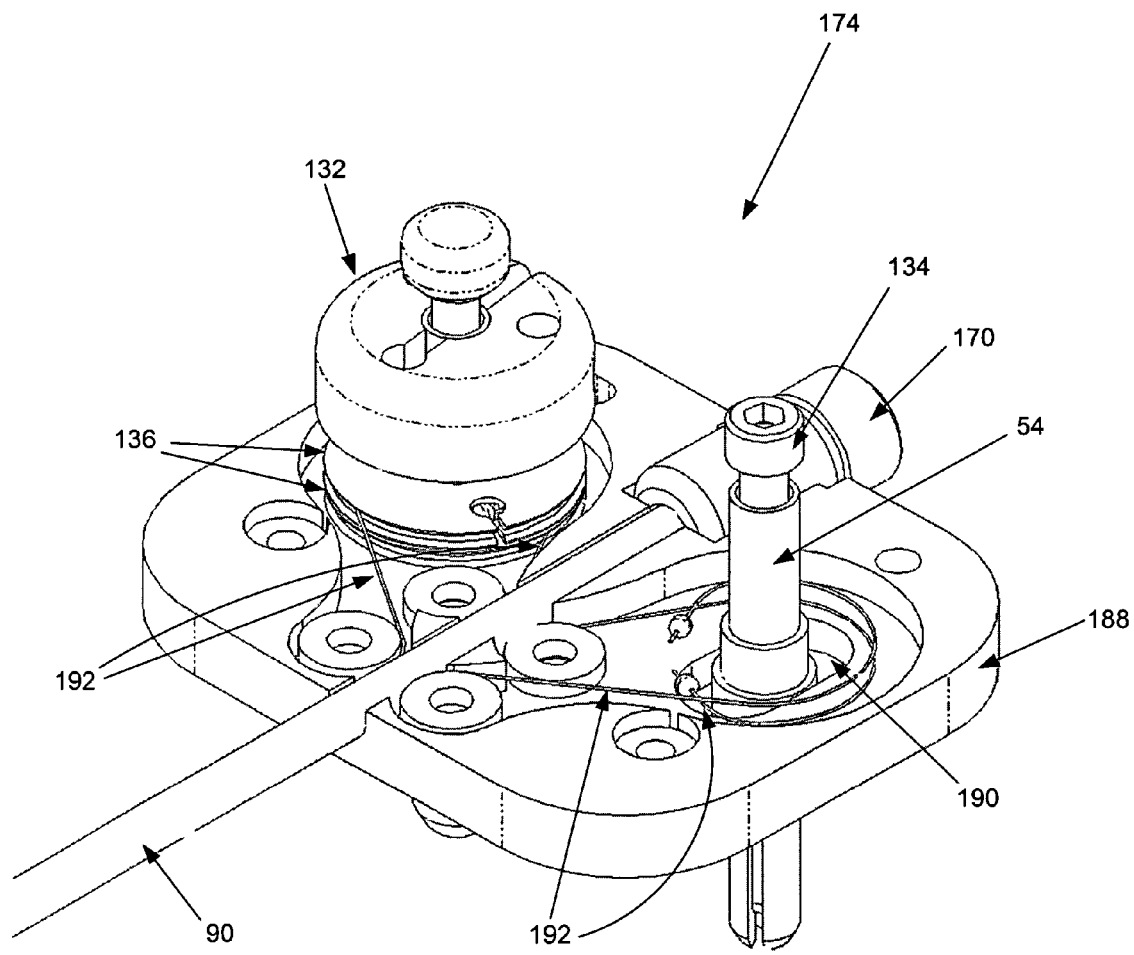
FIG. 20 is another partially disassembled perspective view of the proximal drivable assembly of FIG. 19.

Referring specifically to FIGS. 16-20, a guide instrument (174) has only two control element interface assemblies (132) configured to drive four control elements (192) (shown in FIG. 18). To this end, each control element interface assembly (132) comprises a stacked pair of pulleys (136) to accommodate a respective pair of control elements (192), as illustrated in FIGS. 19 and 20. It can be appreciated that rotation of the pair of pulleys (136) in one direction spools, and proximal displaces, one control element (192), while unspooling, and thus distally displacing, the other control element (192), thereby deflecting the distal end of the catheter member (90) in the predetermined direction dictated by the tensioned control element (192). Rotation of the pair of pulleys (136) in the opposite direction unspools, thus distally displacing, the previously proximal displaced control element (192), while spooling, and thus proximal displacing, the previously distally displaced control element (192), thereby deflecting the distal end of the catheter member (90) in the predetermined direction dictated by the newly tensioned control element (192).

The control element interface assemblies (132) are also configured to maintain a minimal amount of tension using fixed idler control element pathways (196) to align the control elements (192) with the sets of two pulleys (136) included within the respective control element interface assemblies (132). In this embodiment, tension may be maintained in the control elements (192), with pre-tensioning, or pre-stressing, to prevent control element slack. Tension is also maintained on the four control elements (192) using a slotted guide instrument base (188). In particular, the guide instrument base (188) forms slots (190) through which an instrument driver tensioning mechanism, which will be described in further detail below, may keep control elements (192) taut during operation of the instrument (174) by translating the respective control element interface assemblies (132) within the slots (190). Depending upon the amount of tensioning deflection within the slots (190), it may be desirable to remove the rotational range of motion limitation pin (not shown) from the manual adjustment knob (not shown) to prevent impingement of the pin, knob, and instrument base (188), as the control element interface assembly (132) is moved in the respective slot (190) relative to the rest of the instrument base (188). In the embodiment illustrated in FIG. 18, the slots (190) are rectilinear. However, in alternative embodiments, the slots (190) can have any shape, such as arcuate, that allows the respective control element interface assembly (132) to translate relative to the instrument base (188).

The use of slots (190) in which the respective control element interface assemblies (132) can translate also provides an addition means for deflecting the distal end of the catheter member (90). In particular, a control element interface assembly (132) can be proximally displaced in a respective slot (190), which without rotation of the control element interface assembly (132), tensions both control elements (192). However, while the control element interface assembly (132) is proximally translated within the slot (190), it is rotated in one direction to unspool one of the control elements (192) to facilitate its axial displacement in the distal direction as the other control element (192) is axially displaced in the proximal direction by the proximal translation of the control element interface assembly (132) and spooling of the control element (192) onto the control element interface assembly (132). As a result, the distal end of the catheter member will be deflected in the predetermined direction dictated by the other control element (192).

Figure 21:
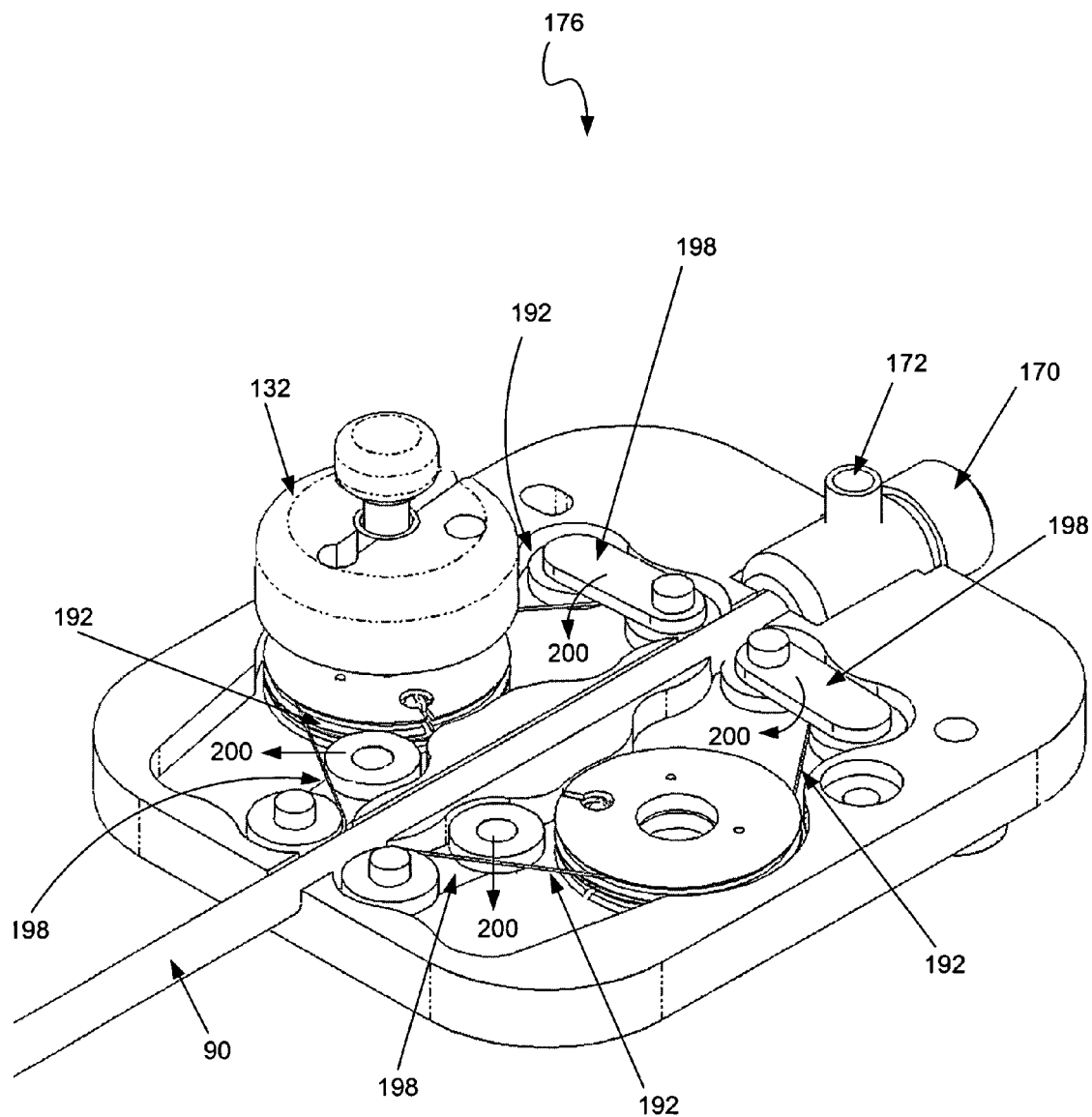
FIG. 21 is a partially disassembled perspective view of another proximal drivable assembly that can be used in the catheter instrument of FIG. 16.
Figure 22:
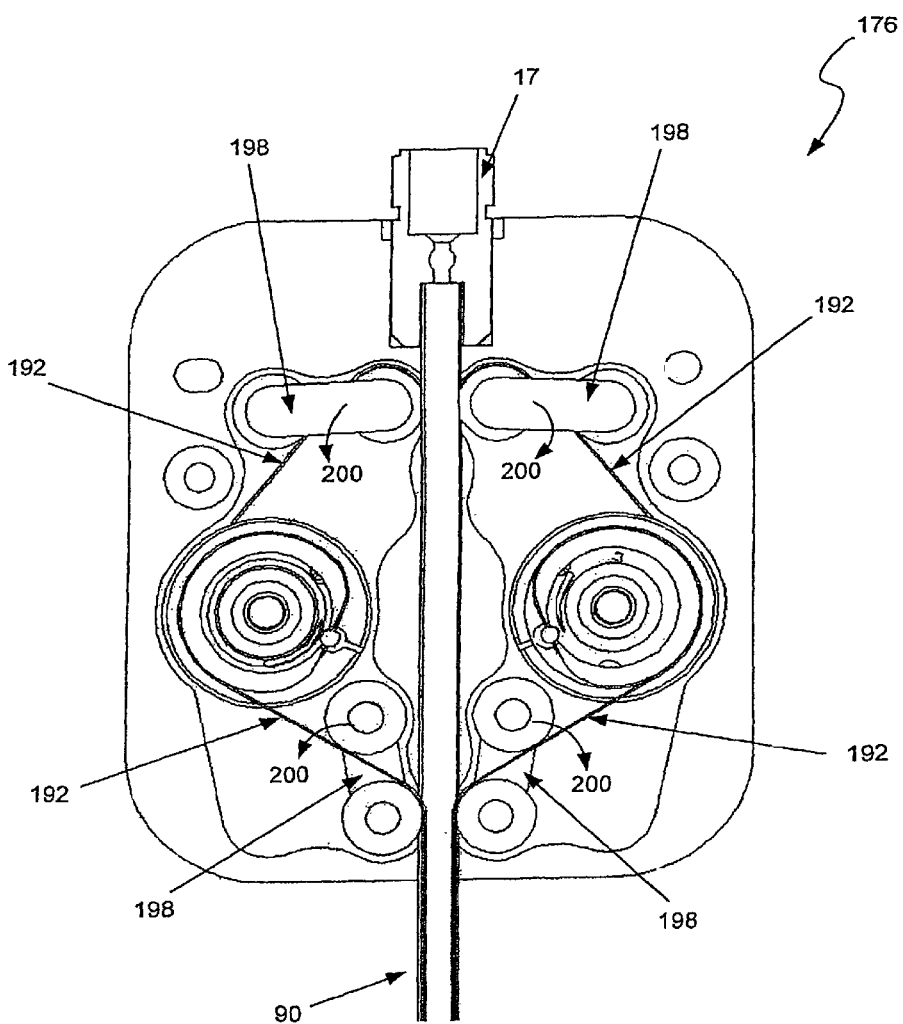
FIG. 22 is a partially disassembled top view of the proximal drivable assembly of FIG. 21.

Referring to FIGS. 21 and 22, a guide instrument (176) is similar to that illustrated in FIG. 19, with the exception that it comprises four spring-loaded idlers (198) to assist with tensioning each of the four control elements (192). Each of the control elements (192) passes through a spring loaded idler (198), which urges the control element (192) into tension by trying to rotate (200).

Figure 23:
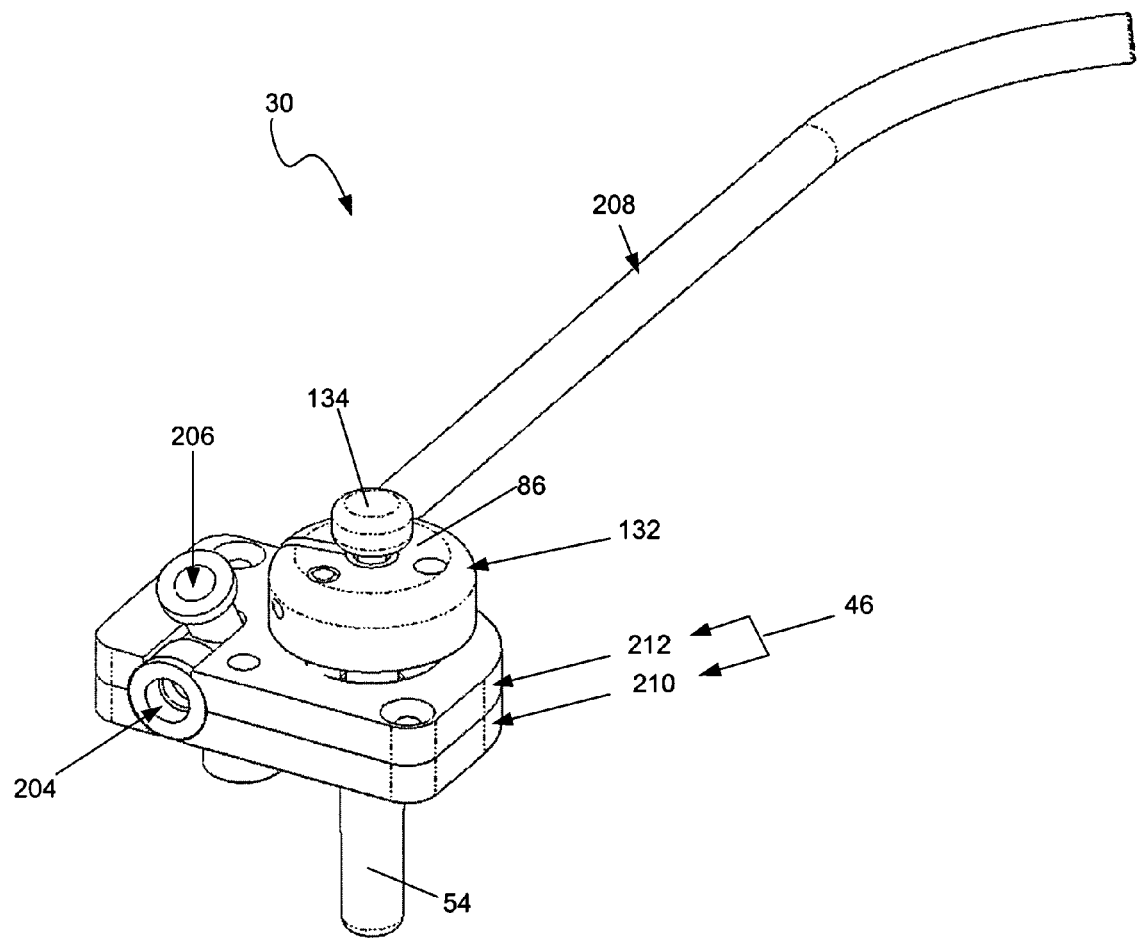
FIG. 23 is a perspective view of a proximal drivable assembly of the sheath instrument shown in FIG. 4.

FIGS. 23-26 depict certain aspects of the drivable assembly (132) of the sheath instrument (30). Referring specifically to FIG. 23, the sheath instrument base (46) of the drivable assembly (84) generally comprises a top portion (212) and bottom portion (210), which are interfaced together to house the single control element interface assembly (132), sheath catheter member (208), a seal (204), and a purging port (206). Like the previously described control element interface assemblies (132) of the guide instrument (18), the control element interface assembly (132) of the sheath instrument (30) comprises an axel (54), a control element pulley (not shown), a manual adjustment knob (86), and a drive engagement knob (134) that function in the same manner to control the corresponding control element extending through the sheath catheter member (208). The seal (204) is generally larger than the seal on the guide instrument (18) due to the larger diameters of elongate members that may be inserted into the sheath instrument (30) as part of a medical procedure. The purging port (206) may be utilized to purge the sheath catheter member (208), or circulate fluids therein.

Figure 24:
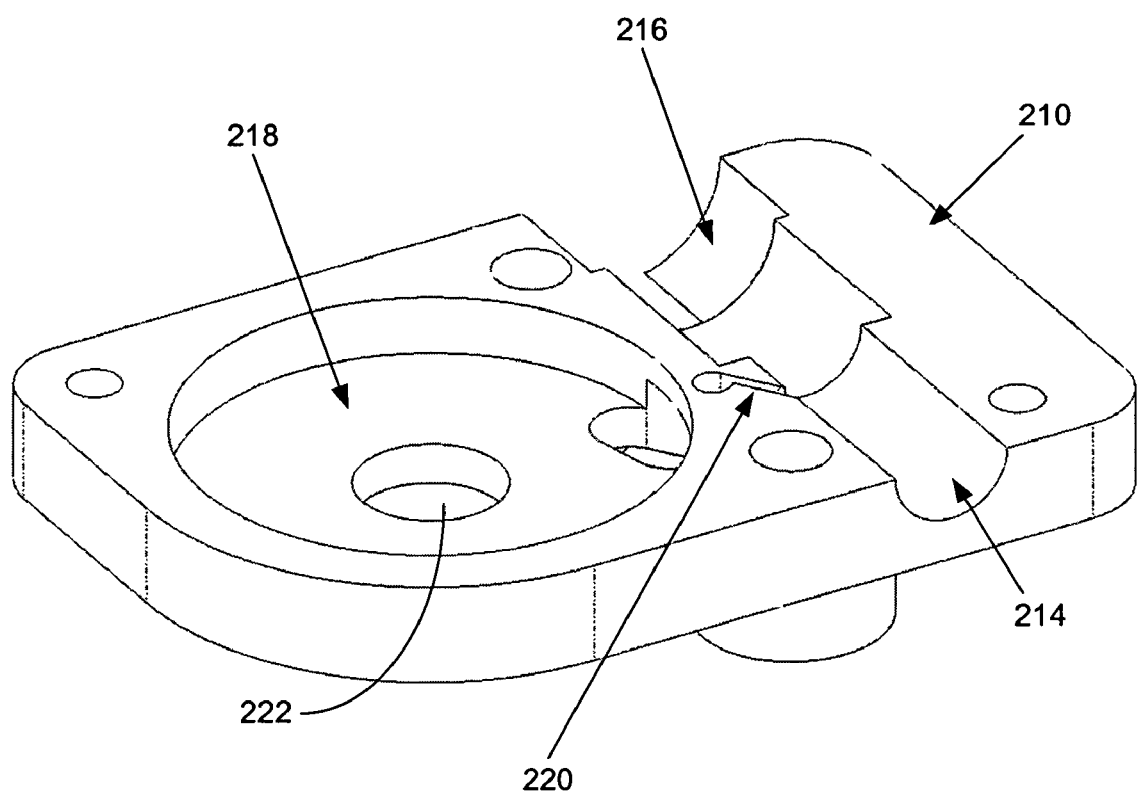
FIG. 24 is a top perspective view of a bottom base portion of the proximal drivable assembly of FIG. 23.
Figure 25:
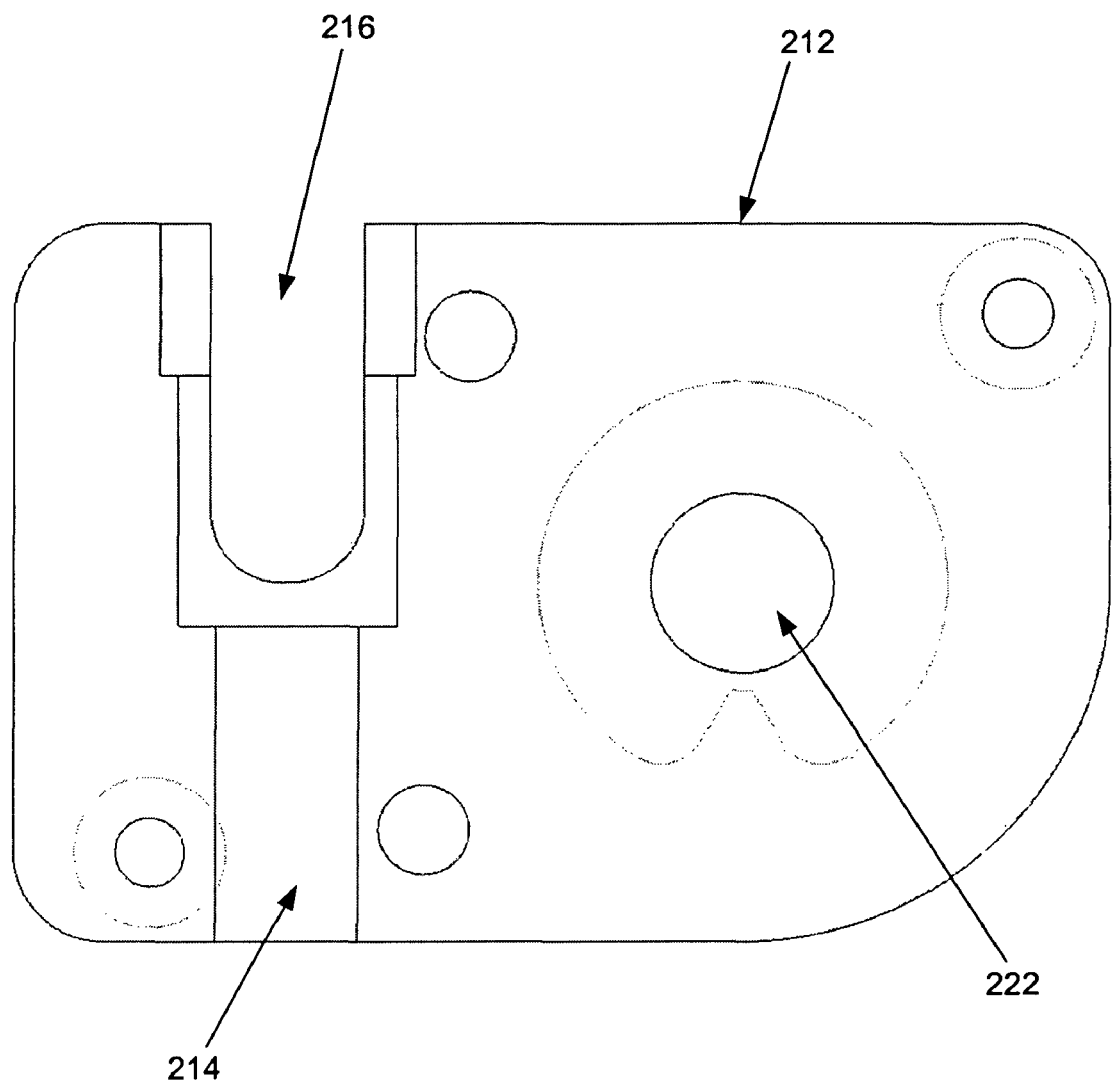
FIG. 25 is a bottom view of a top base portion of the proximal drivable assembly of FIG. 23.

As illustrated in FIG. 24, the bottom portion (210) comprises a pulley recess (218) for accommodating the single pulley (not shown), and an associated control element splay track (220) for guiding the control element (not shown) from an aperture in the sheath catheter member (208) into the pulley. Referring further to FIG. 25, each of the bottom portion (210) and top portion (212) also comprises an axel interface hole (222) for accommodating the axel (54) of the control element interface assembly 132. The bottom portion (210) and top portion (212) also have spatially corresponding catheter recesses (216) and seal recesses (214) for accommodating the proximal end of the sheath catheter member (208). Thus, the bottom (210) and top (212) portions of the sheath instrument base (46) can be "sandwiched" together to capture the proximal end of the sheath catheter member (208) within such recesses.

Figure 26:
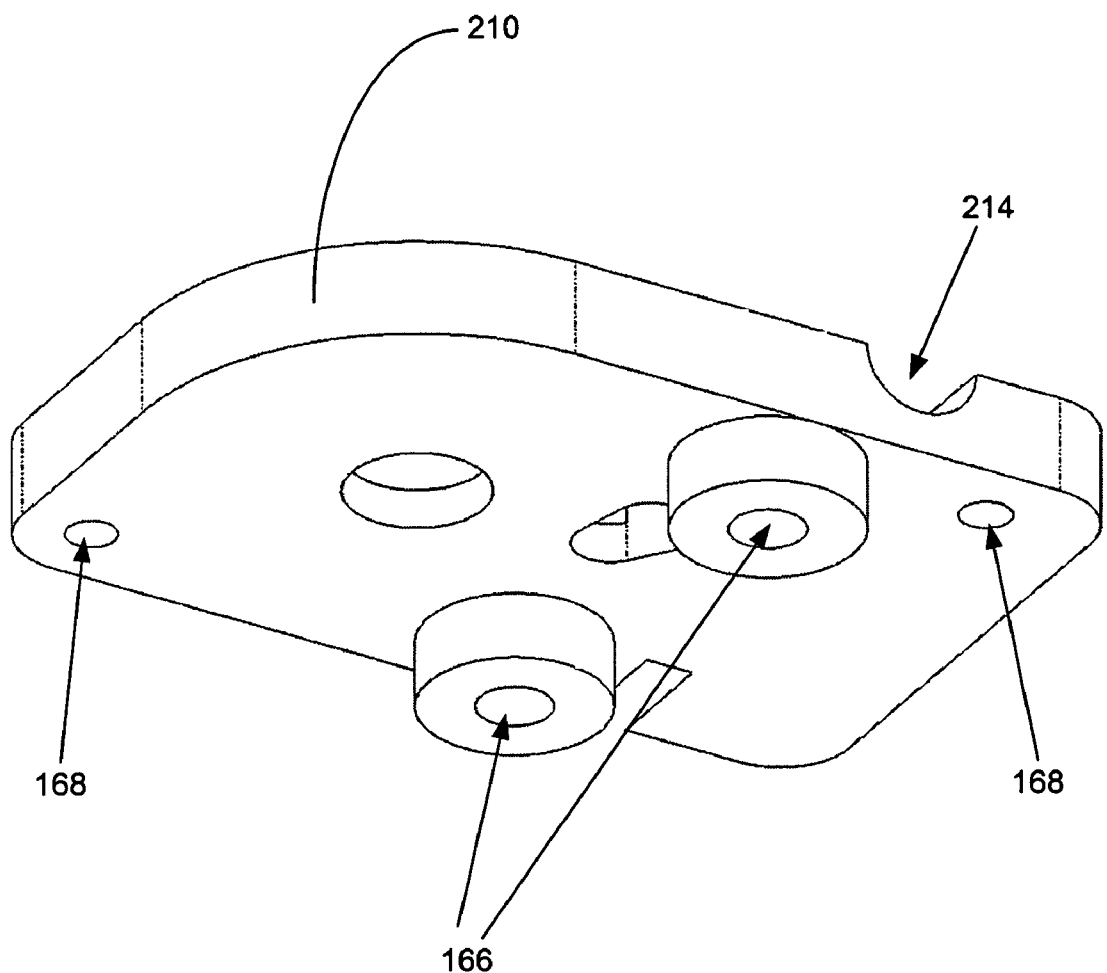
FIG. 26 is a bottom perspective view of the bottom base portion of FIG. 24.

As illustrated in FIG. 26, the bottom surface of the bottom portion (210) comprises magnets (166) to facilitate mounting of the sheath instrument (30) on the instrument driver (16). The bottom portion (210) also has mounting pin interface holes (168) formed through it to accommodate mounting pins (42) (shown in FIG. 5) from the instrument driver (16). Further, the bottom portion (156) preferably has a generally asymmetric geometry to ensure that it will only fit the underlying instrument driver (16) snugly in one way.

Referring to FIGS. 27-30, other embodiments of sheath instruments are depicted having the respective capabilities to drive two control elements with only one control element interface assembly. For ease in illustration, many of the same components are utilized in these embodiments. As will be appreciated by those skilled in the art, such component matching is by no means required to accomplish the described functions, and many alternative arrangements are possible within the scope of the inventions disclosed herein.

Figure 27:
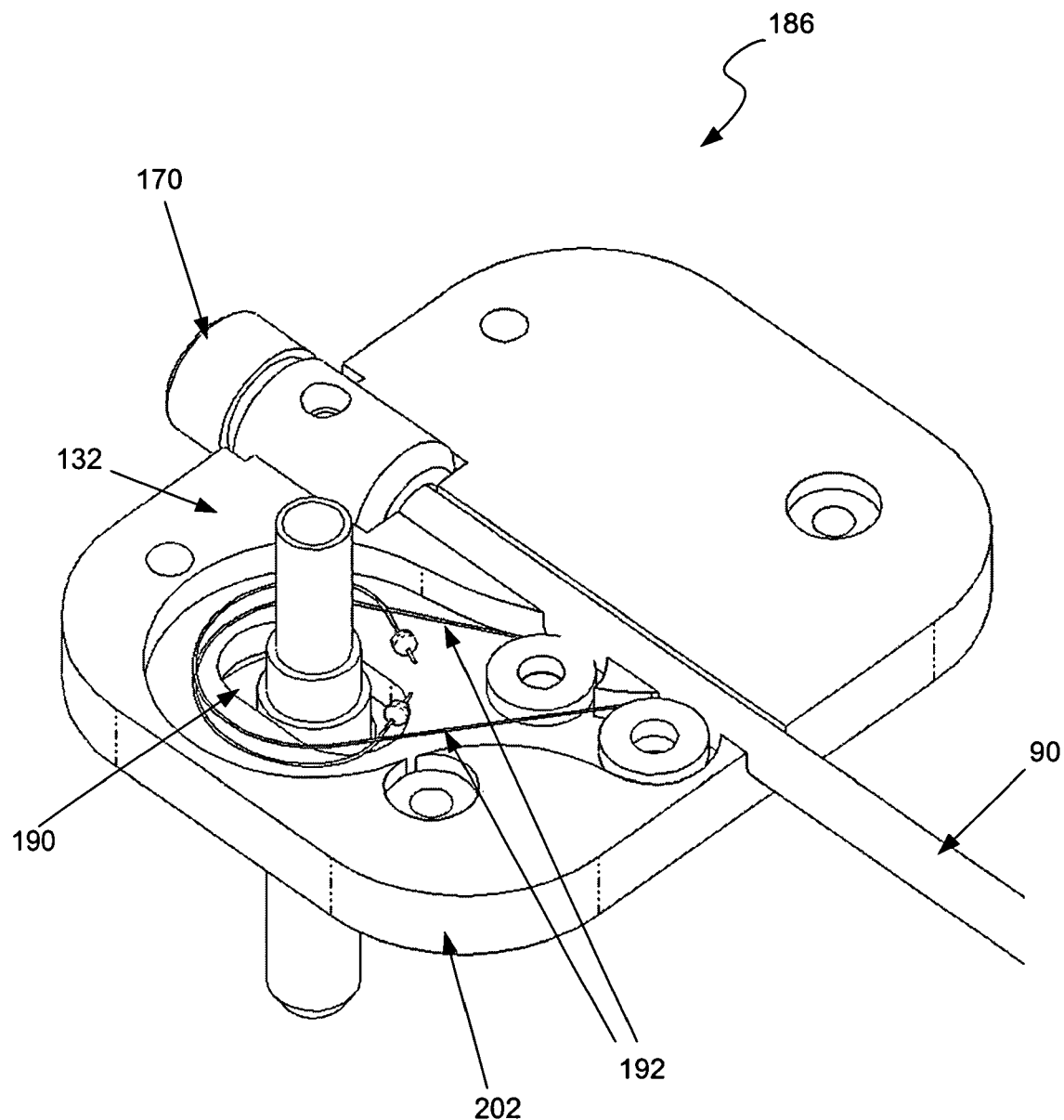
FIG. 27 is a partially disassembled perspective view of another proximal drivable assembly that can be used in the sheath instrument shown in FIG. 4.
Figure 28:
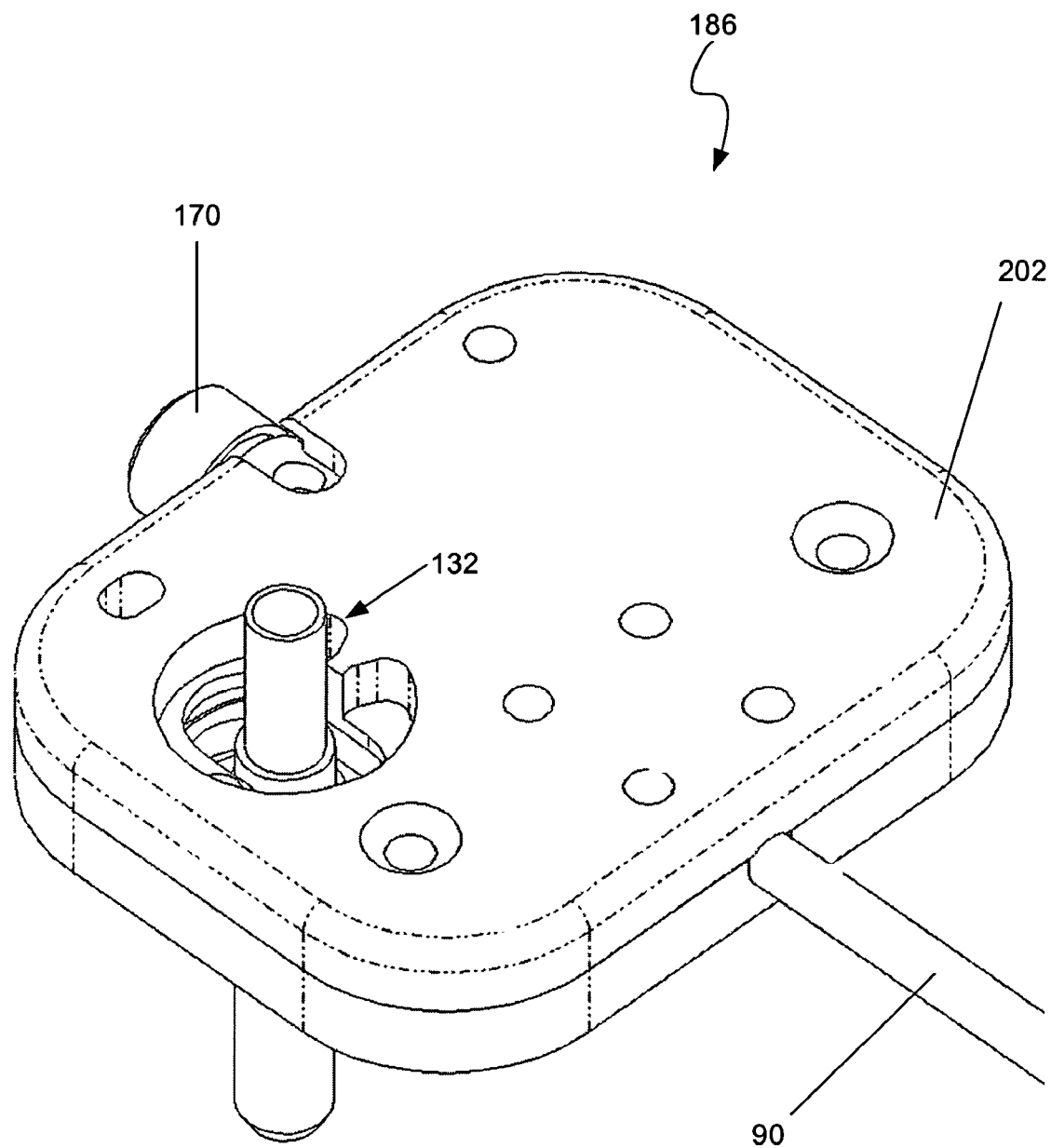
FIG. 28 is another partially assembled perspective view of the proximal drivable assembly of FIG. 27.

Referring to FIGS. 27 and 28, a sheath instrument (186) has only one control element interface assembly (132) (shown with manual adjustment knob and control pulley removed) configured to drive two control elements (192) (shown in FIG. 27). To this end, like in the previously described guide instrument illustrated in FIG. 19, each control element interface assembly (132) comprises a stacked pair of pulleys (not shown) to accommodate a respective pair of control elements (192). Also, like the previously described guide instrument illustrated in FIG. 19, rotation of the pair of pulleys proximal displaces one of the control elements (192) and distally displaces the other control element (192), thereby deflecting the distal end of the sheath catheter member (208) in the predetermined direction dictated by the proximally displaced control element (192).

The control element interface assembly (132) is also configured to maintain a minimal amount of tension on the two control elements (192) using a slotted guide instrument base (202). In particular, the sheath instrument base (202) forms slots (190) through which an instrument driver tensioning mechanism may keep control elements (192) taut during operation of the instrument (186) by translating the control element interface assembly (132) within the slot (190). Depending upon the amount of tensioning deflection within the slot (190), it may be desirable to remove the rotational range of motion limitation pin (not shown) from the manual adjustment knob (not shown) to prevent impingement of the pin, knob, and instrument base (202), as the control element interface assembly (132) is moved in the respective slot (190) relative to the rest of the instrument base (202). As with the previously described guide instrument illustrated in FIG. 19, the use of slots (190) in which the respective control element interface assemblies (132) can translate also provides an addition means for deflecting the distal end of the catheter member (90).

Figure 29:
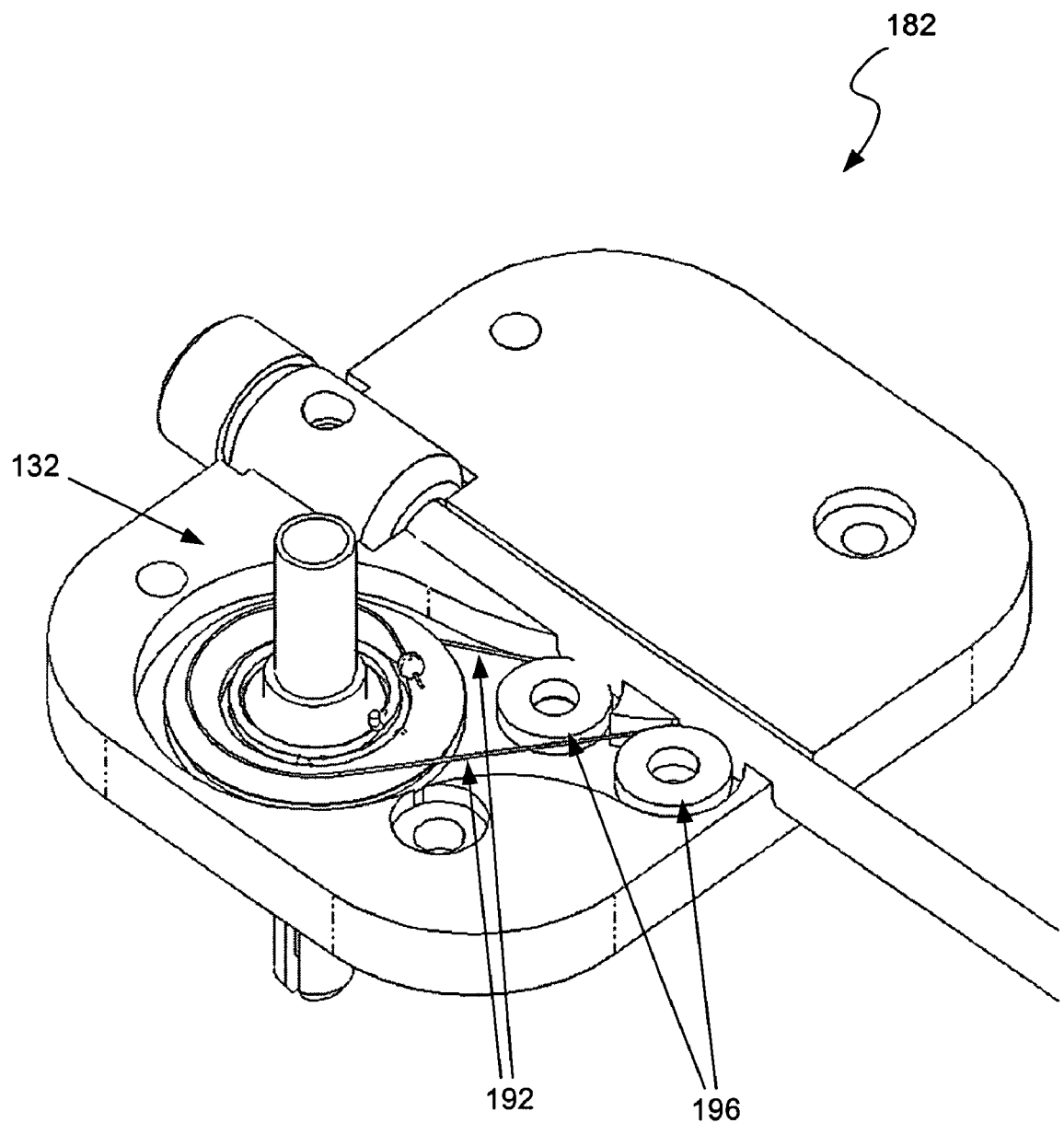
FIG. 29 is a partially disassembled perspective view of still another proximal drivable assembly that can be used in the sheath instrument shown in FIG. 4.
Figure 30:
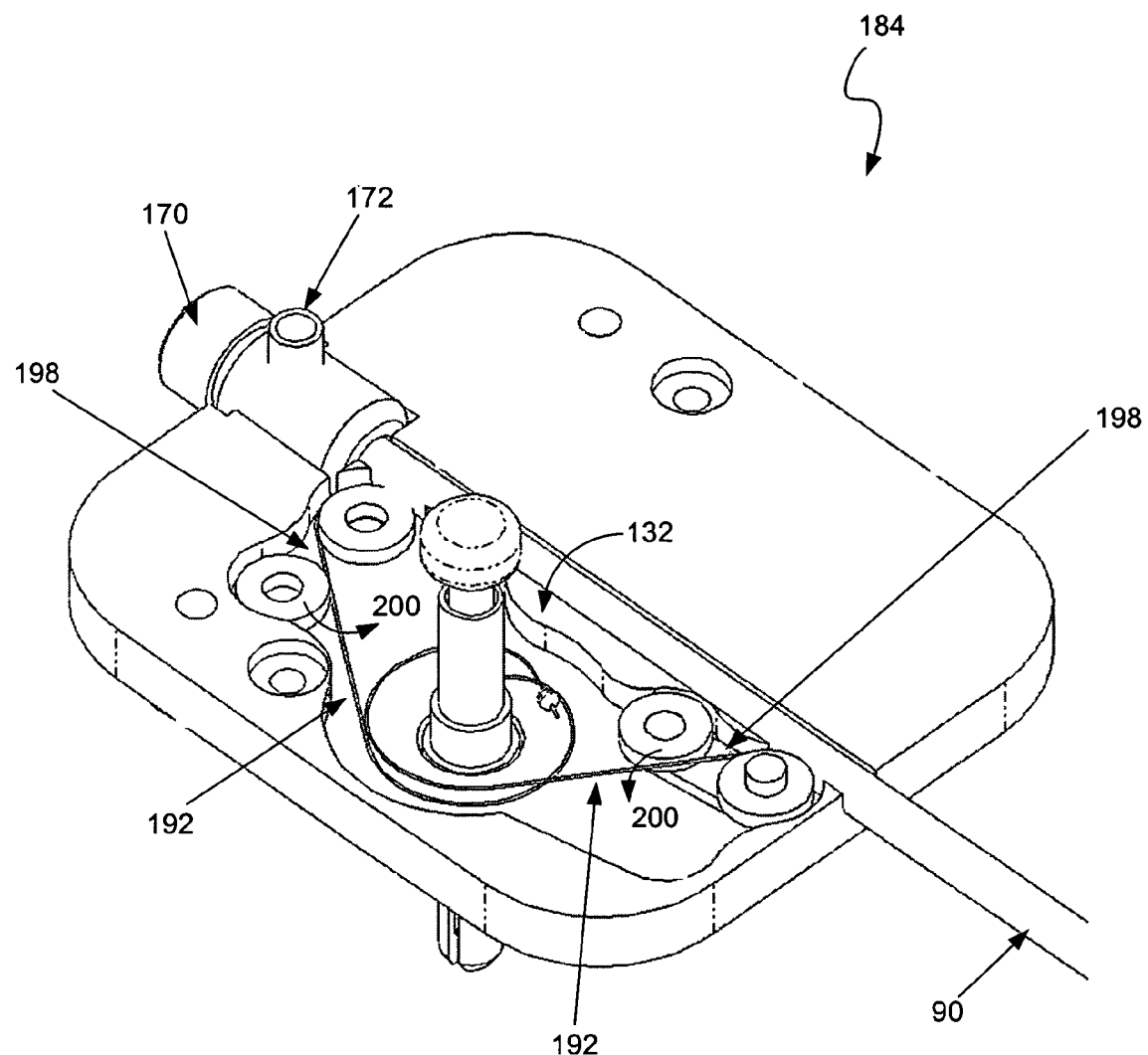
FIG. 30 is a partially disassembled perspective view of yet another proximal drivable assembly that can be used in the sheath instrument shown in FIG. 4.

Referring to FIG. 29, yet another sheath instrument (182) has a single control element interface assembly (132) (shown with manual adjustment knob removed) and two control elements (192). The sheath instrument (182) is not configured for slotted tensioning. Instead, the control elements (192) of this embodiment may be pre-tensioned and kept in position with the help of a fixed idler control element pathway (196) to facilitate maintenance of tension for control purposes. Referring to FIG. 30, still another sheath instrument (184) has a single control element interface assembly (132) (shown with manual adjustment knob removed) and two control elements (192), with a spring-loaded idler (198) tensioning of the control elements (192). As with the aforementioned spring-loaded idler tensioning instrument embodiments, the spring-loaded idlers urge (200) the control elements (192) into tension to facilitate control.

Figure 31:
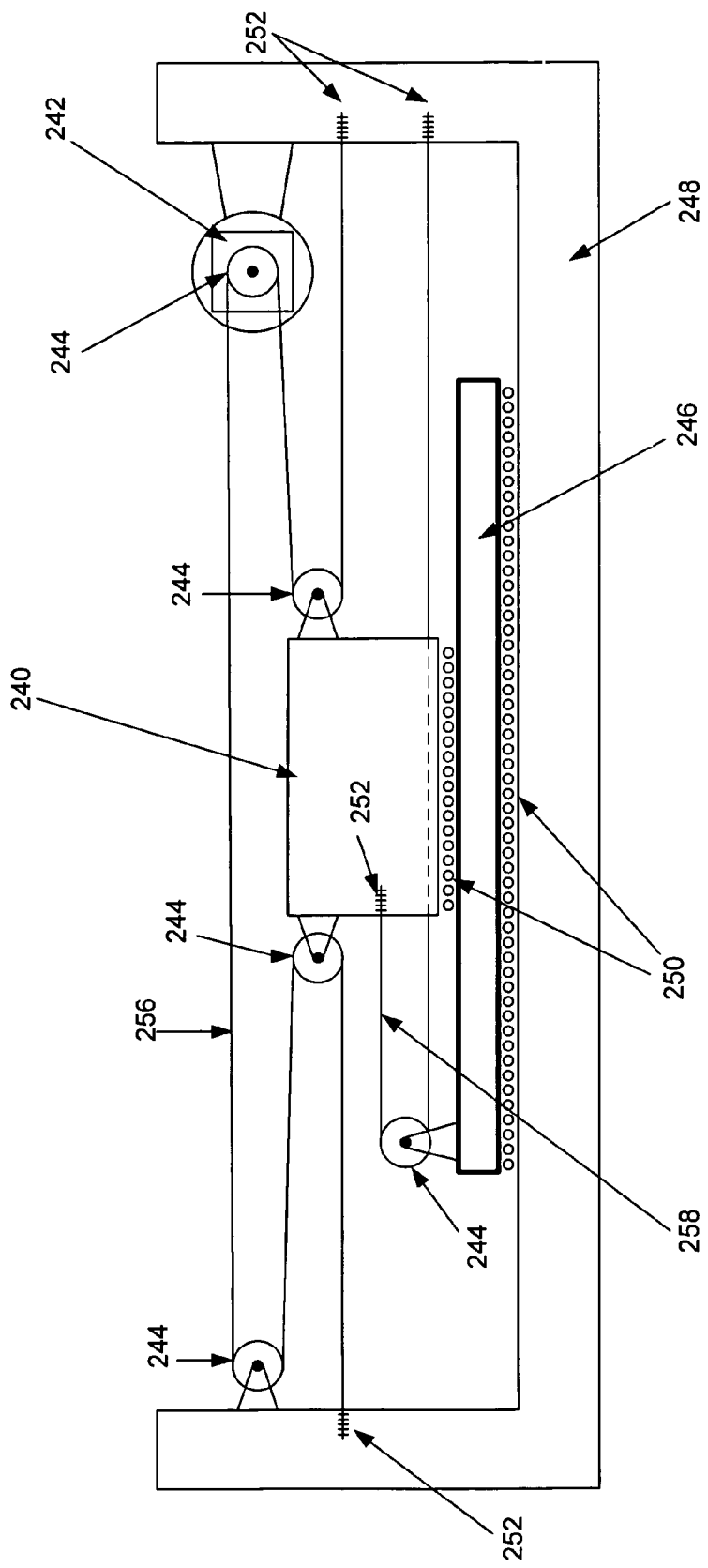
FIG. 31 is a side schematic view of a instrument driver used in either of the robotic catheter systems of FIGS. 1 and 2.

FIGS. 31-39 depict various aspects of embodiments of an instrument driver (16). Referring specifically to FIG. 31, the instrument driver (16) comprises a carriage (240) that is slidably mounted upon a platform (246), which is slidably mounted to a base structure (248). The slidable mounting (250) at these interfaces may be accomplished with high-precision linear bearings. The depicted system has two cables (256, 258) running through a plurality of pulleys (244) to accomplish motorized, synchronized relative motion of the carriage (240) and platform (246) along the slidable interfaces (250). As will be apparent to those skilled in the art, as the motor (242) pulls on the carriage displacement cable (256) with a tension force T, the carriage (240) feels a force of 2*T. Further, as the motor (242) pulls the carriage displacement cable (256) by a displacement X, the carriage moves by X/2, and the platform (246) moves by half that amount, or X/4, due to its "pulleyed" synchronization cable (258) and termination (252).

Figure 32:
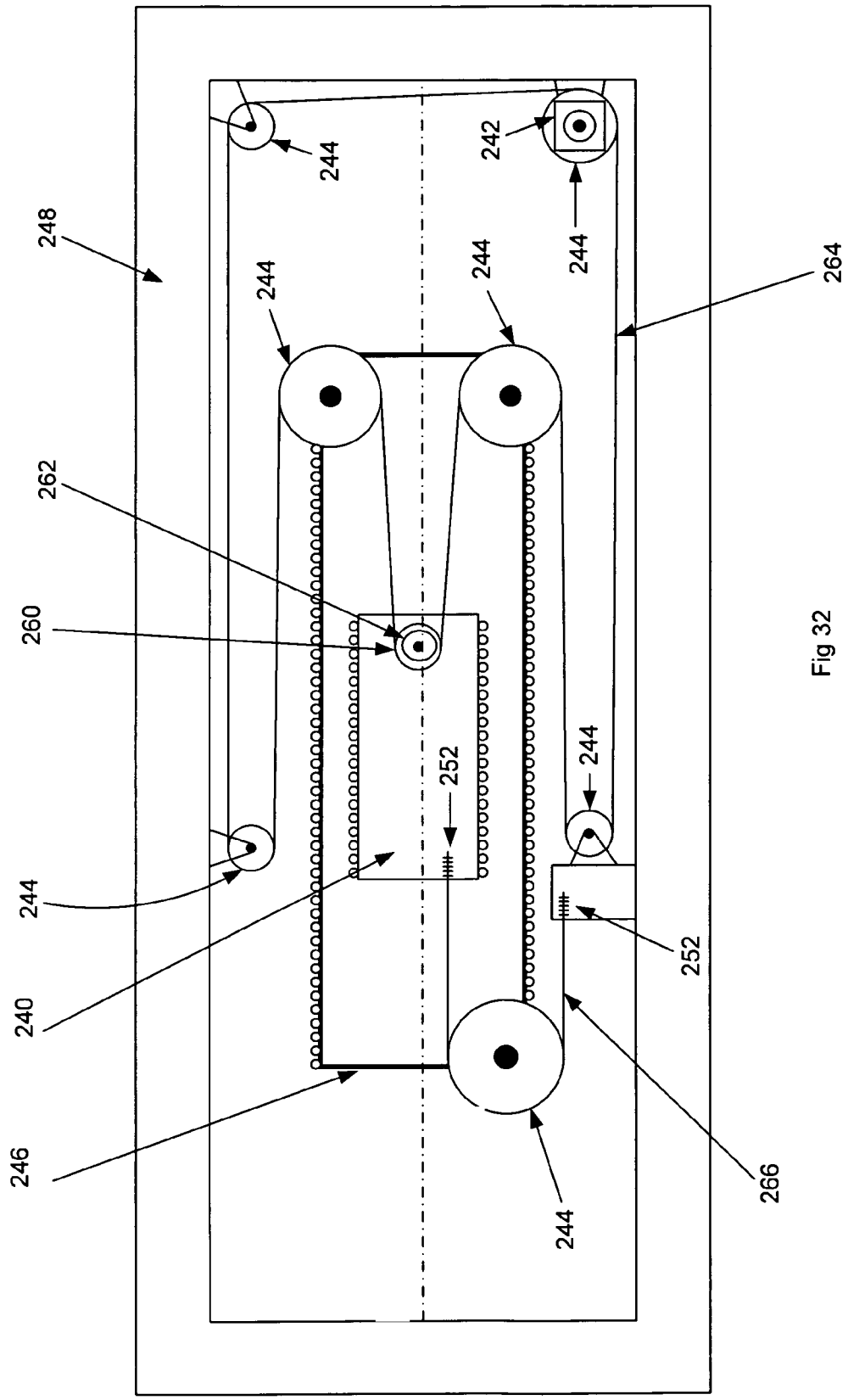
FIG. 32 is a top schematic view of the instrument driver of FIG. 31.

Referring to FIG. 32, an instrument interface pulley (260) associated with a guide instrument interface socket (270), in which an axel (54) of a respective control element interface assembly (132) of the guide instrument (18) is mated, is driven to produce both directions of rotation independently from the position of the carriage (240), to which it is coupled, along the linear pathway prescribed by the slidable interfaces (250). With a mechanical schema similar to that in FIG. 32, as the motor (242) pulls a deflection X in the instrument interface cable (264), the same deflection is seen directly at the instrument interface pulley (260), regardless of the position of the carriage (240) relative to the motor (242), due to the synchronizing cable (266) positioning and termination (252).

Figure 33:
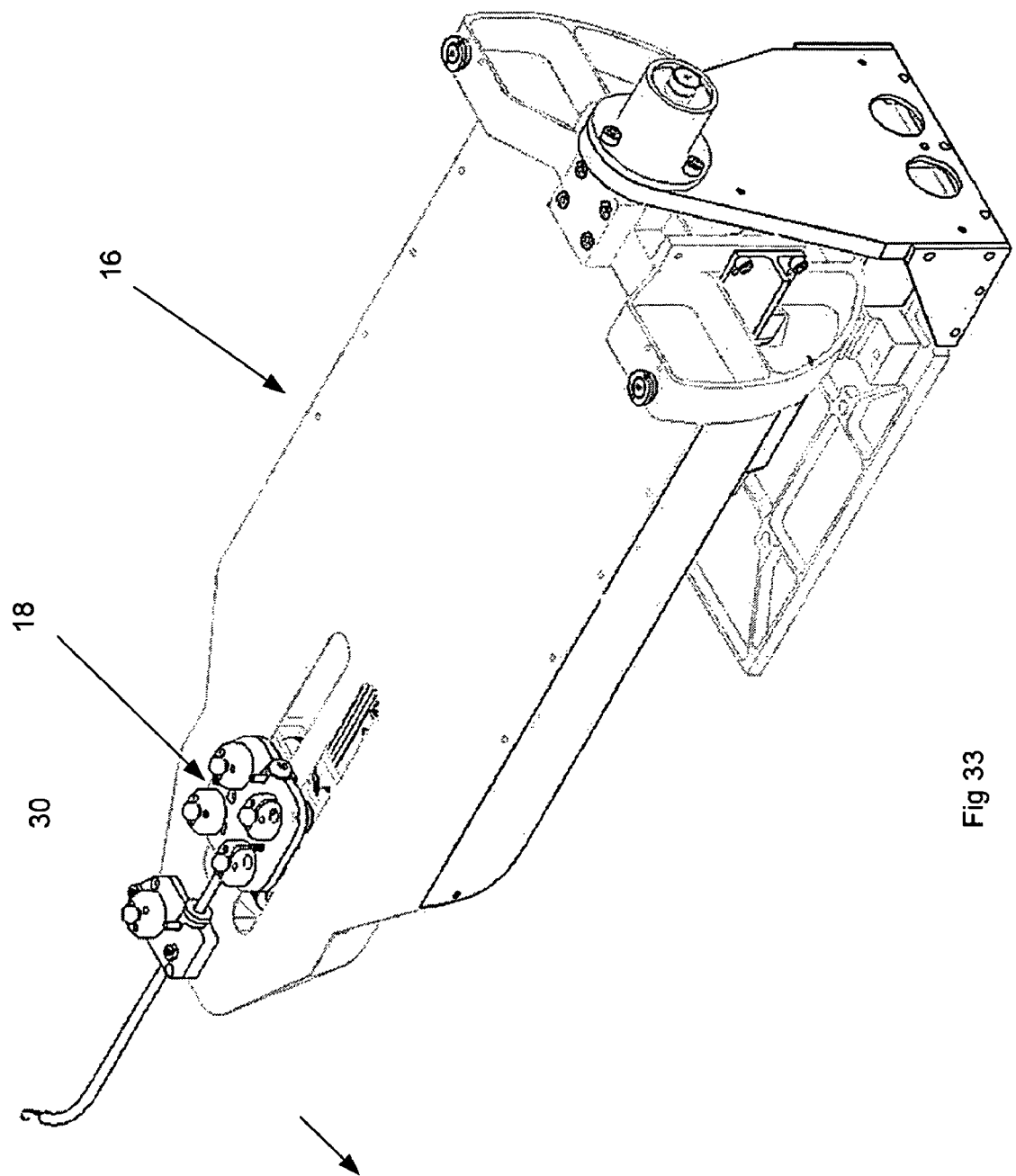
FIG. 33 is partially disassembled perspective view of the instrument driver of FIG. 31.
Figure 34:
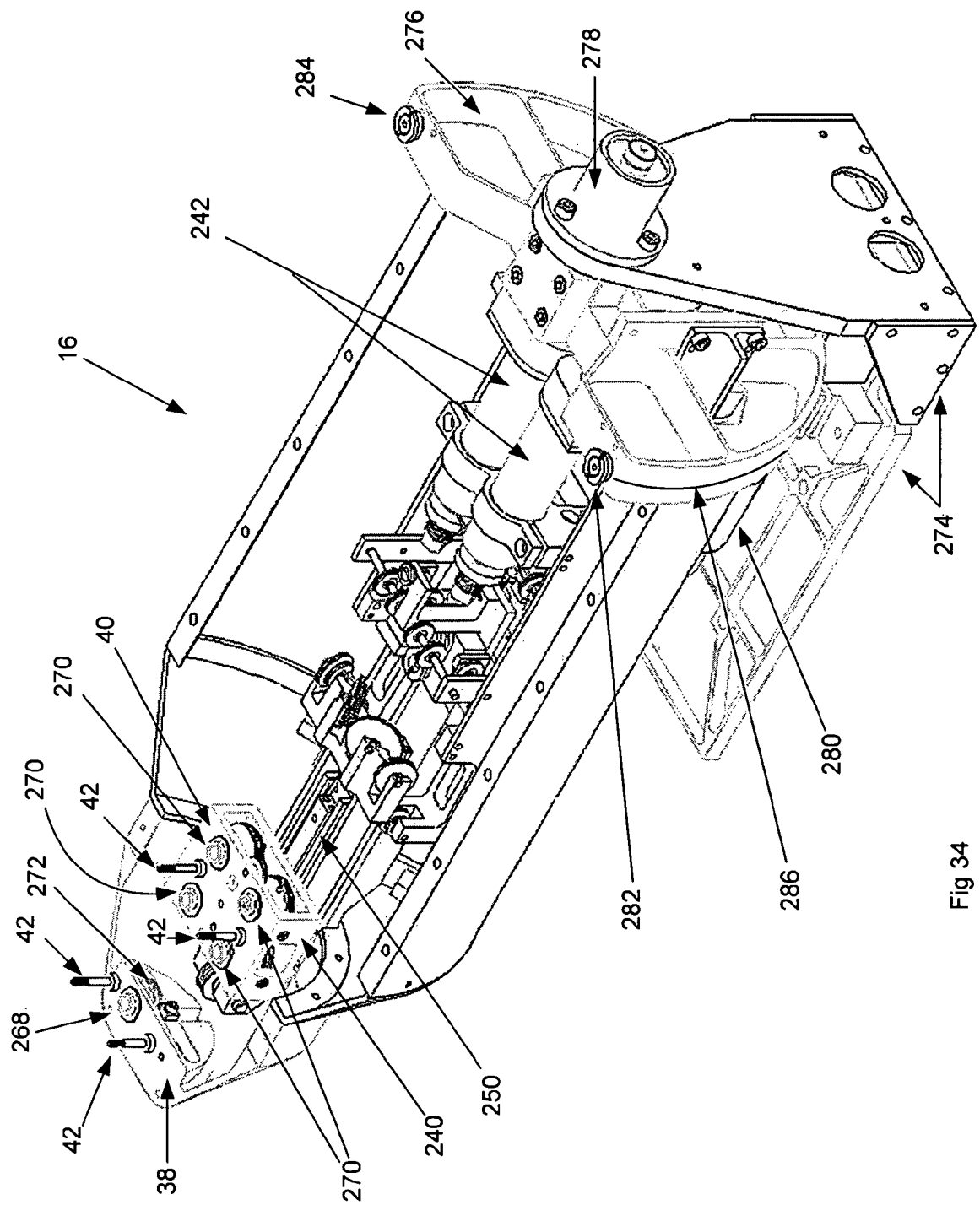
FIG. 34 is another partially disassembled perspective view of the instrument driver of FIG. 31.

Referring to FIGS. 33 and 34, the instrument driver (16) is depicted as interfaced with the guide instrument (18) and sheath instrument (30). In this embodiment, the sheath instrument interface surface (38) remains stationary, and requires only a simple motor actuation in order for the sheath catheter member (208) to be deflected using an interfaced control element via a control element interface assembly (132). This may be accomplished with a simple cable loop about a sheath socket drive pulley (272), which is associated with an sheath instrument interface socket (168) in which an axel (54) of a respective control element interface assembly (132) of the sheath instrument (30) is mated, and a capstan pulley (not shown), which is fastened to a motor, similar to the two upper motors (242) (visible in FIG. 34). The drive motor for the sheath socket drive schema is hidden under the linear bearing interface assembly.

The drive schema for the four guide instrument interface sockets (270) is more complicated, due in part to the fact that they are coupled to a carriage (240) configured to move linearly along a linear bearing interface (250) to provide for axial movement of the guide instrument (90) toward the patient relative to the instrument driver (16), operating table (22), and sheath instrument (30). The cabling and motor schema that moves the carriage (240) along the linear bearing interface (250) is an implementation of the diagrammatic view depicted in FIG. 31. The cabling and motor schema that drives each of the four depicted guide instrument interface sockets (270) is an implementation of the diagrammatic view depicted in FIG. 32. Therefore, in the instrument driver (16), wherein four separate cable drive loops serve four separate guide instrument interface sockets (270), and wherein the carriage (240) has motorized insertion, there is achieved a functional equivalent of a system such as that diagrammed in FIGS. 31 and 32, all fit into the same construct. Various conventional cable termination and routing techniques are utilized to accomplish a preferably high-density instrument driver structure with the carriage (240) mounted forward of the motors for a lower profile patient-side interface.

Figure 35:
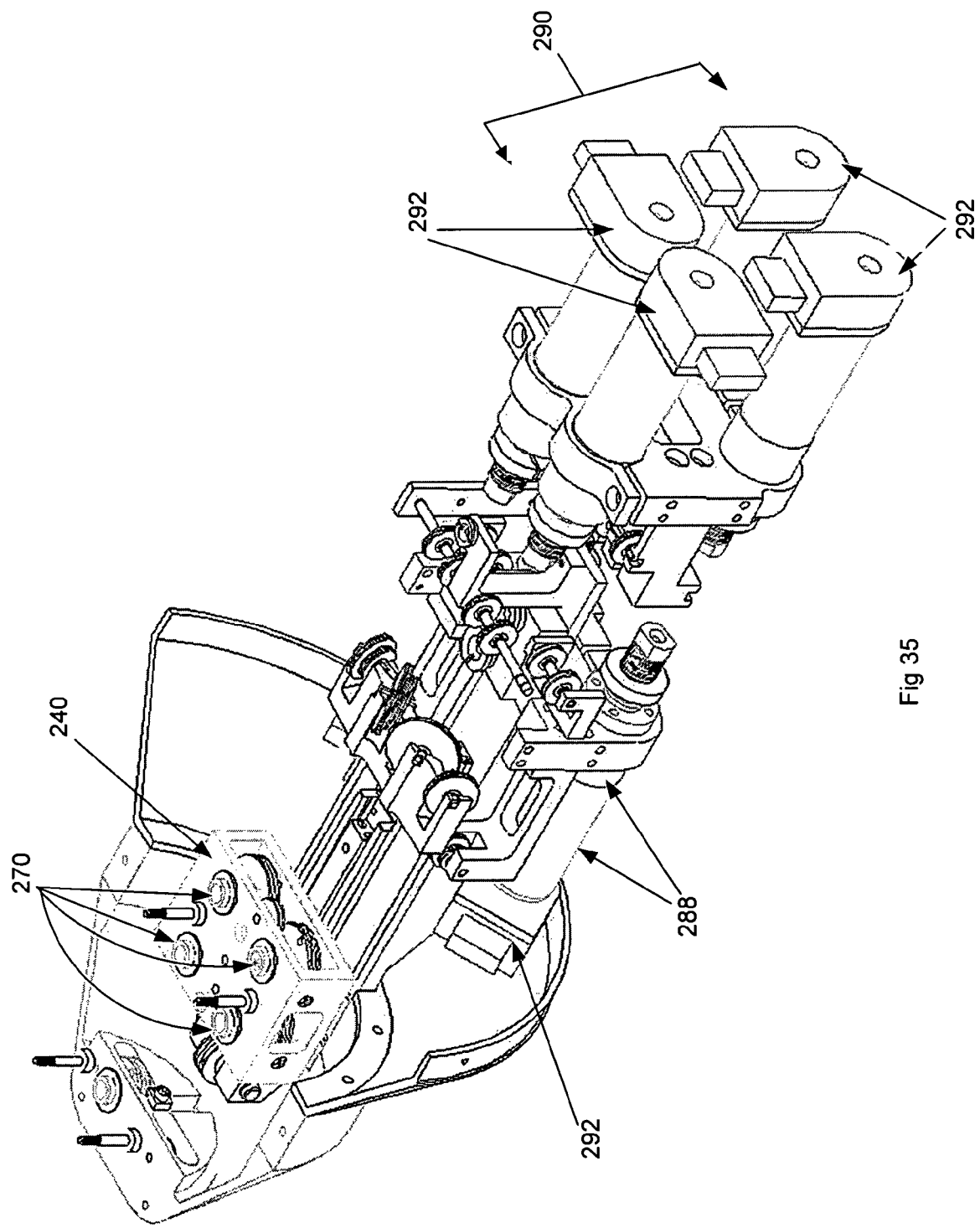
FIG. 35 is still another partially disassembled perspective view of the instrument driver of FIG. 31.
Figure 36:
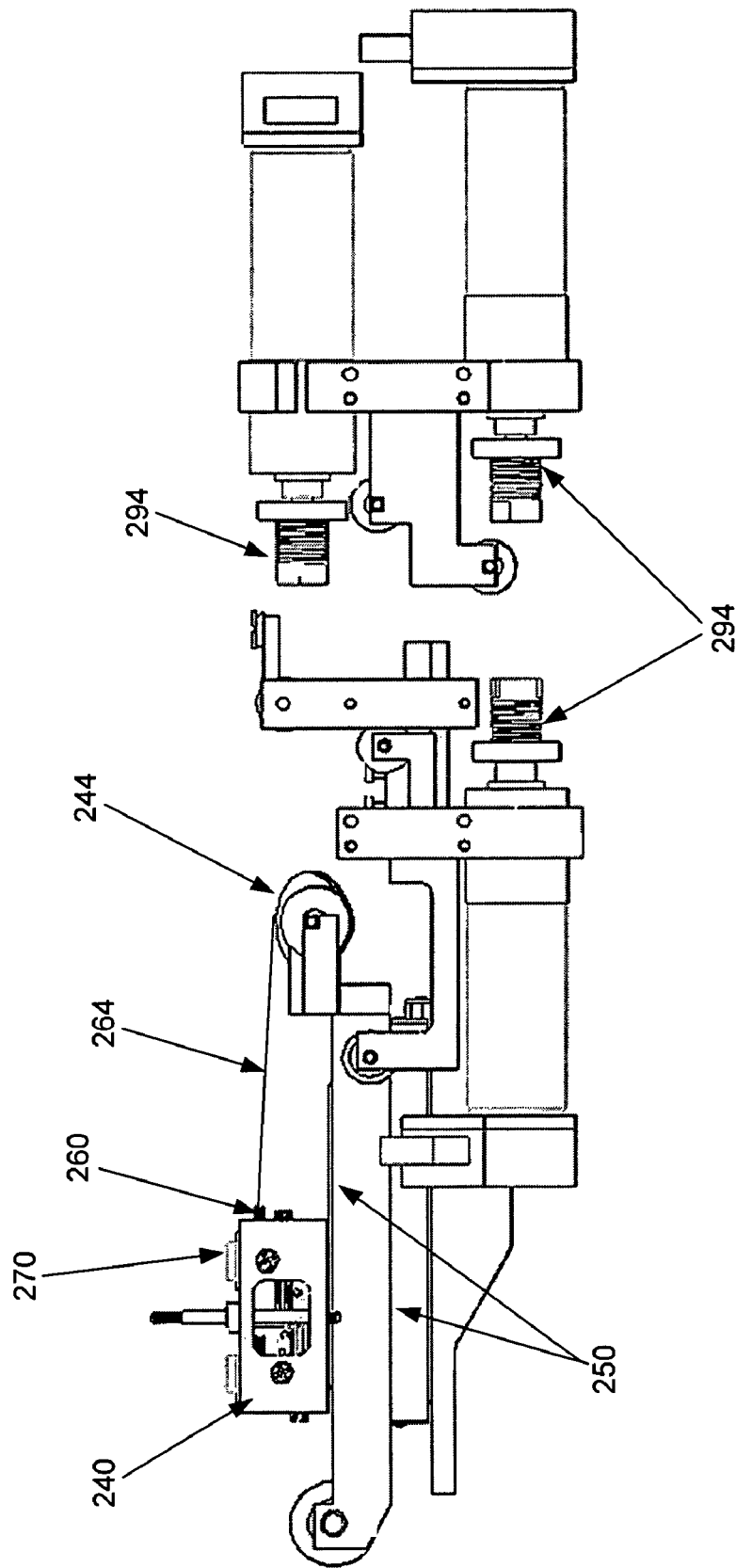
FIG. 36 is a side view of a motor and cabling assembly used in the instrument driver of FIG. 33.

As illustrated in FIG. 35, a group of four motors (290) is used to respectively drive the four guide instrument interface sockets (270). Each motor (290) has an associated high-precision encoder for controls purposes. As illustrated in FIG. 36, the instrument interface cable (264) bends around a pulley (244) and completes part of its loop to an instrument interface pulley (260) rotatably coupled to the carriage (240) and coupled to a guide instrument interface socket (270), around the instrument interface pulley (260), and back to a motor capstan pulley (294). To facilitate adjustment and installation of such cable loops, and due to the fact that there is generally no requirement to have a loop operating for a long period of time in one direction, thereby perhaps requiring a true unterminated loop, two ends of a cut cable loop preferably are terminated at each capstan (294). Referring back to FIG. 35, a group of two motors (one hidden, one visible (288)) with encoders (292) are configured to drive insertion of the carriage (240) and the sheath instrument interface socket (268).

Figure 37:
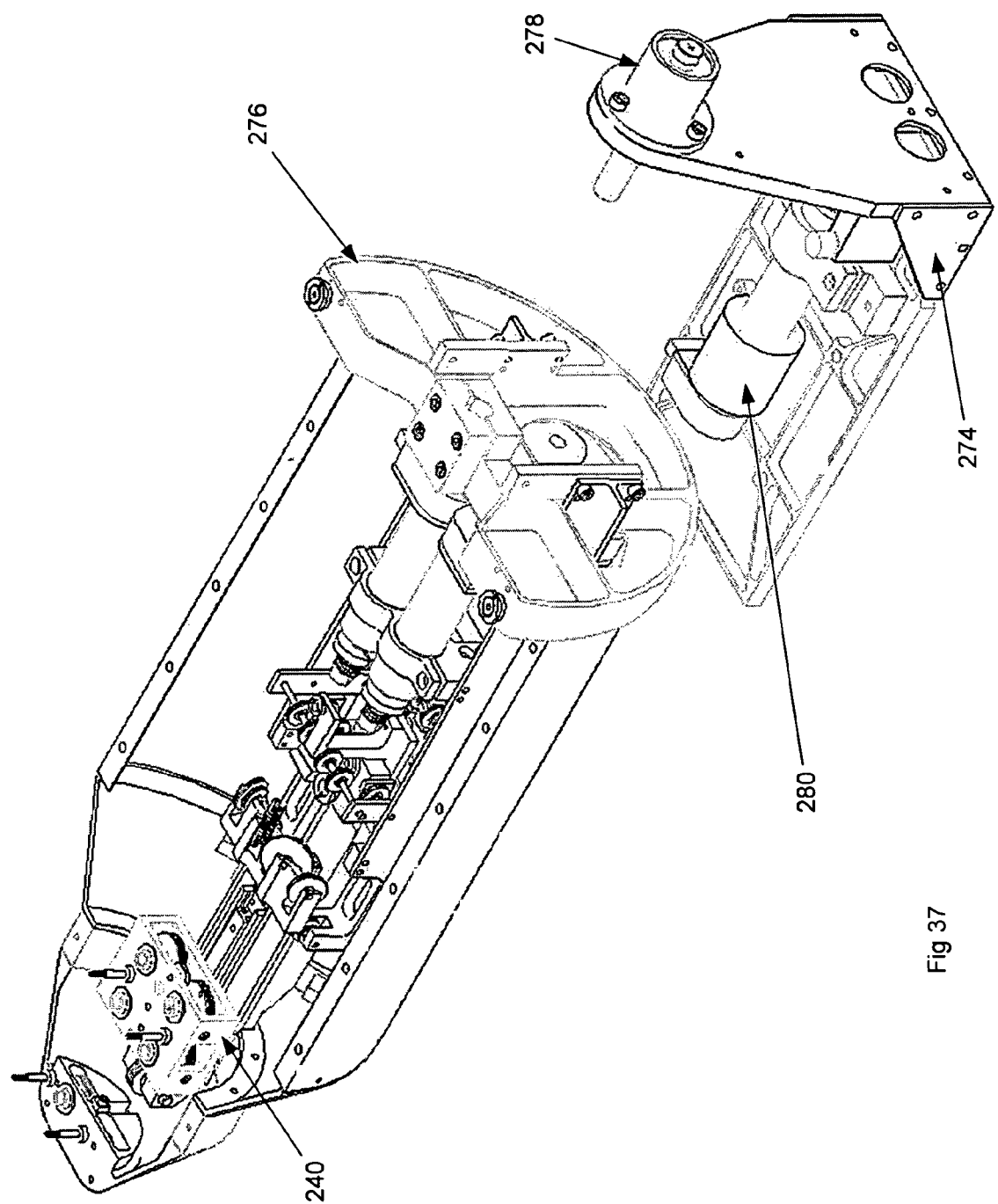
FIG. 37 is a partially disassembled perspective view of the instrument driver of FIG. 33 and an instrument driver mount.

Referring to FIG. 37, the instrument driver (16) is rotatably mounted to an instrument driver base (274), which is configured to interface with an instrument driver mounting brace (not shown), such as that depicted in FIG. 1, or a movable setup joint construct (not shown), such as that depicted in FIG. 2. Rotation between the instrument driver base (274) and an instrument driver base plate (276) to which it is coupled is facilitated by a heavy-duty flanged bearing structure (278). The flanged bearing structure (278) is configured to allow rotation of the body of the instrument driver (16) about an axis approximately coincident with the longitudinal axis of a guide instrument (not shown) when the guide instrument is mounted upon the instrument driver (16) in a neutral position. This rotation preferably is automated or powered by a roll motor (280) and a simple roll cable loop (286), which extends around portions of the instrument driver base plate and terminates as depicted (282, 284). Alternatively, roll rotation may be manually actuated and locked into place with a conventional clamping mechanism.

Figure 38:
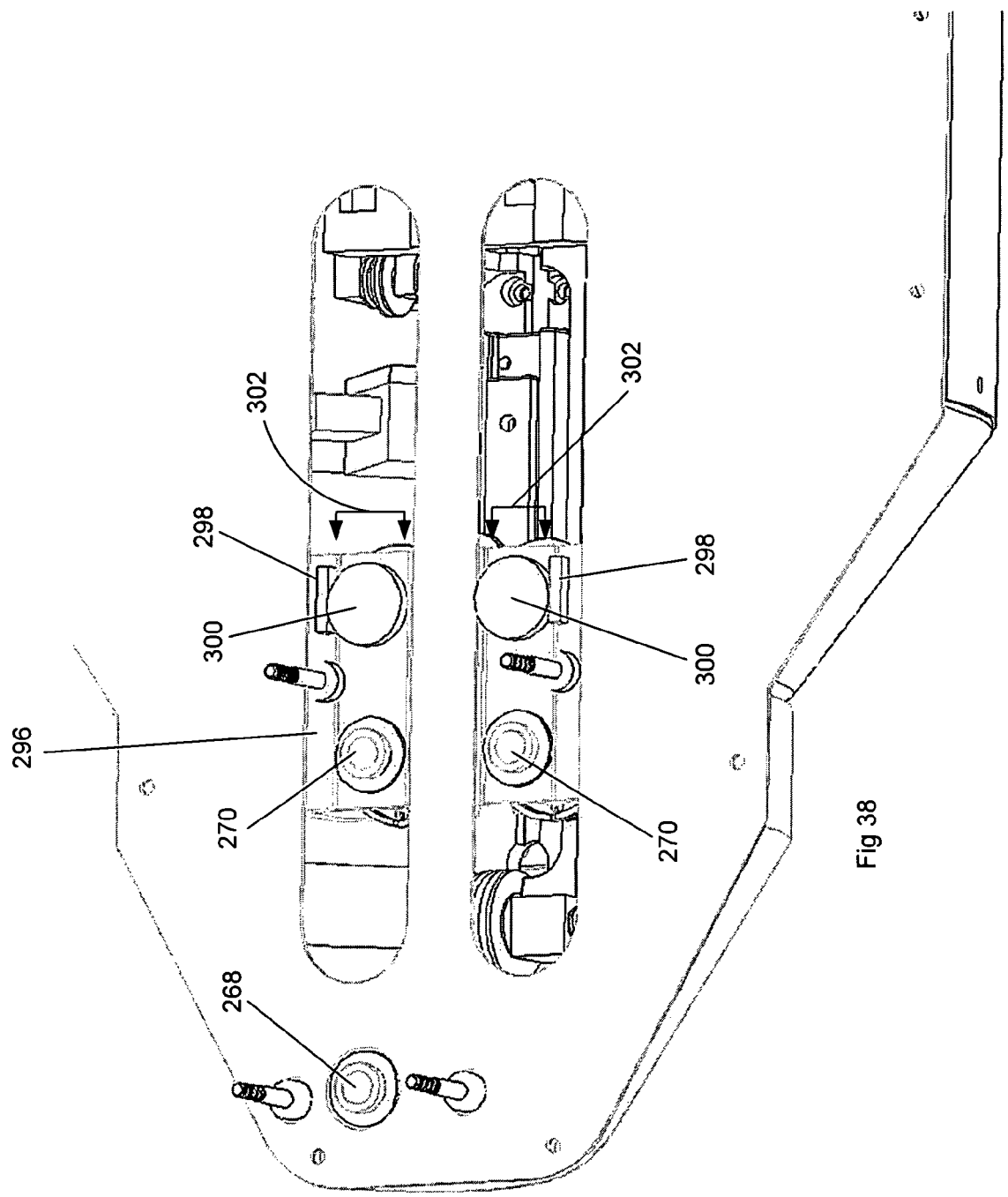
FIG. 38 is a partially cutaway perspective view of another instrument driver that can be used in the either of the robotic catheter systems of FIGS. 1 and 2.
Figure 39:
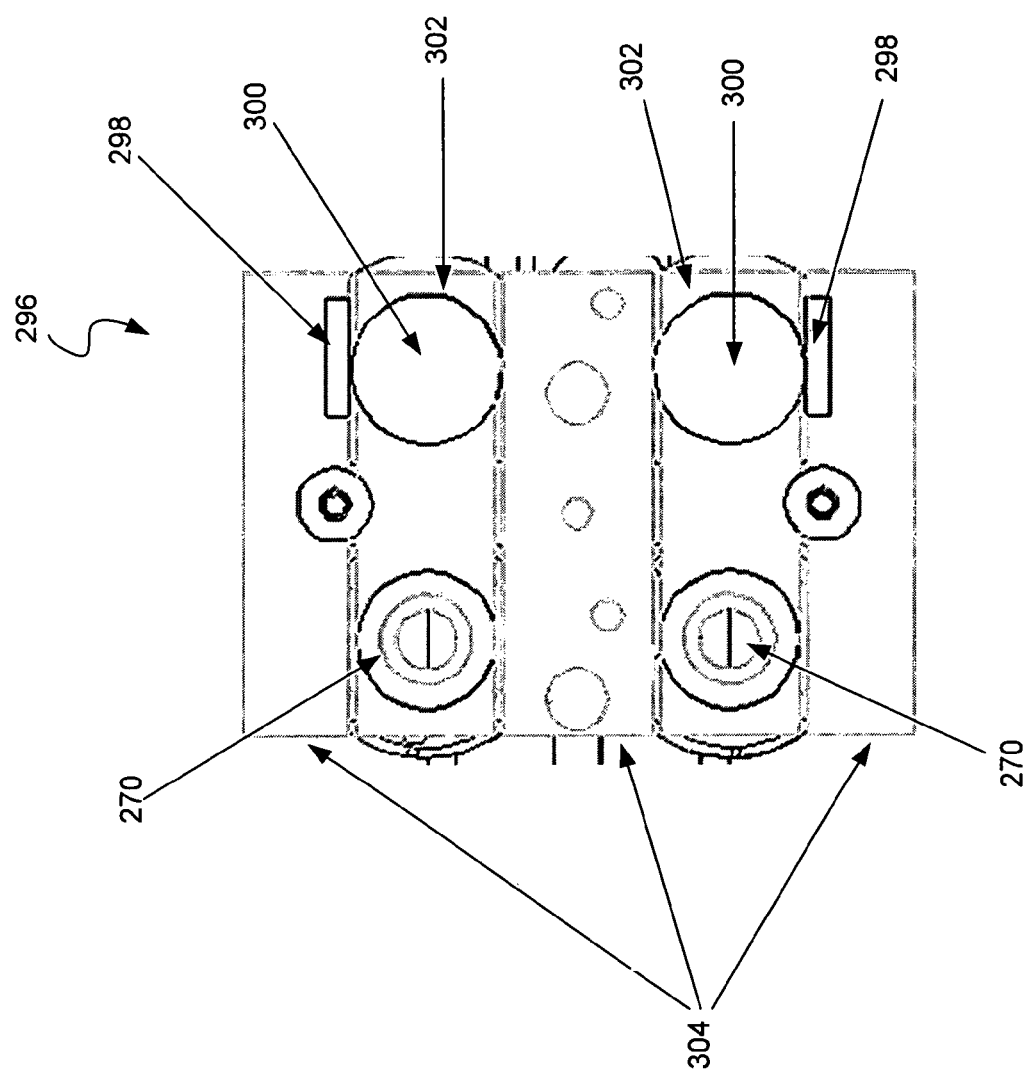
FIG. 39 is top view of a carriage used in the instrument driver of FIG. 38.

The carriage (240) depicted in the embodiments of FIGS. 31-37 generally comprises a structural box configured to house the instrument interface sockets and associated instrument interface pulleys. Referring to FIGS. 38 and 39, a split carriage (296) is depicted, comprising a main carriage body (304) similar to that of the non split carriage depicted in the previous carriage (240), and either one or two linearly movable portions (302), which are configured to slide relative to the main carriage body (304) when driven along either forward or backward relative to the main carriage body (304) by a gear (300) placed into one of the guide instrument interface sockets, the gear (300) configured to interface with a rack (298) mounted upon the main carriage body (304) adjacent the gear (300). Each movable portion (302) comprises a guide instrument interface socket (270) in which an axel (54) of a respective control element interface assembly (132) of the guide instrument (18) is mated. Thus, in the case where the guide instrument (18) has the slotted guide instrument base (188) illustrated in FIG. 18, movement of the movable portion (302) along a rectilinear path relative to the main carriage body (304) on which the instrument base, will move the control element interface assembly (132) along the same rectilinear path (i.e., within the rectilinear slots (190)) relative to the instrument base (188). In an alternate embodiment, the carriage (296) need not be split on both sides, but may have one split side and one non-split side. Further, while a carriage with four guide instrument interface sockets is suitable for driving a guide instrument with anywhere from one to four control element interface assemblies, the additional hardware required for all four control element interface assemblies may be undesirable if an instrument only requires only one or two.

Referring to FIGS. 40-50, another variation of an instrument driver is depicted, comprising a variation of a split carriage design. Unlike embodiments in which each instrument base interface is moved straight along a slot, rotated, or both (independently), the embodiment of FIGS. 40-50 provides rotation and/or arcuate slot motion by a "winged" split carriage design, wherein the tension member pulleys and axles may be rotated about the axle axis, or moved along an arcuate pathway, independently.

Figure 40:
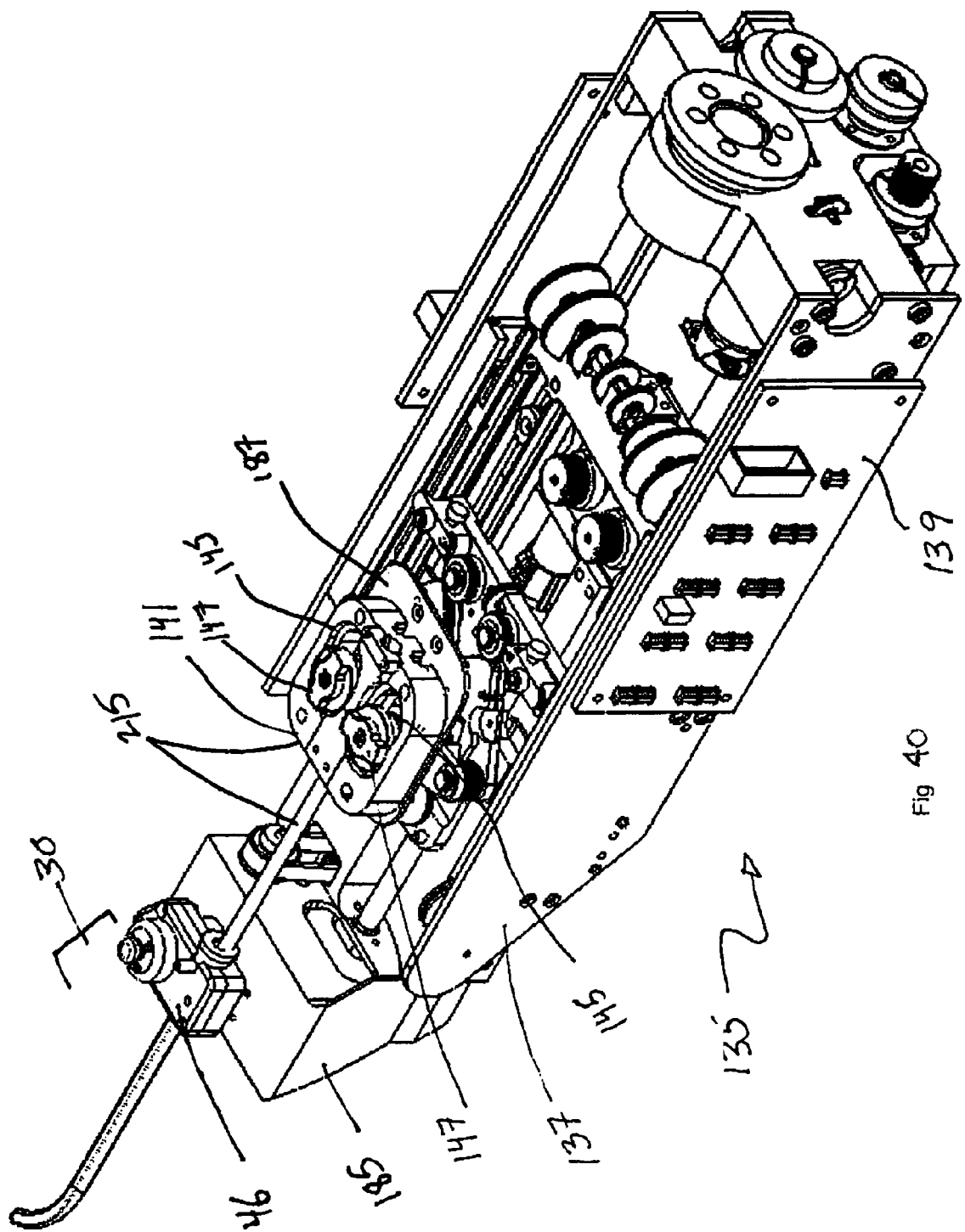
FIG. 40 is an isometric perspective view of an alternate instrument driver, incorporating a winged split carriage design according to one embodiment, shown with a top cover removed and engaging respective guide and sheath instruments.

Referring to FIG. 40, a winged split carriage instrument driver (135) is depicted coupled to a guide instrument (215) configured for the winged split carriage with a specialized guide instrument base (141) having two arcuate slots (145) as opposed to the straight slots of other embodiments. One or more electronics boards (139) preferably are coupled to the main housing structure (137) of the winged split carriage instrument driver (135). The depicted assembly also comprises a sheath instrument (30) movably threaded over at least a portion of the guide instrument (215) and coupled to the sheath frame block (185) which is coupled to the main housing structure (137) when the depicted assembly is fully assembled.

Figure 41:
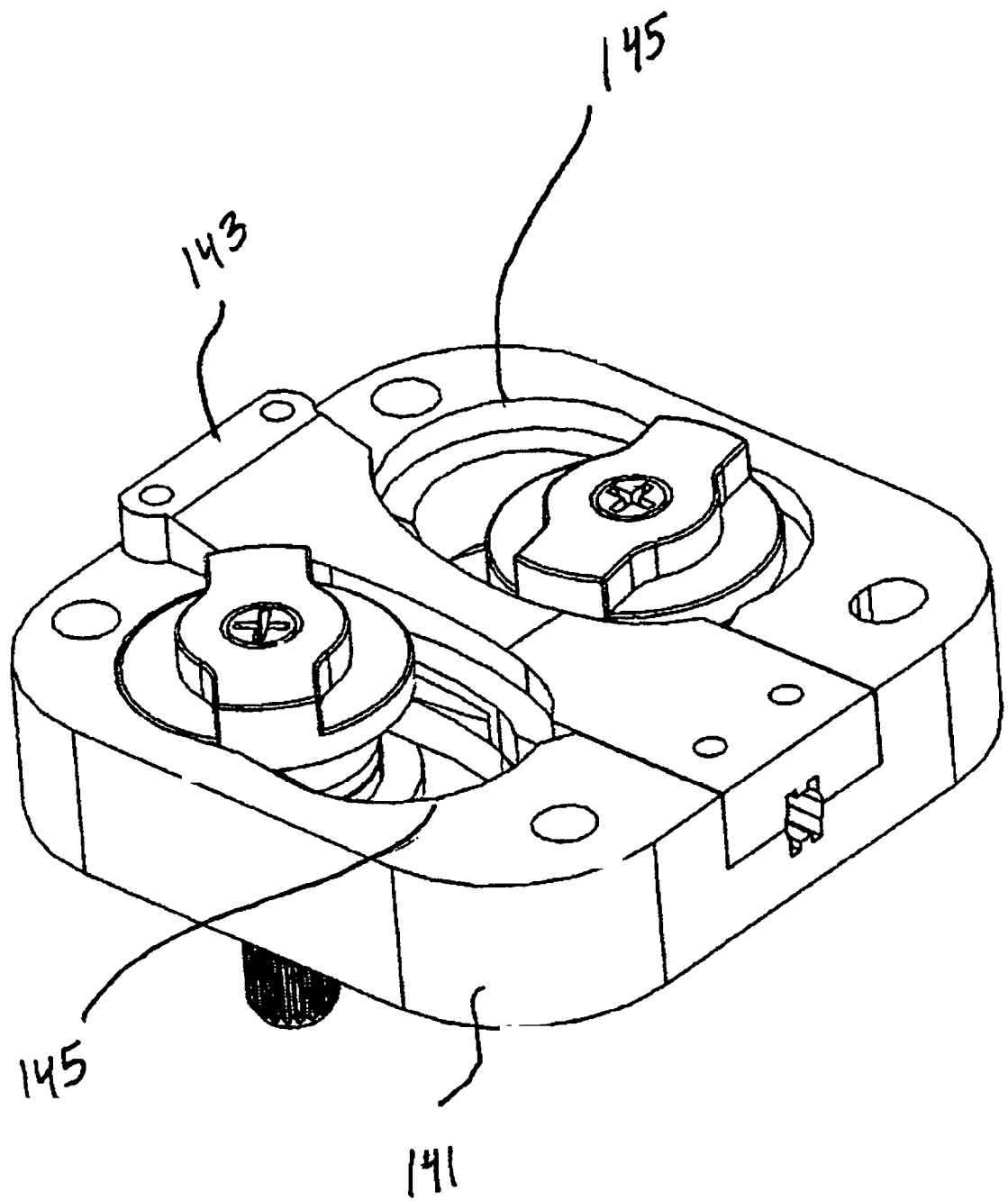
FIG. 41 is an isometric perspective view of a base member of the guide instrument shown in FIG. 40.
Figure 42:
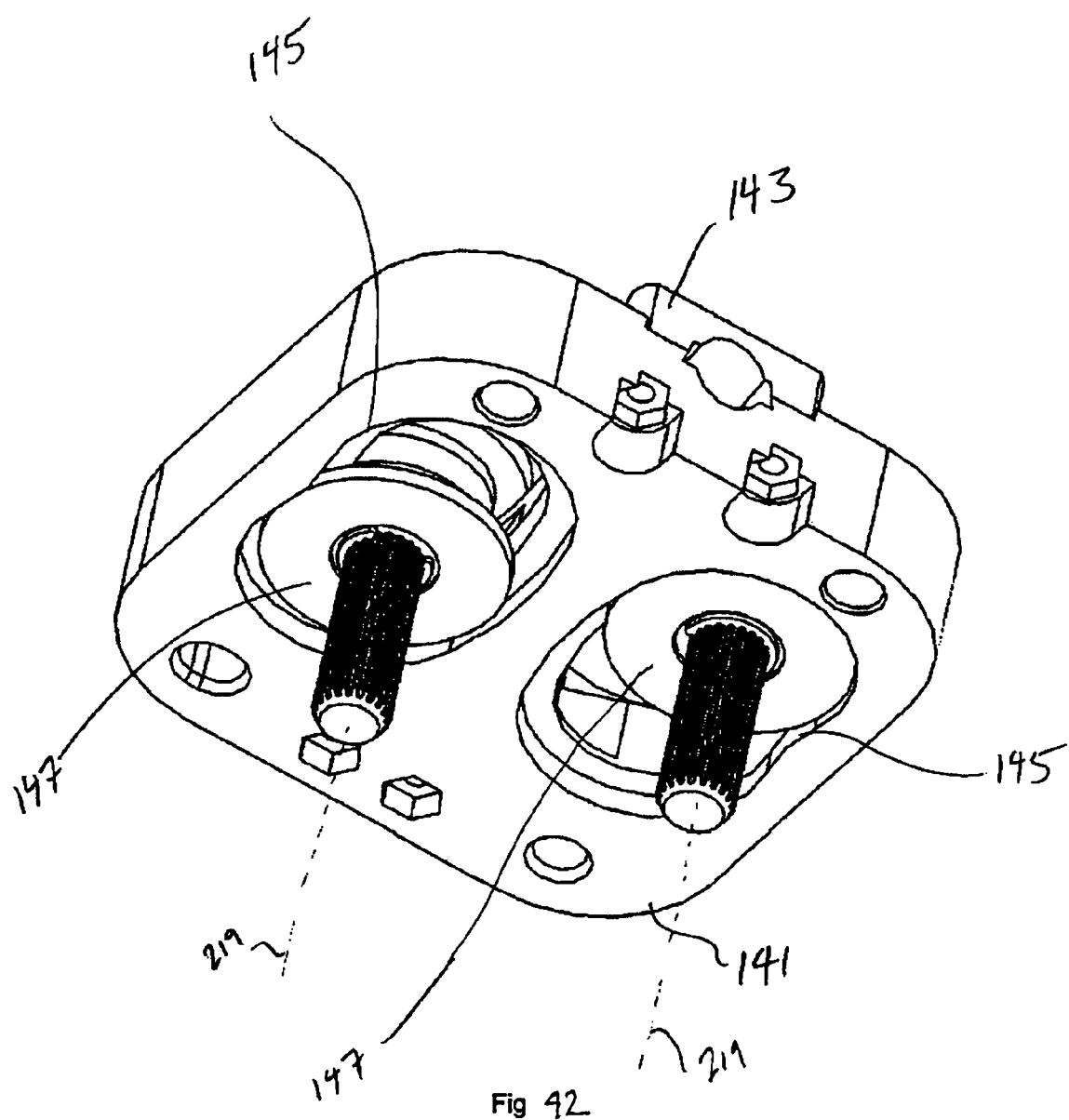
FIG. 42 is an isometric view of an underside of the guide instrument base of FIG. 41
Figure 43:
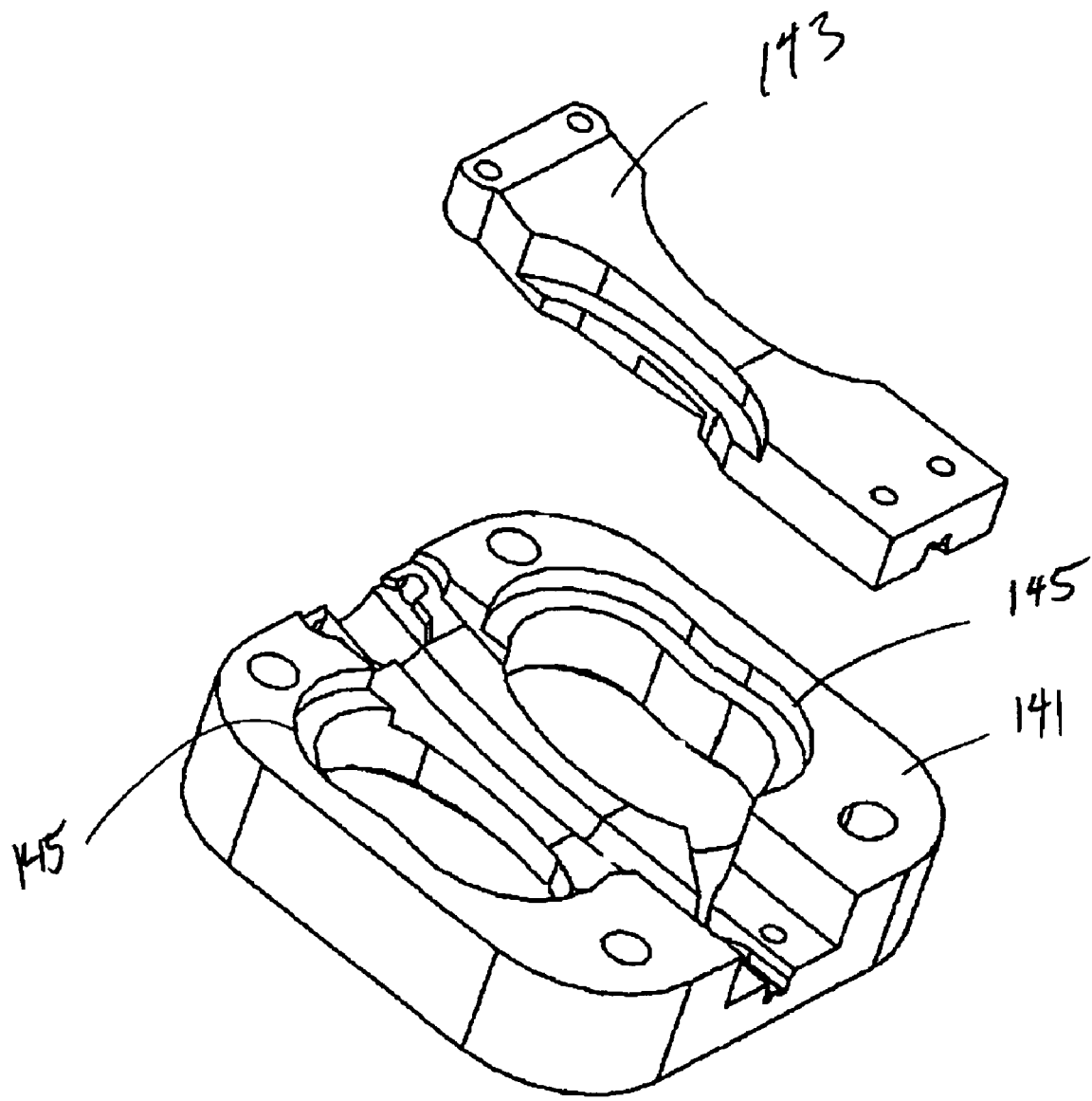
FIG. 43 is an exploded perspective isometric view of a top plate of the guide instrument shown in FIG. 40.

Referring to FIG. 41, a winged instrument driver guide instrument base (141) is depicted showing the arcuate slots (145) in greater detail, as well as a winged instrument driver guide instrument base top plate (143), which is configured to be fitted down upon the proximal tubular portion of a guide instrument catheter member (not shown) to maintain the relative positioning of the catheter member (not shown) relative to the winged instrument driver guide instrument base (141). An underside isometric view of the guide instrument base (141) is depicted in FIG. 42. In the depicted embodiment, a low-profile control element interface assembly (147) is configured to rotate about the longitudinal axis of the interface assembly (219) while also slidably translating through the associated arcuate slot (145). FIG. 43 depicts an exploded view of the winged instrument driver guide instrument base top plate (143) and winged instrument driver guide instrument base (141) depicted in FIG. 41, also showing the arcuate slots (145) defined therein.

Figure 44:
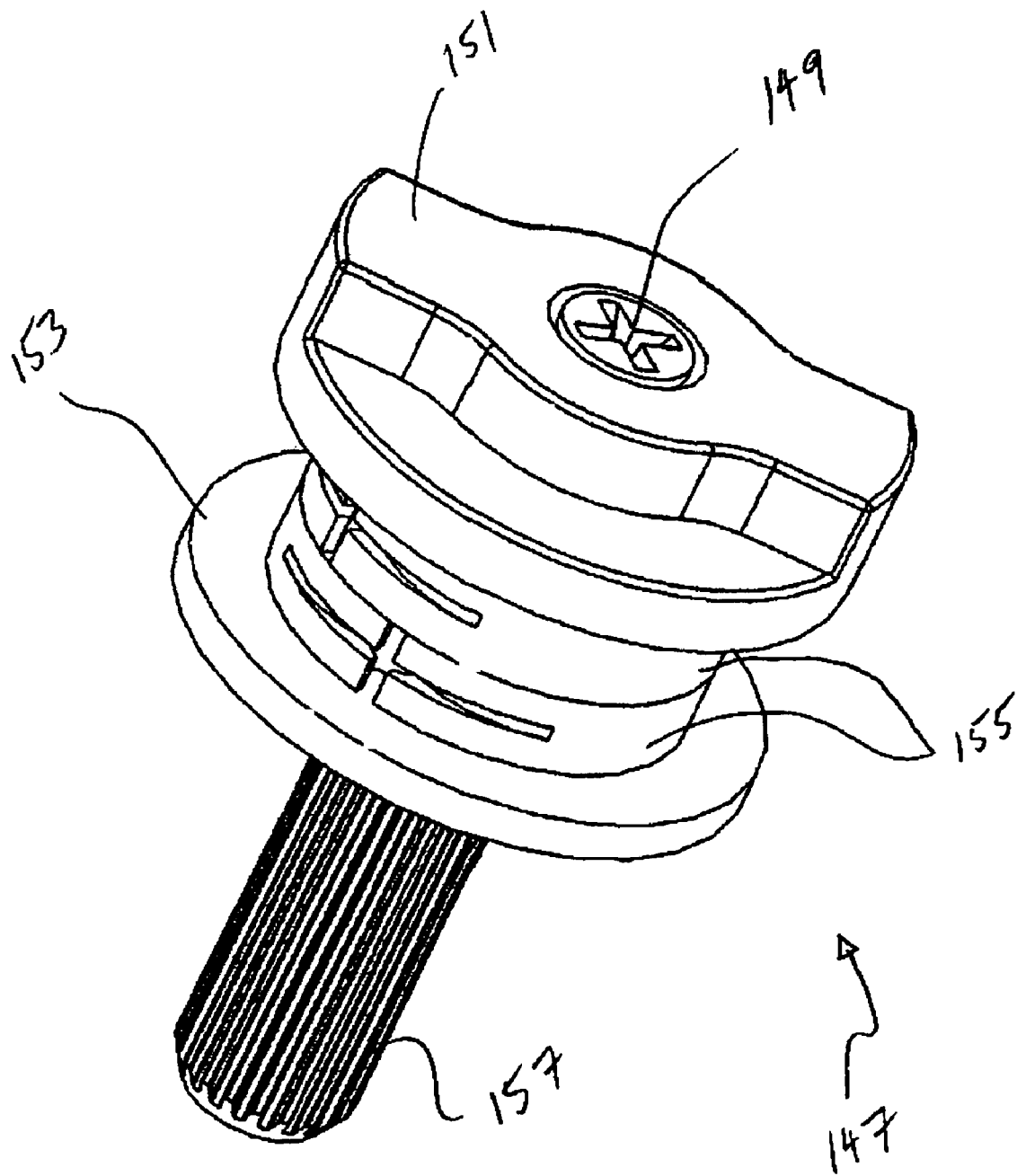
FIG. 44 is a perspective isometric view of a low-profile control element interface assembly used in the guide instrument of FIG. 40.
Figure 45:
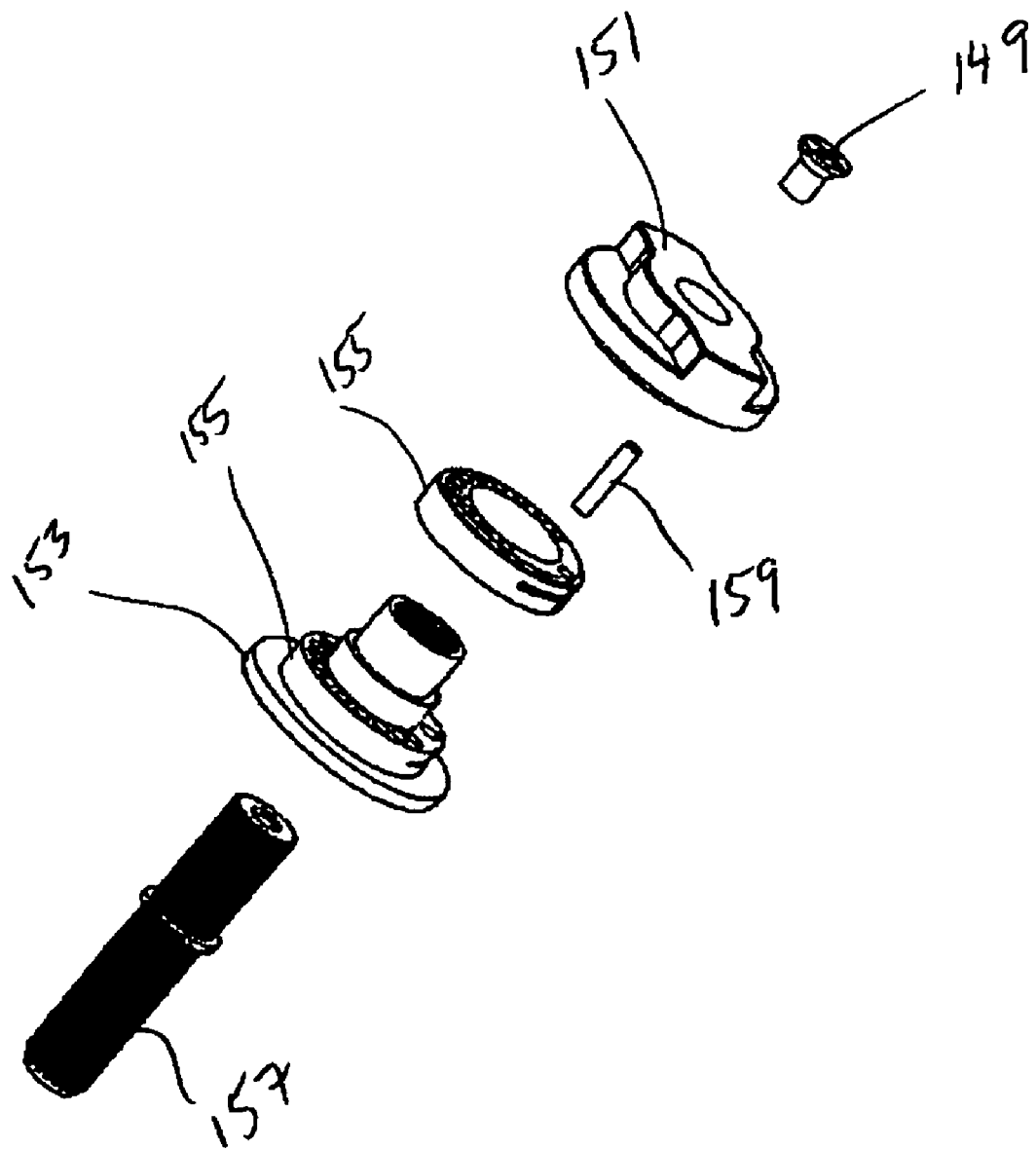
FIG. 45 is an exploded view of the assembly of FIG. 44.
Figure 86:
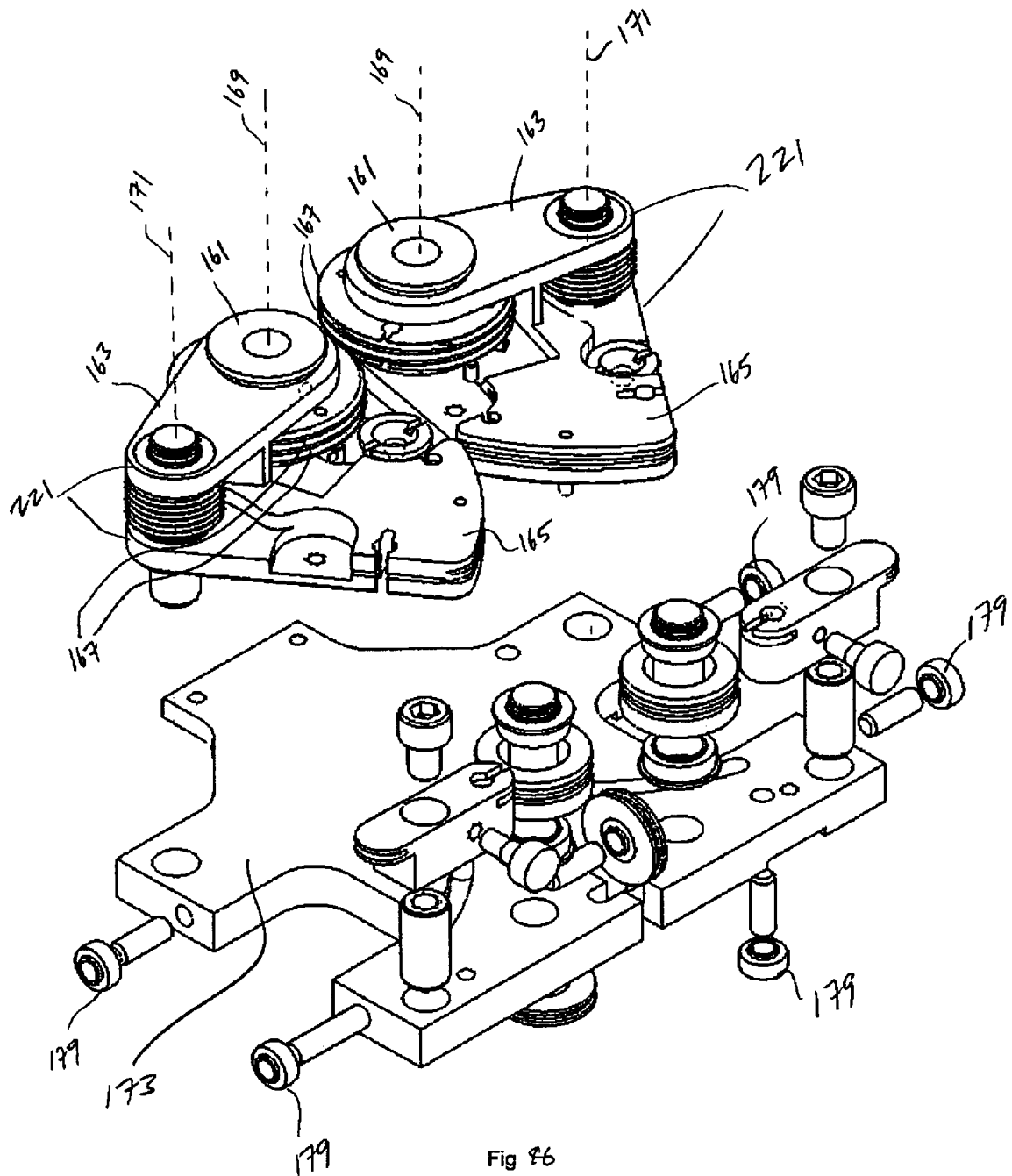

Referring to FIG. 44, a low-profile control element interface assembly (147) is shown in isometric view comprising a splined axle (157) coupled to a pulley flange (153), and also coupled to a set of control element pulleys (155) which are compressed between a low-profile manual adjustment knob (151) and the pulley flange (153) with a retaining fastener (149), such as a screw. An exploded view of the same structures is depicted in FIG. 45. Also shown in FIG. 45 is a pin (159) configured to prevent relative rotational displacement between the two control element pulleys (155) when the low-profile control element interface assembly (147) is assembled. The depicted embodiment of low-profile control element interface assembly (147) may be utilized with any of the aforementioned instrument base and instrument driver assemblies, subject to the requirement that the instrument interface sockets, labeled 44, for example in FIG. 5, preferably are also geometrically matched for a splined interface between socket and axle facilitating highly-efficient transfer of loads between the matched socket and axle. The low-profile control element interface assembly (147) preferably comprises polymers or metals which may be formed or machined into very high precision subassemblies or parts which are low in weight, high in hardness, and low in fracture toughness. In one embodiment, each of the components of the low-profile control element interface assembly (147) comprises polycarbonate or ultra-high-molecular-weight polyethylene.

Figure 47:
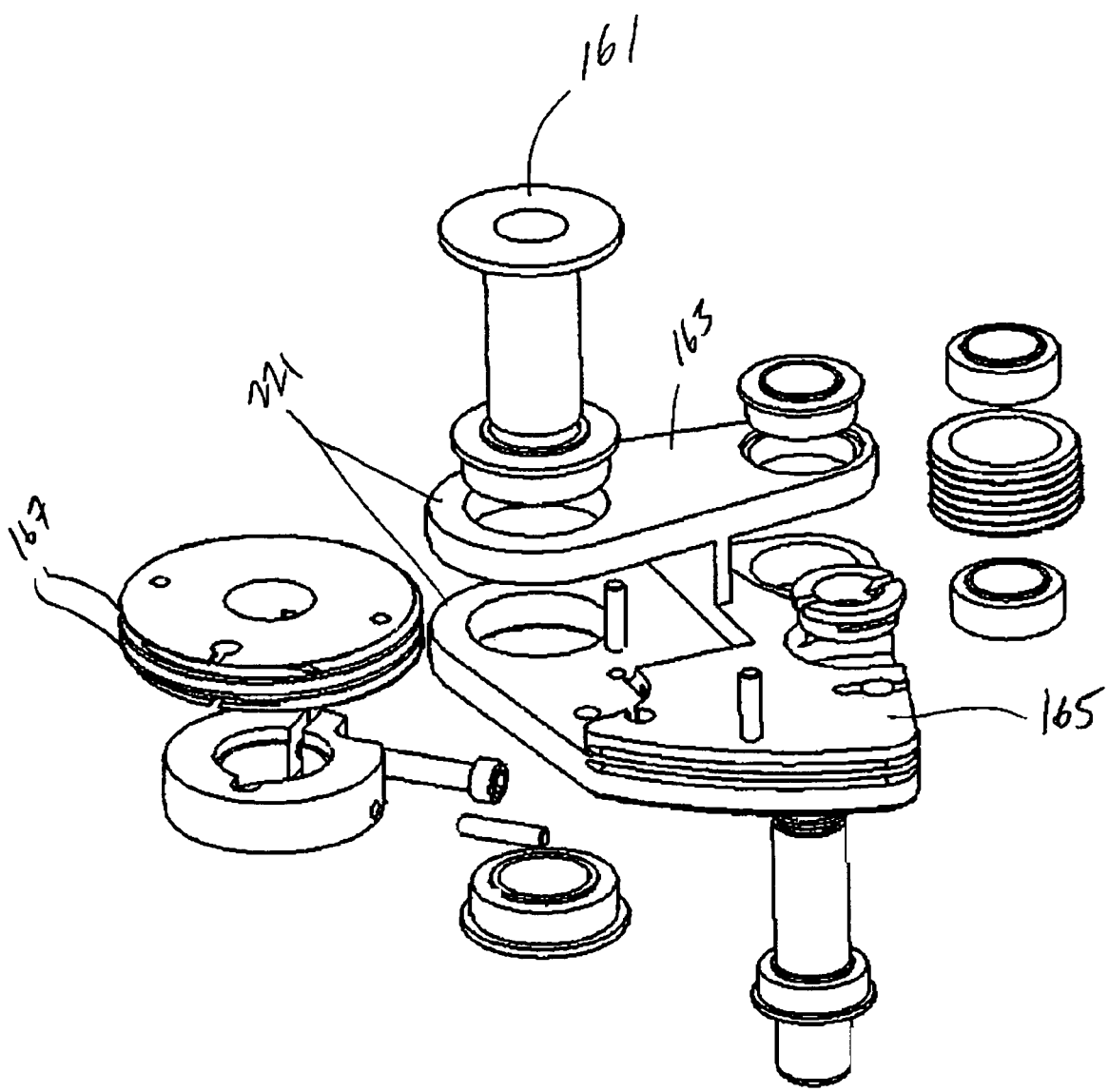
FIG. 47 is a further exploded view of a "wing" structures and associated members of the assembly of FIG. 46.
Figure 48:
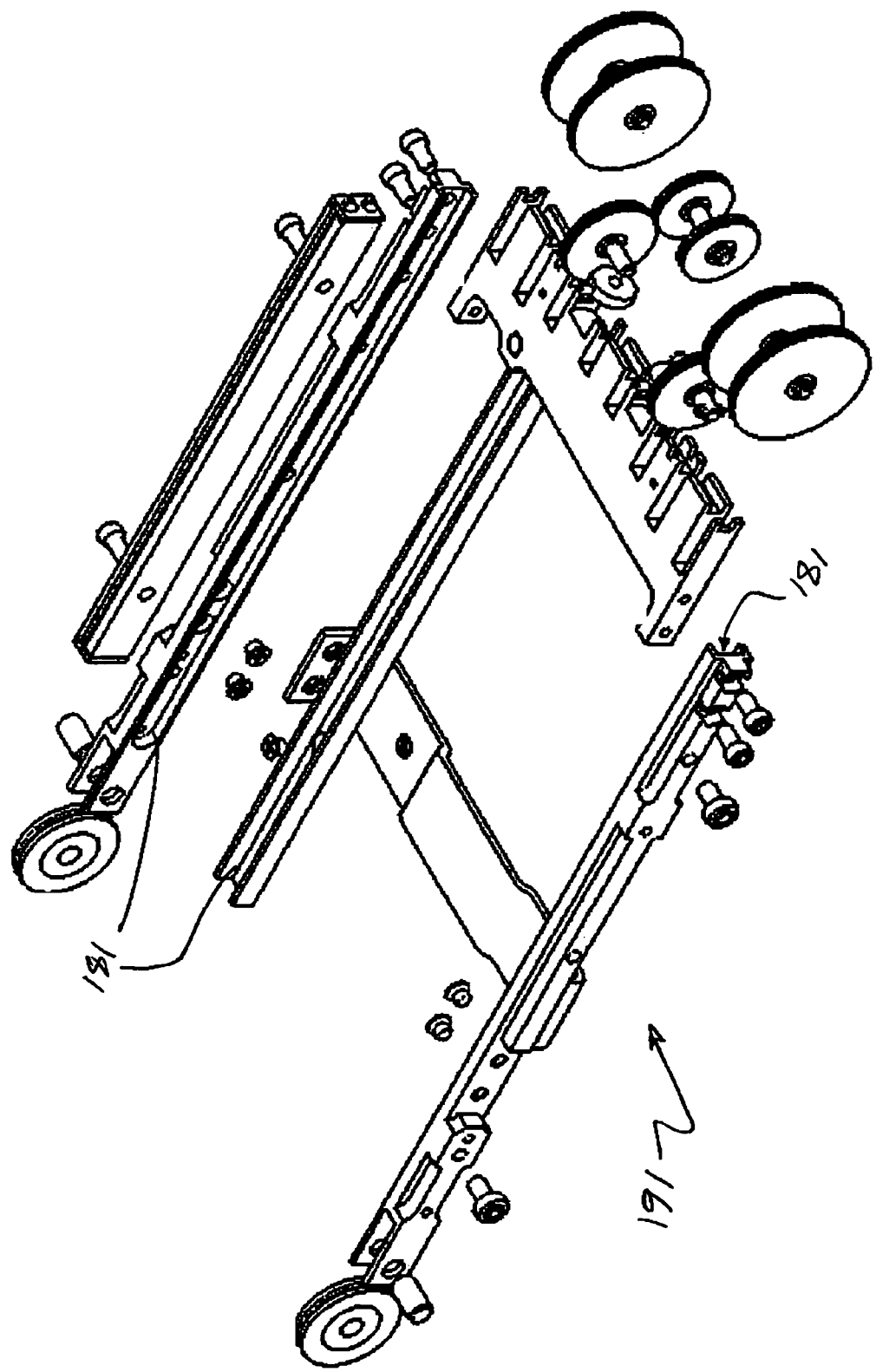
FIG. 48 is an exploded view illustrating relative constrained motion of a carriage base relative to an interface frame in the assembly of FIG. 40.

Referring to FIG. 46, a winged split carriage assembly is depicted in semi-exploded view. The winged carriage base (173) is configured to rotatably support two independently rotatable wing structures (221), each comprising a bottom portion (165) and a top portion (163). A further exploded view of the wing structures (221) and associated members are depicted in FIG. 47. Rotatably coupled to the rotatable wing structures (221) is a set of control element pulleys (167) to which a splined instrument interface socket (161) is coupled. The winged carriage base (173) is configured to slidably couple to a carriage interface frame (not shown) with bearings (179). As shown in FIG. 48, slots (181) constrain the motion of the winged carriage base (173) relative to the carriage interface frame (191) to linear motion. Shafts and bearings are utilized to rotatably couple the wing structures (221) to the winged carriage base and facilitate rotational motion of the wing structures (221) about the axis of the pertinent coupling shaft (171). Similar shaft and bearing configurations are utilized to provide for rotation of the control element pulleys (167) relative to the wing structures (221).

Thus, the winged split carriage design is configured to allow for independent motion of each of two wing structures (221), while also allowing for independent rotational motion of two sets of control element pulleys (167) and thereby instrument interface sockets (161). In other words, with the winged guide instrument (215) coupled to an arcuate slot instrument mounting base (187), and two control element interface assemblies (147) coupled to two instrument interface sockets positioned below the mounting base (187) (as depicted in FIG. 40), each of the control element interface assemblies (147) may be rotated about their longitudinal axis, and also arcuately translated through the arcuate slot formed in the instrument base (141). This arrangement provides for tensioning and control of two control elements, one around each of the control element pulleys (167) on each of the control element interface assemblies (147), with actuation of a single control element interface assembly (147). Thus, four control elements may be driven with the actuation of only two control element interface assemblies (147).

Figure 49:
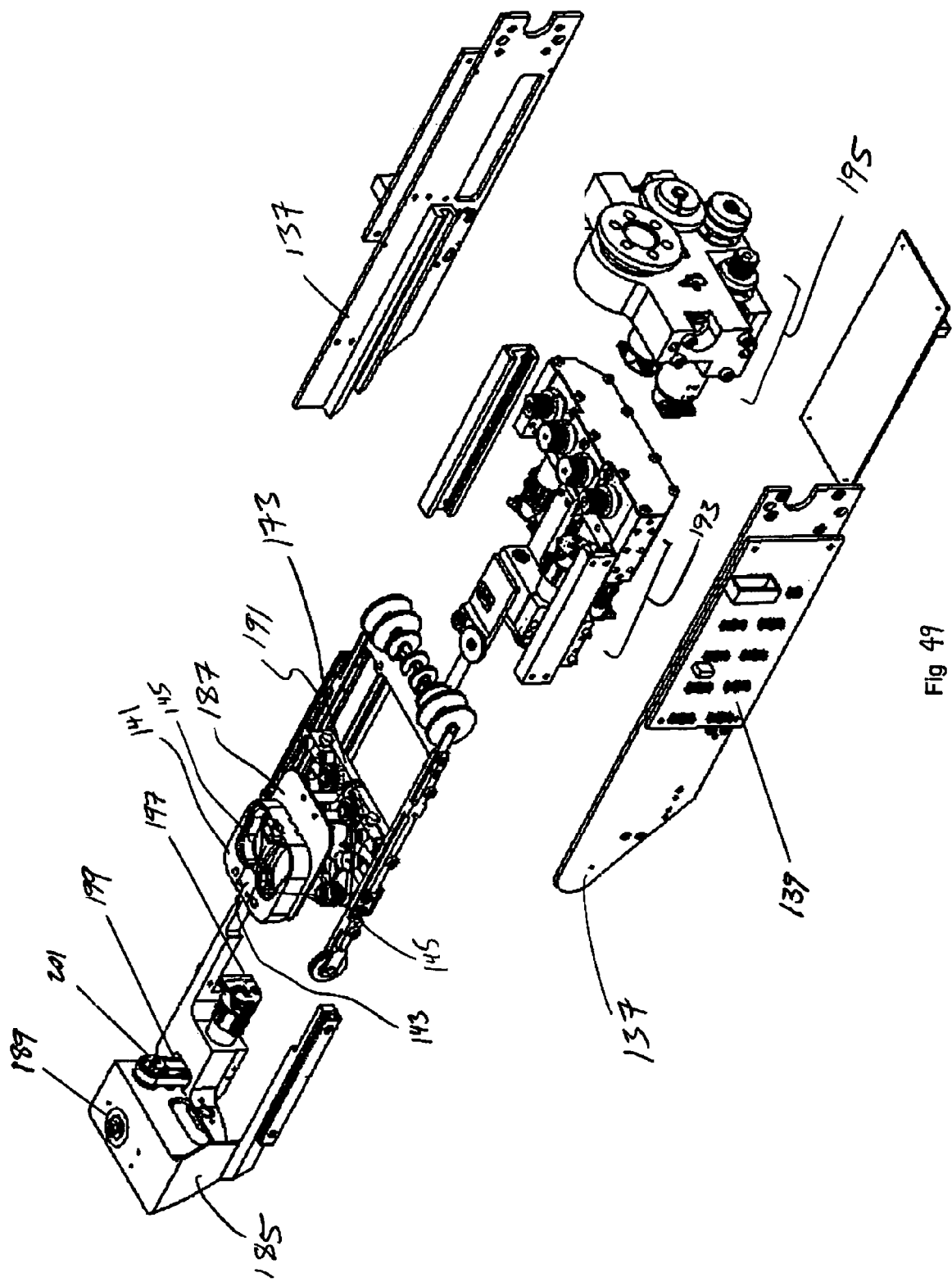

Referring to FIG. 49, an exploded view of an assembly similar to that depicted in FIG. 40 is depicted. Neither the sheath instrument, the two control element interface assemblies, nor the guide instrument catheter member are depicted in FIG. 49. As with aforementioned embodiments, the instrument driver roll assembly (195) and instrument driver motor/gear assembly (193) are coupled to the main frame (137) of the instrument driver. As shown in FIG. 50, redundant encoder readers (211) associated with each of four control element drive motors (209) of this embodiment facilitate high precision rotational position readings of the motor shafts and prevent position read errors. The motor output shafts are coupled to bevel gears (207) which are interfaced with another set of bevel gears (213) and thereby configured to drive the depicted vertical output shafts (205). The motor/gear interface block (203) is utilized to couple the motors, gears, and shafts into positions relative to each other and the main frame of the instrument driver (not shown), while constraining motions generally to rotational motions of shafts, motors, gears, and bearings. The rotation and arcuate translation of the winged structure instrument interface sockets (161) relative to the winged carriage base (173) and wing structures (221) is a key difference between the winged split carriage instrument driver and the non-winged embodiments described herein.

While multiple embodiments and variations of the many aspects of the invention have been disclosed and described herein, such disclosure is provided for purposes of illustration only.

What is claimed:
1. A catheter instrument, comprising:
an elongate flexible catheter member;
first and second control elements extending within the catheter member and secured to a distal end portion thereof, such that axial movement of one or both of the first and second control elements causes a corresponding bending motion of the catheter member distal end portion; and
a drivable assembly fixedly mounted to a proximal end of the catheter member, the drivable assembly comprising a base housing and a control element interface moveably mounted within the base housing and coupled to the respective first and second control elements, wherein the control element interface is configured to rotate relative to the base housing to thereby axially move the first control elements relative to the catheter member, and to translate relative to the base housing to thereby axially move the second control element relative to the catheter member,
wherein the base housing comprises a slot in which the control element interface is moveably mounted, and wherein the control element interface is configured to both rotate and axially translate within the slot relative to the base housing to thereby respectively axially move the first and second control elements relative to the catheter member.

2. The catheter instrument of claim 1, wherein the slot is a rectilinear slot.

3. The catheter instrument of claim 1, wherein the slot is an arcuate slot.

4. The catheter instrument of claim 1, wherein the base housing comprises a top and bottom portions having opposing catheter recesses, and the catheter member is received within the opposing catheter recesses when the top and bottom portions are sandwiched together.

5. A robotic medical system, comprising:
a catheter instrument, comprising
an elongate flexible catheter member,
first and second control elements extending within the catheter member and secured to a distal end portion thereof, such that axial movement of one or both of the first and second control elements causes a corresponding bending motion of the catheter member distal end portion, and
a drivable assembly fixedly mounted to a proximal end of the catheter member, the drivable assembly comprising a base housing and a control element interface moveably mounted within the base housing and coupled to the respective first and second control elements, the control element interface being configured to rotate relative to the base housing to thereby axially move the first control element relative to the catheter member, and to translate relative to the base housing to thereby axially move the second control element relative to the catheter member; and an instrument driver comprising
a mounting surface on which the catheter instrument base housing is mounted, and
a movable drive element mated with the control element interface, wherein the drive element is configured to rotate and translate the control element interface relative to the base housing,
wherein the base housing comprises a slot in which the control element interface is movably mounted, and wherein the control element interface is configured to both rotate and axially translate within the slot relative to the base housing to thereby respectfully axially move the first and second control elements relative to the catheter member.

6. The medical system of claim 5, wherein the slot is a rectilinear slot and the movable element is configured to move in a rectilinear path.

7. The medical system of claim 5, wherein the slot is an arcuate slot and the movable element is configured to move in an arcuate path.

8. The medical system of claim 5, wherein the instrument driver further comprises a movable carriage on which the mounting surface is disposed.

9. The medical system of claim 5, wherein the catheter instrument base housing comprises a top and bottom portions having opposing catheter recesses, and the catheter member is received within the opposing catheter recesses when the top and bottom portions are sandwiched together.

10. The medical system of claim 5, wherein the instrument driver comprises a first motor operatively coupled to translate the movable element relative to the catheter instrument base housing, and a second motor operatively coupled to rotate the movable element.

11. A catheter instrument, comprising:
an elongate flexible catheter member;
a plurality of control elements extending within the catheter member and secured to a distal end portion thereof, such that axial movement of one or more of the control elements causes a corresponding bending motion of the catheter member distal end portion; and
a drivable assembly fixedly mounted to a proximal end of the catheter member, the drivable assembly comprising a base housing having a first slot and a second slot, and corresponding first and second control element interfaces moveably mounted within the base housing, wherein a first pair of control elements are coupled to the first control element interface, and a second pair of control elements are coupled to the second control element interface, the first control element interface configured to both rotate and axially translate within the first slot relative to the base housing to thereby respectively axially move the first pair of control elements relative to the catheter member, and the second control element interface configured to both rotate and axially translate within the second slot relative to the base housing to thereby respectively axially move the second pair of control elements relative to the catheter member.

12. The catheter instrument of claim 11, wherein each of the slots is a rectilinear slot.

13. The catheter instrument of claim 11, wherein each of the slots is an arcuate slot.

14. The catheter instrument of claim 11, wherein the base housing comprises a top and bottom portions having opposing catheter recesses, and the catheter member is received within the opposing catheter recesses when the top and bottom portions are sandwiched together.

15. A medical instrument system, comprising:
a catheter instrument, comprising
an elongate flexible catheter member,
a plurality of control elements extending within the catheter member and secured to a distal end portion thereof, such that axial movement of one or more of the control elements causes a corresponding bending motion of the catheter member distal end portion, and
a drivable assembly mounted to a proximal end of the catheter member, the drivable assembly comprising a base housing having a first slot and a second slot, and first and second control element interface assemblies mounted within the base housing, the first control element interface assembly being configured to rotate and translate within the first slot relative to the base housing to thereby axially move a first pair of control elements relative to the catheter member, and the second control element interface assembly being configured to rotate and translate within the second slot relative to the base housing to thereby axially move a second pair of control elements relative to the catheter member; and
an instrument driver comprising
a mounting surface on which the catheter instrument base housing is mounted; and
a first movable drive element configured to rotate and translate the first control element interface assembly relative to the base housing, and a second movable drive element configured to rotate and translate the second control element interface assembly relative to the base housing.

16. The medical instrument system of claim 15, wherein the first and second slots are rectilinear slots, and the first and second movable elements are configured to move in respective rectilinear paths.

17. The medical instrument system of claim 15, wherein the first and second slots are arcuate slots, and the first and second movable elements are configured to move in respective arcuate paths.

18. The medical instrument system of claim 15, wherein the instrument driver further comprises a movable carriage on which the mounting surface is disposed.

19. The medical instrument of claim 15, wherein the instrument driver comprises a first motor operatively coupled to translate the first movable element, a second motor operatively coupled to rotate the first movable element, a third motor operatively coupled to translate the second movable element, a forth motor operatively coupled to rotate the second movable element.

* * * * *